US006479263B1

(12) United States Patent
Slawin et al.

(10) Patent No.: US 6,479,263 B1
(45) Date of Patent: Nov. 12, 2002

(54) METHOD FOR DETECTION OF MICROMETASTATIC PROSTATE CANCER

(75) Inventors: Kevin M. Slawin, Houston, TX (US); Donald J. Tindall, Rochester, MN (US); Charles Y. F. Young, Rochester, MN (US); Mohammad Saeed Saedi, San Diego, CA (US); Abhay Kumar, San Diego, CA (US); Harry G. Rittenhouse, Del Mar, CA (US); Robert L. Wolfert, San Diego, CA (US)

(73) Assignees: Baylor College of Medicine, Houston, TX (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 08/843,076

(22) Filed: Apr. 11, 1997

Related U.S. Application Data

(63) Continuation-in-part of application No. 08/759,354, filed on Nov. 14, 1996.

(51) Int. Cl.[7] ................................................. C12P 19/34
(52) U.S. Cl. .................... 435/91.2; 435/6; 435/9.23; 536/24.3; 536/24.31; 536/24.33; 536/25.3
(58) Field of Search ............................ 536/24.3, 24.31, 536/24.33, 25.3, 23.5; 435/6, 7.23, 91.2

(56) References Cited

U.S. PATENT DOCUMENTS

| | | |
|---|---|---|
| 3,817,837 A | 6/1974 | Rubenstein et al. ......... 435/7.9 |
| 3,842,067 A | 10/1974 | Sarantakis ................. 530/311 |
| 3,850,752 A | 11/1974 | Schuurs et al. ............ 435/7.93 |
| 3,862,925 A | 1/1975 | Sarantakis et al. .......... 530/311 |
| 3,901,654 A | 8/1975 | Gross ........................ 436/172 |
| 3,935,074 A | 1/1976 | Rubenstein et al. ......... 435/7.9 |
| 3,972,859 A | 8/1976 | Fujino et al. ................ 530/313 |
| 3,984,533 A | 10/1976 | Uzgiris ...................... 436/516 |
| 3,996,345 A | 12/1976 | Ullman et al. .............. 436/537 |
| 4,034,074 A | 7/1977 | Miles ........................ 436/518 |
| 4,092,408 A | 5/1978 | Litt .......................... 436/531 |
| 4,098,876 A | 7/1978 | Piasio et al. ............... 436/500 |
| 4,105,602 A | 8/1978 | Colescott et al. ........... 524/577 |
| 4,353,982 A | 10/1982 | Gomez et al. ............... 435/7.4 |
| 4,371,515 A | 2/1983 | Chu ........................... 436/544 |
| 4,446,122 A | 5/1984 | Chu et al. .................. 435/7.23 |
| 4,487,715 A | 12/1984 | Nitecki et al. .............. 530/334 |
| 4,629,783 A | 12/1986 | Cosand et al. .............. 530/324 |
| 4,757,048 A | 7/1988 | Lewicki et al. ............... 514/11 |
| 4,792,528 A | 12/1988 | Canfield et al. ............. 436/515 |
| 5,516,639 A | 5/1996 | Tindall et al. ............... 435/7.4 |
| 5,614,372 A | 3/1997 | Lilja et al. ................. 435/7.23 |
| 5,935,818 A | 8/1999 | Israeli et al. ............... 435/69.3 |

FOREIGN PATENT DOCUMENTS

| | | | |
|---|---|---|---|
| EP | 02228243 | 7/1987 | |
| EP | 0297913 | 1/1989 | ........... C12N/15/00 |
| EP | 0 571 911 | * 1/1993 | |
| WO | 94/10343 | 5/1994 | |
| WO | 94/27152 | 11/1994 | ......... G01N/33/574 |
| WO | 94/07329 | 2/1995 | |
| WO | 95/03334 | 2/1995 | ........... C07K/16/40 |
| WO | 95/28498 | 10/1995 | |
| WO | 95/30758 | * 11/1995 | |
| WO | 96/21042 | 7/1996 | |
| WO | 96/26272 | 8/1996 | |
| WO | 96/26442 | 8/1996 | ......... C01N/33/574 |
| WO | 96/34964 | 11/1996 | |
| WO | 97/01630 | 1/1997 | |
| WO | 97/07242 | 2/1997 | ............ C12Q/1/68 |
| WO | 98/02748 | 1/1998 | ......... G01N/33/574 |

OTHER PUBLICATIONS

Altman, P., et al., "Inbred and Genetically Defined Strains of Laboratory Animals", In: *Biological Handbooks, III*, Federation of American Societies for Experimental Biology, Bethesda, Maryland, pp. 21–29, (1979).

Andrews, P., et al., "Tumor–Promoting Phorbol Ester Down– Regulates the Androgen Induction of Prostate–Specific Antigen in a Human Prostatic Adenocarcinoma Cell Line", *Cancer Research*, 52, 1525–1529, (Mar., 1992).

Angermann, A., et al., "Purifications and Characterization of Human Salivary–Gland Prokallikrein from Recombinant Baculovirus–Infected Insect Cells", *Eur. J. Biochem.*, 206, 225–233, (1992).

Baker, A., "Human Kidney Kallikrein: cDNA Cloning and Sequence Analysis", *DNA*, 4, 445–450, (1985).

Berg, T., et al., "A Common Nonmenclature for Members of the Tissue (Glandular) Kallikrein Gene Families", In: *Recent Progress on Kinins*, Birkhauser Verlag, Basel, pp. 19–25, (1992).

Bridon, D.P., et al., "Structural Comparison of Prostate–Specific Antigen and Human Glandular Kallikrein Using Molecular Modeling", *Urology*, 45, 801–806, (1995).

Carpino, L., et al., "The 9–FLuorenylmethoxycarbonyl Amino–Protecting Group", *J. Org. Chem.*, 37, 3404–3409, (1972).

Chang, C., et al., "Solid Phase Peptide Synthesis Using Mild Base Cleavage of $N^{\alpha}$–Fluornylmethyloxycarbonylamino Acids, Exemplified by using a Synthesis of Dihydrosomatostatin", *Int. J. Pept. Pro. Res.*, 11, 246–249, (1978).

(List continued on next page.)

Primary Examiner—Susan Ungar
Assistant Examiner—Minh-Tam Davis
(74) *Attorney, Agent, or Firm*—Schwegman Lundberg Woessner & Kluth

(57) ABSTRACT

Prostate cancer is detected by determining the presence of hK2 RNA in a physiological sample.

10 Claims, 30 Drawing Sheets

OTHER PUBLICATIONS

Chapdelaine, P., et al., "High Level Expression in the Prostate of a Human Glandular Kallikrein mRNA Related to Prostate–Specific Antigen", *FEBS Lett.*, 236, 205–208, (Aug., 1988).

Christensson, A.C., et al., "Enzymatic Activity of Prostate–Specific Antigen and its Reactions with Extracellular Serine Proteinase Inhibitors", *Eur. J. Biochem.*, 194, 755–763, (1990).

Christensson, A., et al., "Serum Prostate Specific Antigen Complexed to $\alpha$1–Antichymotrypsin as an Indicator of Prostate Cancer", *J. Urol*, 150, 100–105, (1993).

Clements, J.A., "The Glandular Kallikrein Family of Enzymes: Tissue–Specific Expression and Hormonal Regulation", *Endocr. Rev.*, 10, 393–419, (1989).

Clements, J.A., et al., "The Human Kallikrein Gene Family: A Diversity of Expression and Function", *Mol. Cell. Endocrinol.*, 99, c1–6, (1994).

Cohen, P., et al., "Biological Effects of PSA as an IGFBP–3 Protease", *In: Program and Abstracts 74th Annual Meeting of the Endocrine Society, San Antonio, TX*, 291, Abstract No. 960, (Jun., 1992).

Deperthes, D., et al., "Isolation of Prostatic Kallikrein hK2, also Known as hGK–1, in Human Seminal Plasma", *Biochim. Biophys. Acta*, 1245, 311–316, (1995).

Digby, M., et al., "Human Prostate Specific Antigen (PSA) Gene: Structure and Linkage to the Kallikrein–Like Gene", *Nuc. Acids Res.*, 17, 2137, (1989).

Drinkwater, C.C., et al., "Kallikreins, Kinins and Growth Factor Biosynthesis", *Trends Biochem. Sci.*, 13, 169–172, (1988).

Evans, B., et al., "Structure and Chromosomal Localization of the Human Renal kallikrein Gene", *Biochemistry*, 27, 3124–3129, (1988).

Fukushima, D., et al., "Nucleotide Sequence of Cloned cDNA for Human Pancreatic Kallikrein", *Biochemistry*, 24, 8037–8043, (1985).

Henttu, P., et al., "cDNA Coding for the Entire Human Prostate Specific Antigen Shows High Homologies to the Human Tissue Kallikrein", *Biochemical and Biophysical Research Communications*, 160, 903–910, (Apr., 1989).

Henttu, P., et al., "Expression of the Gene Coding for Human Prostate–Specific Antigen and Related hGK–1 in Benign and Malignant Tumors of the Human Prostate", *Int. J. Cancer*, 45, 654–660, (1990).

Hill, C.S., et al., "The Preparation of Monoclonal Antibodies Which React Preferentially with Human Bone Alkaline Phosphates and not Liver Alkaline Phosphatase", *Clinica Chemica Acta*, 186, 315–320, (1989).

Jones, T.H., et al., "Bioregulatory Role of the Kallikrein–Kinin System in the Normal Pituitary Gland and Its Tumors", *Acta–Endocrinol*, 127, 481–484, (1992).

Killian, C., et al., "Mitogenic Response of Osteoblast Cells to Prostate–Specific Antigen Suggests and Activation of Latent TGF–$\beta$ and a Proteolytic Modulation of Cell Adhesive Receptors", *Biochem. Biophys. Res. Comm.*, 192, 490–947, (1993).

Laemmli, U.K., "Cleavage of Structural Proteins During the Assembly of the Head of Bacteriophage T4", *Nature*, 227, 680–685, (Aug., 1970).

Lebeau, M., et al., "Report of the Committee on the Genetic Constitution of Chromosomes 18 and 19", *Cytogenet. Cell Genet.*, 51, 338–357, (1989).

Leinonen, J., et al., "Double–Label Time–Resolved Immunofleurometric Assay of Prostate–Specific Antigen and of its Complex with $\alpha_1$–Antichymotrypsin", *Clin. Chem.*, 39, 2098–2103, (1993).

Lottspeich, F., et al., "N–Terminal Amino Acid Sequence of Human Urinary Kallikrein Homology with Other Serine Proteases", *Hoppe–Seyler's Z. Physiol. Chem.*, 360, 1947–1950, (Dec., 1979).

Lovgren, J., et al., "Production of Recombinant PSA and HK2 and Analysis of Their Immunologic Cross–Reactivity", *Biochem Biophys Res. Comm.*, 231, 888–895, (1995).

Lu, H., et al., "Human Urinary Kallikrein", *Int. J. Peptide Protein Res.*, 33, 237–249, (1989).

Luckow, V.A., et al., "Trends in the Development of Baculovirus Expression Vectors", *Bio/Technology*, 6, 47–55, (Jan., 1988).

Lundwall, A., "Characterization of the Gene for Prostate–Specific Antigen, a Human Glandular Kallikrein", *Biochem. Biophys. Research Comm.*, 161, 1151–1159, (Jun., 1989).

Lundwall, A., et al., "Molecular Cloning of Human Prostate Specific Antigen cDNA", *FEBS Lett.*, 214, 317–324, (Apr., 1987).

McCormack, R., et al., "Molecular Forms of Prostate–Specific Antigen and the Human Kallikrein Gene Family: A New Era", *Urology*, 45, 729–744, (May 1995).

Merrifield, R., "Solid Phase Peptide Synthesis. I. The Synthesis of a Tetrapeptide", *J. Am. Chem. Soc.*, 85, 2149–2154, (Jul., 1963).

Mikolajczyk, S.D., et al., "Studies on the Substrate Specificity and Inhibition of Human Glandular Kallikrein (hK2)", Poster Abstract, Keystone Symposium, (Mar., 1996).

Montgomery, B., et al., "Hormonal Regulation of Prostate–Specific Antigen (PSA) Glycoprotein in the Human Prostatic Adenocarcinoma Cell Line, LNCaP", *The Prostate*, 21, 63–73, (1992).

Morris, B., "hGK–1: A Kallikrein Gene Expressed in Human Prostate", *Clin. Exp. Pharmacol. Physiol*, 16, 345–351, (1989).

Murtha, P., et al., "Androgen Induction of a Human Prostate–Specific Kallikrein hKLK2: Characterization of an Androgen Response Element int he 5' Promoter Region of the Gene", *Biochemistry*, 32, 6459–6464, (1993).

Paradis, G., et al., "Looking for Human Glandular Kallikrein–1 in the Prostate", *The Prostate*, 15, 343–353, (1989).

Phronen, T., et al., "Immunofluorometric Assay for Sensitive and Specific Measurement of Human Prostatic Glandular Kallifrein (hK2) in Serum", *Clin. Chem.*, 42, 1034–1041, (1996).

Qui, S., et al., "In Situ Hybridization of Prostate–Specific Antigen mRNA in Human Prostate", *J. Urology*, 144, 1550–1556, (1990).

Rahn, H.P., et al., "Expression of Human Salivary–Gland Kallikrein in Insect Cells by a Baculovirus Vector", *In: Recent Progress in Kinins*, H. Fritz, et al., (eds.), Birkhauser Verlag, Basel, 66–73, (1992).

Ransom, J.P., "Practical Competitive Binding Assay Methods;", The C. V. Mosby Company, St. Louis, 1–9, 54–61, (1976).

Riegman, P., et al., "Characterization of the Prostate–Specific Antigen Gene: A Novel Human Kallikrein–Like Gene", *Biochem. Biophys. Res. Comm.*, 159, 95–102, (Feb., 1989).

Riegman, P., et al., "Identification and Androgen–Regulated Expression of Two Major Human Glandular Kallikrein–1 (hKG–+) mRNA Species", *Mol. Cell. Endocrinol.*, 76, 181–190, (1991).

Riegman, P., et al., "The Prostate–Specific Antigen Gene and the Human Glandular Kallikrein–1 Gene are Tandemly Located on Chromosome 19", *FEBS Lett.*, 247, 123–126, (Apr., 1989).

Ropers, H., et al., "Report of the Committee on the Genetic Constitution of Chromosome 19", *Cytogenet. Cell Genet.*, 55, 218–228, (1990).

Rosenberg, A., et al., "Vectors for Selective Expression of Cloned DNAs by T7 RNA Polymerase", *Gene*, 56, 125–135, (1987).

Sambrook, J., et al., "Screening Expression Libraries with Antibodies and Oligonucleotides", *Molecular Cloning, a Laboratory Manual, 2nd Edition*, pp. 12.2–12.15, (1989).

Schedlich, L.J., et al., "Kallikrein Genes: Cloning in Man and Expression in Rat Renal Hypertension", *Journal of Hypertension Supplement*, 6, S395–S398, (Dec., 1988).

Schedlich, L.J., et al., "Primary Structure of a Human Glandular Kallikrein Gene", *DNA*, 6, 429–437, (1987).

Schedlich, L.J., et al., "Three Alu Repeated Sequences Associated with a Human Glandular Kallikrein Gene", *Clin. Exper. Pharmacology & Physiology*, 15, 339–344, (1988).

Schulz, P., et al., "Sequence of a cDNA Clone Encompassing the Complete Mature Human Prostate Specific Antigen (PSA) and an Unspliced Leader Sequence", *Nuc. Acids Res.*, 16, 6226, (1988).

Scorer, C., et al., "Rapid Selection Using G418 of High Copy Number Transformants of Pichia Pastoris for High–Level Foreign Gene Expression", *Biol/Technology*, 12, 181–184, (Feb., 1994).

Sutherland, G., et al., "Human Prostate–Specific Antigen (APS) is a Member of the Glandular Kallikrein Gene Family at 19p13", *Cytogenet. Cell Genet.*, 48, 205–207, (1988).

Tijssen, P., "Practices and Theory of Enzyme Immunoassays", *In Laboratory Techniques in Biochemistry and Molecular Biology*, vol. 15, R.H. Burdon, (ed.), Elsevier, New York, 43–78, 95–121, 297–383. (1985).

Vinhinen, M., "Modeling of Prostate Specific Antigen and Human Glandular Kallikrein Structures", *Biochem. Biophys. Res. Comm.*, 204, 1251–1256, (1994).

Wang, J., et al., "Purification and Characterization of recombinant tissue kallikrein from *Escherichia coli* and yeast", *Biochem. J.*, 276, 63–61, (1991).

Watt, K., et al., "Human prostate–Specific Antigen: Structural and Functional Similarity with Serine Proteases", *PNAS USA*, 83, 3166–31709, (May, 1990).

Young, C.F., et al., "Expression and Androgenic Regulation of Human Prostate Specific Kallikreins", *J. Androl*, 16, 97–99, (1995).

Young, C.F., et al., "Hormonal Regulation of Prostate–Specific Antigen Messenger RNA in Human Prostatic Adenocarcinoma Cell Line LNCap", *Cancer Research*, 51, 3748–3752, (Jul., 1991).

Young, C., et al., "Tissue Specific and Hormonal Regulation of Human Prostate–Specific Glandular Kallikrein", *Biochemistry*, 31, 818–824, (1992).

Charlesworth, M.C., et al., "Detection of a Prostate–Specific Protein, Human Glandular Kallikrein (hK2), In Sera of Patients with Elevated Prostate–Specific Antigen Levels", *Urology*, 49, 487–493, (1997).

Clements, J., et al., "Glandular Kallikreins and Prostate–Specific Antigen Are Expressed in the Human Endometrium", *Journal of Clinical Endocrinology and Metabolism*, vol. 78, No. 6, pp. 1536–1549, (1994).

Corey, E., et al., "Detection of Circulating Prostate Cells by Reverse Transcriptase–Polymerase Chain Reaction of Human Glandular Kallikrein (hK2) and Prostate–Specific Antigen (PSA) Messages", *Urology*, 50, 184–188, (Aug. 1997).

Saedi, M.S., et al., "Overexpression of a Human Prostate–Specific Glandular Kallikrein hK2 in *E. Coli* and Generation of Antibodies", *Molecular and Cellular Endocrinology,*, vol. 109, 237–241, (Feb. 1995).

Ashley, P.L., et al., "Kallikrein–Related mRNAs of the Rat Submaxillary Gland: Nucleotide Sequences of Four Distinct Types Including Tonin", *Biochemistry*, 24, 4512–4520, (1985).

Ashley, P.L., et al., "Tissue–Specific Expression of Kallikrein–Related Genes in the Rat", *Biochemistry*, 24, 4520–4527, (1985).

Deguchi, T., et al., "Detection of Micrometastic Prostate Cancer Cells in Lymph Nodes by Reverse Transcriptase––Polymerase Chain Reaction", *Cancer Research*, vol. 53, 5350–5354, (Nov. 15, 1993).

Husmann, D.A., et al., "Antipeptide Antibodies to Two Distinct Regions of the Androgen Receptor Localize the Receptor Protein to the Nuclei of Target Cells in the Rat and Human Prostrate", *Endocrinology*, 126 (5), pp. 2359–2360, (1990).

Kuus–reichel, K., et al., "Production of IgG Monoclonal Antibodes to the Tumor Associated Antigen, CA–195", *Hybridoma*, 13, 31–36, (1994).

Qui, S., et al., "In Situ Hybridization of Prostate–Specific Antigen Gene: A Novel Human Kallikrein–Like Gene", *Biochem. Biophys. Res. Comm.*, 159, 95–102, (Feb., 1989).

Takayama, T.K., et al., "Newer Applications of Serum Prostate–Specific Antigen in the Management of Prostate Cancer", *Seminars in Oncology*, vol. 21, No. 5, 542–553, (Oct. 1994).

Van Leewen, B.H., et al., "Mouse Glandular Kallikrein Genes", *J. Bio. Chem.*, 261, 5529–5535, (1986).

Allred, D.C., et al., "Association of p53 Protein Expression with Tumor Cell Proliferation Rate and Clinical Outcome in Node–Negative Breast Cancer", *J. Natl. Cancer Inst.*, 85, 200–206 (1993).

Finlay, J.A., et al., "Development of a Dual Monoclonal Antibody Sandwich Assay for Human Glandular Kallikrein (hK2) with Minimal Cross Reactivity to Prostatic Specific Antigen (PSA)", *Clinical Chemistry*, 42, Abstract No. 683, p. S259 (1996).

Fugger, L., et al., "Expression of HLA–DR4 and Human CD4 Transgenes in Mice Determines the Variable Region β–chain T–cell Repertoire and Mediates an HLA–DR–Restricted Immune Response", *Proc. Natl. Acad. Sci. USA*, 91, 6151–6155 (Jun. 1994).

Grauer, L.S., et al., "Identification of Human Glandular Kallikrein hK2 from LNCaP Cells", *Journal of Andrology*, 17, 353–359 (Jul./Aug. 1996).

Herrala, A., et al., "Human Prostate–Specific Glandular Kallikrein is Expressed as an Active and an Inactive Protein", *Clinical Chemistry*, 43, 279–284 (1997).

Kumar, A., et al., "Expression of Human Glandular Kallikrein, hK2, in Mammalian Cells", *Cancer Research*, 56, 5397–5402 (Dec. 1, 1996).

Liu, X.L., et al., "Identification of a Novel Serine Protease–like Gene, the Expression of Which is Down–Regulated during Breast Cancer Progression", *Cancer Research, 56*, 3371–3379 (Jul. 15, 1996).

Mikolajczyk, S.D., et al., "Ala217 is Important for the Catalytic Function and Autoactivation of Human Glandular Kallikrein, hK2", *Eur. J. Biochem., 246*, 440–446 (1997).

Young, C.Y., et al., "Prostate–Specific Human Kallikrein (hK2) as a Novel Marker for Prostate Cancer", *Prostate Supplement, 7*, 17–24 (1996).

Corey, E., et al., "Improved reverse transcriptase–polymerase chain reaction protocol with exogenous internal competitive control for prostate–specific antigen mRNA in blood and bone marrow", *Clin. Chem., 43 (3)*, pp. 443–452, (1997).

de Vries, G.M., et al., "Qualitative and Quantitative RT–PCR For PSA: Molecular Staging of Prostate Cancer", *Proceedings of the American Urological Association, 155 (Suppl. 417A)*, Abstract No. 426, 1 p., (May 1996).

Diamandis, E., et al., "Prostate Cancer, Prostate–Specific Antigen, and the Polymerase Chain Reaction", *Clin. Chem., 41/2*, pp. 177–79, (1995).

Ellis, W.J., et al., "The Value of a Reverse Transcriptase Polymerase Chain Reaction Assay in Preoperative Staging and Followup of Patients with Prostate Cancer", *The Journal of Urology, 159*, pp. 1134–1138, (Apr. 1998).

Grauer, L., et al., "Induction of an hK2–like Immunoreactive Protein in LNCap Cells with Milbolerone", *Proceedings of the 86th Annual American Association for Cancer Research Meeting, 36*, Absbtract No. 1585, p. 266, (Mar. 1995).

Ignatoff, J.M., et al., "Prostate Specific Antigen (PSA) Reverse Transcriptase–Polymerase Chain Reaction (RT–PCR) Assay in Preoperative Staging of Prostate Cancer", *Proceedings of the American Urological Association, 155 (Suppl. 417A)*, Abstract No. 427, 1 p., (May 1996).

Rittenbouse, H., et al., "Characterization and Evaluation of hK2: A Potential Prostate Cancer Marker, Closely Related to PSA", *Monaco, 1996*, 25 p., (Jul. 1997).

Slawin, K., et al., "Comparison of Results Obtained Using Different RT–PCR–PSA Assay Methods on a Single Set of Clinical Specimens", *Proceedings of the American Urological Association, 155 (Suppl. 417A)*, Abstract No. 425, 1 p., (May 1996).

Sokoloff, M., et al., "Quantitative Polymerase Chain Reaction (PCR) Does Not Improve Prostate Cancer (PC) Staging A Clinical–Pathologic–Molecular Analysis of 121 Patients", *Proceedings of the American Urological Association, 155 (Suppl. 417A)*, Abstract No. 428, 1 p., (May 1996).

Tockman, M.S., et al., "Considerations in Bringing a Cancer Biomarker to Clinical Application", *Cancer Research (Suppl.), 52*, pp. 2711s–2718s, (May 1, 1992).

Verghaegen, M., et al., "Quantification of prostate–specific antigen mRNA by coamplification with a recombinant RNA internal standard and microtiter well–based hybridization", *Clinical Chemistry, 44 (6)*, pp. 1170–1176, (1998).

* cited by examiner hK2: IVGGWECEKHSQPWQVAV SHGWAHCGGVLVHPQWVLTAAHCLKKNSQVWLGRHN
hK3: """""""""""""""""L"A"R"R"V""""""""""""""""""""IRNK"VIL""""S LFEPEDTGQRVPVSHSFPHPLYNMSLLKHQSLRPDEDSSHDLMLLRLSEPAKIT
_"H""""""VFQ""H""""""D""""NRF"""GD"""""""""""""""EL"

DVVKVLGLPTQEPALGTTCYASGWGSIEPEEFLRPRSLQCVSLHLLSNDMCA
"A"""MD""""""""""""""""""""""TPKK""""D""VI"""V""

RAYSEKVTEFMLCAGLWTGGKDTCGGDSGGPLVCNGVLQGITSWGPEPCALPEKP
QVHPQ"""K""""""R"""""S""S"""""""""""""""""""""""S""""""R"

AVYTKVVHYRKWIKDTIAANP
SL"""""""""""""""V"""

FIG. 1

FIG. 2 hK2 cDNA

```
                                                                pphK2                                          phK2                                    hK2
-76   CAGGATGTGGGAGGCTGGTTCTCTCCATGCCTTGTCTGTGGGGTGCACTGGTGCCCCTCATCCAGTCTCCGA
                                                                GTGCCCCTCATCCAGTCTCCGA
         1►MetTrpAspLeuValLeuSerIleAlaLeuValGlyCysThrValGlyAlaValProLeuIleGlnSerArg
                                                                             1►I
                                                                                ValProLeuIleGlnSerArg
  2   TTGTGGGAGGCTGGTGGAGTGTGAGAAGCATTCCCAACCCTGGCCAGGTGGTGTACAGTCATGATGGGCACACTGT
        leValGlyGlyTyrTrpGluCysGluLysHisSerGlnProTrpGlnValValTyrSerHisGlyTrpAlaHisCys
 79   GGGGGTGTCCTGTGCACCCCCAGTGGGTGCTCACAGTGCCCATTGCCTAAAGAAGAATAGCCAGGTCTCGGTGGG
        GlyGlyValLeuValHisProGlnTrpValLeuThrAlaAlaHisCysLeuLysLysAsnSerGlnValTrpLeuGl
156   TCGGCACAACCTGTTTGAGCCTGAAGACACAGGCCAGAGGGTCCCTGTCAGCCACAGCTTCCCACACCCGCTCTACA
        yArgHisAsnLeuPheGluProGluAspThrGlyGlnArgValProValSerHisSerPheProHisProLeuTyrA
233   ATATGAGCCTTCTGAAGCATCACAAGCCTTAGACCAGAAGATGAAGACCTAGGGCCTGCCCACCCAGCTCATGCTGCCTGTCA
        snMetSerLeuLeuLysHisGlnSerLeuLeuArgProAspLeuLeuArgLeuLeuArgSer
310   GAGCCTGCCAAGATCACAGATGTTGTGAAGGTCCTGGGCCTGCCCACCCAGGAGCCAGACTGGGACCACTGCTA
        GluProAlaLysIleThrAspValValLysValLeuGlyLeuProThrGlnGluProAlaLeuGlyThrThrCysTy
387   CGCCTCAGGCTGGGGCAGCATCGAGCCCGAGGAGTTCTTGAGACCCAGGAGTCTTGAGGTGTGAGCCTCCATCTCC
        rAlaSerGlyTrpGlySerIleGluProGluGluPheLeuArgProArgSerLeuGlnCysValSerLeuHisLeuL
464   TGTCCAATGACACATGTGCTAGACCTTACTCTGAGAAGGTGACAGAGTTCATGTTGTGTGCTGGGCTCTGGACAGT
        euSerAsnAspThrCysAlaArgAlaTyrSerGluLysValThrGluPheMetLeuCysAlaGlyLeuTrpThrGly
541   GGTAAAGACACTTGTGGGGGTGATTCGGGGTGCCTGAAAAGCTGCTGTGTACACCAAGGTGGTGCATTACCGGAAGTGGATCAAGGAC
        GlyLysAspThrCysGlyGlyAspSerGlyGlyProLeuValCysAsnGlyValLeuGlnGlyIleThrSerTrpGly
618   CCCTGAGCCATGCCCTGCCTGAAAAGCTGCTGTGTACACCAAGGTGGTGCATTACCGGAAGTGGATCAAGGAC
        ProGluProCysAlaLeuProGluLysProAlaValTyrThrLysValHisTyrArgLysTrpIleLysAsp
694   ACCATCGCAGCCAACCCCTGAGTGCCCCT
232►  ThrIleAlaAlaAsnPro***ValPro
```

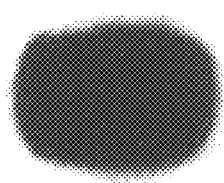 — 66kD
 — 31kD
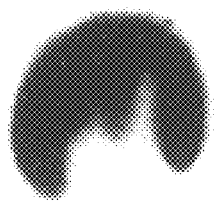 — 22kD
FIG. 8

1) CALPEKPAVY TKVVHY↓↧RKWI KDTIAAN

2) DRVY↧IHPFHLLVYS

3) VPLIQSR↓IVGGWEC

4) HCLKKNSQVWL↧GRHNL

5) FVNQHL↧CGSHLVEALYL↧VCGERGFFY↧TPKA

6) CSGKIVIAR↓YGKVF↧R↓GNK

↧ = PSA    ↓ = hK2

R= Arg; K= Lys; Y=Tyr; F= Phe; L= Leu; T= Thr

FIG. 16

```
              5'           SENSE PRIMER              3'
              ─────────────────────────────────────────▶ hK2:  a g t t c t t g c g c c c c a g g a g t
hK3:  a g t t c t t g a c c c c a a a g a a a
hK1   a t t g t a t g t g g g g c a g a c t
```

FIG. 25A

```
              3'         ANTI-SENSE PRIMER           5'
              ◀───────────────────────────────────────── hK2:  c a c a a a g a c g t g g g t g a c c a
hK3:  t c c a a t g a c g t g t g t g c g c a
hK1   g g c c a a c a t c t g g g t g c c a
```

FIG. 25B

METHOD FOR DETECTION OF MICROMETASTATIC PROSTATE CANCER

CROSS-REFERENCE TO RELATED APPLICATIONS

This application is a continuation-in-part of U.S. application Ser. No. 08/759,354, filed Nov. 14, 1996, the disclosure of which is incorporated by reference herein.

STATEMENT OF GOVERNMENT RIGHTS

This invention was made with the support of the U.S. Government via grants from the National Institutes of Health (Grant Nos. CA70893 and DK41995). The Government may have certain rights in this invention.

BACKGROUND OF THE INVENTION

The glandular kallikreins are a subgroup of serine proteases which are involved in the post-translational processing of specific polypeptide precursors to their biologically active forms. In humans, three members of this family have been identified, and some of their properties characterized (Clements, *Endoc. Rev.*, 10, 343 (1989); Clements, *Mol. Cell Endo.*, 99, 1 (1994); Jones et al., *Acta Endoc.*, 127, 481 (1992)). The hKLK1 gene encodes the tissue kallikrein protein, hK1, the hKLK2 gene encodes the prostate-specific glandular kallikrein protein, hK2, and the hKLK3 gene encodes the prostate-specific antigen protein, hK3 (PSA). Northern blot analysis of mRNA shows that both hK2 and PSA are expressed mainly in the human prostate, while expression of hK1 is found in the pancreas, submandibular gland, kidney, and other nonprostate tissues (Chapdelaine et al., *FEBS Lett.*, 236, 205 (1988); Young et al., *Biochem.* 31, 818 (1992)).

The nucleotide sequence homology between the exons of hKLK2 and hKLK3 is 80%, whereas the nucleotide sequence homology between the exons of hKLK2 and hKLK1 is 65%. The deduced amino acid sequence homology of hK2 to PSA is 78%, whereas the deduced amino acid sequence homology of hK2 to hK1 is 57%. Moreover, the deduced amino acid sequence of hK2 suggests that hK2 may be a trypsin-like protease, whereas PSA is a chymotrypsin-like protease.

PSA levels are widely used as a prognostic indicator of prostate carcinoma. However, since the concentration of PSA in serum is elevated in patients with either prostatic cancer (pCa) or benign prostatic hyperplasia (BPH), the detection of elevated levels of PSA does not distinguish between these diseases. Moreover, the high degree of homology of hK2 to PSA raises some question as to the specificity of antibodies currently used to detect the levels of PSA. If the levels of circulating hK2 are unrelated to pCa or BPH, then antibodies raised to preparations of PSA which are contaminated with hK2, or to regions of PSA with homology to hK2, can result in false positive results.

Although it is now generally accepted that serum PSA testing, combined with the digital rectal exam (DRE), is the most effective means to detect clinically significant and organ-confined prostate cancer, combinations of PSA, DRE and ultrasonic prostate examination can detect only some prostate tumors. For example, up to 40% of surgically treated patients with prostate cancer are subsequently found to be clinically understaged. Moreover, the actual incidence of histological cancers based on autopsy data relative to the incidence of clinically significant prostate cancer is high. Furthermore, approximately 30% of patients with alleged localized prostate cancer may have occult (distant) metastatic disease (Moreno et al., *Cancer Res.*, 52, 6110 (1992)). Of these patients, 80% experience relapse biochemically, i.e., elevated PSA levels, or by the recurrence of local, or occurrence of frank systemic, disease, after therapy.

Operative therapy is not the appropriate treatment modality for patients having established metastasis. Screening modalities to assess early metastases often fail to identify a significant subset of patients with locally invasive disease involving penetration of the prostate capsule or seminal vesicle. While immunohistochemical techniques have been employed to identify micrometastatic, or circulating, prostate tumor cells when no obvious metastatic deposit was evidenced by conventional means, immunohistochemical methods are laborious and lack the sensitivity needed for the early detection of metastatic or locally invasive prostate cancer.

There is, therefore, a need for early detection of prostate cancer cells with metastatic potential. Moreover, there is a need to accurately stage prostate cancer prior to subjecting a patient to invasive procedures. In particular, there is a need for a marker for prostate cancer that can function independently of, or in combination with, PSA.

SUMMARY OF THE INVENTION

The invention provides a diagnostic method for detecting hK2 DNA wherein the presence of prostate cancer cells in a physiological sample can be correlated to the detection of hK2 RNA in the sample. Because expression of hK2 is prostate tissue specific, hK2 RNA should theoretically not be detectable in cells present in bodily fluids or non-prostate tissue if there is no locally invasive or metastatic disease, or if all prostate tissue (benign and malignant) has been removed or destroyed. The method comprises contacting an amount of DNA obtained by reverse transcription (RT) of RNA from a human physiological sample with a plurality of oligonucleotide primers, preferably at least two oligonucleotide primers, at least one of which an hK2-specific oligonucleotide, in an amplification reaction so as to yield an amount of amplified hK2 DNA. A preferred amplification reaction is a polymerase chain reaction (PCR). The presence of the amplified hK2 DNA is then detected. Preferably, the conditions are effective to amplify the amount of DNA obtained by reverse transcription of RNA from at least one cell containing hK2 in a sample which comprises at least about $10^7$ to about $10^9$ cells. As described hereinbelow, the presence of amplified hK2 DNA in blood cells, after RT-PCR, is correlated with prostate cancer, i.e., sixty-seven percent (67%) of the prostate cancer patients expressed hK2, 17% expressed PSA, and 17% expressed both hK2 and PSA. Preferably, the source of the sample to be tested is human tissue, e.g., prostate, prostate capsule, seminal vesicle, bone marrow or lymph node. Another preferred source of the sample to be tested is a human physiological fluid which comprises cells, e.g., blood, serum, or seminal fluid.

As used herein, "amplified hK2 DNA" is defined to mean hK2 DNA in a sample, which was subjected to an amplification reaction, that is present in an amount that is greater than, i.e., 10, preferably $10^4$, and more preferably $10^6$, times greater than, the amount of hK2 DNA which was present in the sample prior to amplification.

As used herein, the term "hK2-specific oligonucleotide" or "hK2-specific primer" means a DNA sequence that has at least about 80%, more preferably at least about 90%, and more preferably at least about 95%, sequence identity or homology to SEQ ID NO:4 in regions of SEQ ID NO:4 that are divergent from nucleotide sequences which encode hK3 (SEQ ID NO:23). An oligonucleotide or primer of the invention has at least about 7–50, preferably at least about 10–40, and more preferably at least about 15–35, nucleotides. Preferably, the oligonucleotide primers of the invention comprise at least 7 nucleotides at the 3' of the oligonucleotide primer which have at least about 80%, more preferably at least about 85%, and more preferably at least about 90%, identity to SEQ ID NO:2, SEQ ID NO:4, or SEQ ID NO:6. The oligonucleotides of the invention may also include sequences which are unrelated to hK2 nucleic acid sequences, e.g., they may encode restriction endonuclease recognition sequences. A preferred hK2-specific oligonucleotide of the invention comprises SEQ ID NO:14. Another preferred hK2-specific oligonucleotide of the invention comprises SEQ ID NO:17. Yet another preferred hK2-specific oligonucleotide of the invention comprises SEQ ID NO:18.

A preferred diagnostic method of the invention combines RT-PCR detection of hK2 transcripts with RT-PCR detection of transcripts of other gene products associated with prostate cancer. Combined detection of two or more gene products may provide greater diagnostic certainty or yield more informative staging information. Combined detection may also be helpful in differentiating those cells with aggressive growth potential from those that are more indolent. In a particularly preferred embodiment of the method provided by the invention, RT-PCR detection of hK2 RNA is combined with RT-PCR detection of PSA RNA.

The invention further provides a diagnostic method for detecting hK2 RNA. The method comprises extracting RNA from a physiological sample obtained from a human. The extracted RNA is reverse transcribed to yield DNA. The DNA is contacted with an amount of at least two oligonucleotides effective to amplify the DNA to yield an amount amplified hK2 DNA, wherein at least one oligonucleotide is an hK2-specific oligonucleotide. The presence of the amplified hK2 DNA is then detected. The presence of the amplified hK2 DNA is indicative of metastatic prostate cancer in the human. Preferably, the conditions are effective to amplify the amount of DNA obtained by reverse transcription of RNA from at least one cell containing hK2 in a sample which comprises at least about $10^7$ to about $10^9$ cells.

The presence of hK2 RNA, or a level of hK2 RNA that rises over time, in bodily fluids or non-prostate tissue may be reasonably expected to indicate the presence of previously undiagnosed metastatic disease. Early detection of metastatic disease provides a "lead time" during which alternative therapeutic strategies, including those that may not exist at the time of surgery but are subsequently developed, can be evaluated. Thus, the present invention provides a method for monitoring the progression of prostate cancer.

The method comprises contacting an amount of DNA obtained by reverse transcription of RNA from a physiological sample obtained from a human afflicted with prostate cancer with an amount of at least two oligonucleotides, at least one of which an hK2-specific oligonucleotide, effective to amplify the DNA to yield an amount of amplified hK2 DNA. The presence or amount of the amplified hK2 DNA is detected or determined. At least one point later in time, another sample is taken and the amount of amplified hK2 DNA detected or determined. Then the amounts of amplified hK2 DNA, obtained at least at two different time points, are compared.

Also provided is a method for pathologically staging prostate cancer in a human. The method comprises contacting an amount of DNA obtained by reverse transcription of RNA from a physiological sample obtained from the human afflicted with prostate cancer with an amount of at least two oligonucleotides, at least one of which is an hK2-specific oligonucleotide, effective to amplify the DNA to yield an amount of amplified hK2 DNA. The presence or amount of the amplified hK2 DNA is then detected or determined. The presence or amount of amplified hK2 DNA is indicative of the pathological stage of the prostate cancer. Preferably, the conditions are effective to amplify the amount of DNA obtained by reverse transcription of RNA from at least one cell containing hK2 in a sample which comprises at least about $10^7$ to about $10^9$ cells.

Another embodiment of the invention provides a method for monitoring therapeutic interventions involving hormone therapies. For example, because hK2 expression is androgen-dependent, hK2 RNA levels in peripheral blood or other bodily tissue or fluid may be used as a marker during intermittent androgen therapy, or during androgen provocative testing, wherein a patient is temporarily placed in a hyperandrogenized state to stimulate a level of hK2 production by any persistent prostate cancer cells sufficient to render them detectable. See T. K. Takayama et al., *Sem. in Oncol.*, 21, 542–553 (1994), and references cited therein, which are incorporated herein by reference. hK2 levels are preferably monitored periodically during the course of hormone therapy. It may be advantageous to also determine hK2 levels before commencement of therapy, and periodically after the conclusion of a therapeutic regimen.

Also provided is a diagnostic kit for detecting hK2 RNA in a physiological sample suspected of containing hK2 RNA. The kit comprises packaging containing (a) a known amount of a first hK2-specific oligonucleotide, wherein the oligonucleotide consists of at least about 7–50 nucleotides, and wherein the oligonucleotide has at least about 80% identity to SEQ ID NO: 4 or SEQ ID NO:33, and (b) a known amount of a second hK2-specific oligonucleotide, wherein the oligonucleotide consists of at least about 7–50 nucleotides, and wherein the oligonucleotide has at least about 80% identity to a nucleotide sequence which is complementary to SEQ ID NO:4 or SEQ ID NO:33. Thus, the invention also provides hK2-specific oligonucleotides consisting of at least about 7–50 nucleotides, wherein he oligonucleotide has at least about 80% identity to a nucleotide sequence which has at least 80% identity, or complementary, to SEQ ID NO:4 or SEQ ID NO:33. Preferred oligonucleotides useful in the practice of the invention comprise SEQ ID NO:14, SEQ ID NO:17, SEQ ID NO:18, SEQ ID NO:27 and SEQ ID NO:28.

The invention further provides an isolated, purified peptide comprising SEQ ID NO:22, a biologically active subunit thereof, or a biologically active variant thereof. The invention further provides an isolated, purified peptide comprising SEQ ID NO:26, a biologically active subunit thereof, or a biologically active variant thereof. Also provided is an isolated purified antibody or antibody preparation that specifically reacts with a protein or polypeptide which comprises the peptides of the invention described above.

As used herein, the term "biologically active subunit" of a peptide of the invention is preferably defined to mean a subunit of a peptide having SEQ ID NO:22, which has at least about 10%, preferably at least about 50%, and more preferably at least about 90%, the activity of a peptide having SEQ ID NO:22. The activity of a peptide of the invention can be measured by methods well known to the art including, but not limited to, the ability of the peptide to elicit a sequence-specific immunologic response when the peptide is administered to an organism, e.g., goat, rabbit, sheep or mice.

As used herein, the term "biologically active variant" of a peptide of the invention is preferably defined to mean a peptide which has at least about 80%, preferably at least about 90%, and more preferably at least about 95%, identity or homology to SEQ ID NO:22. Biologically active variants of the peptides of the invention have at least about 10%, preferably at least about 50%, and more preferably at least about 90%, the activity of a peptide having SEQ ID NO:22. The activity of a variant peptide of the invention can be measured by methods described hereinabove.

The invention further provides a method for detecting or determining the presence of metastatic prostate cancer in a human non-prostate tissue sample. The method comprises mixing an amount of an agent, which binds to an hK2 polypeptide and which does not bind to hK3, with the cells of the mammalian tissue sample so as to form a binary complex comprising the agent and the cells. The presence or amount of complex formation in the sample is then detected or determined. The presence or amount of the complex provides an indication of the presence of micrometastatic prostate cancer. As used herein, "micrometastatic" means locally invasive disease, which typically involves penetration of the prostate capsule or seminal vesicle, or occult disease. A preferred agent for use in the method is an antibody. The term "antibody" includes human and animal mAbs, and preparations of polyclonal antibodies, as well as antibody fragments, synthetic antibodies, including recombinant antibodies, chimeric antibodies, including humanized antibodies, anti-idiotopic antibodies and derivatives thereof. To prepare antibodies which bind to hK2 and not to hK3, isolated hK2 polypeptides, isolated hK2 peptides, as well as variants and subunits thereof, can be used to prepare populations of antibodies. These antibodies in turn can be used as the basis for direct or competitive assays to detect and quantify hK2 polypeptides (or "protein") in samples derived from tissues such as bone marrow and lymph nodes, and samples of cells such as from physiological fluids which comprise cells.

BRIEF DESCRIPTION OF THE FIGURES

FIG. 1 depicts the amino acid sequences of wild type mature hK2 (SEQ ID NO:1) and hK3 (SEQ ID NO:7).

FIG. 2 depicts the amino acid sequence, and corresponding nucleic acid sequence, of wild type pphK2 (SEQ ID NO:3 and SEQ ID NO:4, respectively), phK2 (SEQ ID NO:5 and SEQ ID NO:6) and hK2 (SEQ ID NO: 1 and SEQ ID NO:2). Codon 217 (GCT, Ala) is shown in bold and underlined.

FIG. 8 depicts Western blot analysis of seminal fluid using monoclonal antibody (mAb) hK1G 586.1. Processed seminal fluid was diluted 1:1 in PBS and centrifuged at 10,000×g for 20 minutes. The supernatant was subjected to SDS/PAGE on a 8–25% gel using the PHASTSYSTEM (Pharmacia). Protein was transferred to nitrocellulose and incubated with protein-G purified HK1G 586.1 (1 μg/ml) followed by goat anti-mouse IgG-HRP (1:1000). The blot was developed using the ECL detection system (Amersham).

FIG. 11 is a plot of hK2 expression and cell viability over time. AV12-hK2 clone #27 was grown to 60–70% confluency, washed with HBSS and serum free HH4 media was added. Spent media was withdrawn each day and the hK2 concentration was measured by ELISA using HK1D. 106.4 or HK1G 464.3 as a primary antibody, and goat anti-mouse IgG-HRP as a secondary antibody. The reaction was developed with OPD (Sigma, St. Louis, Mo.). Viable cells were enumerated daily using trypan blue dye exclusion.

Figure 12:
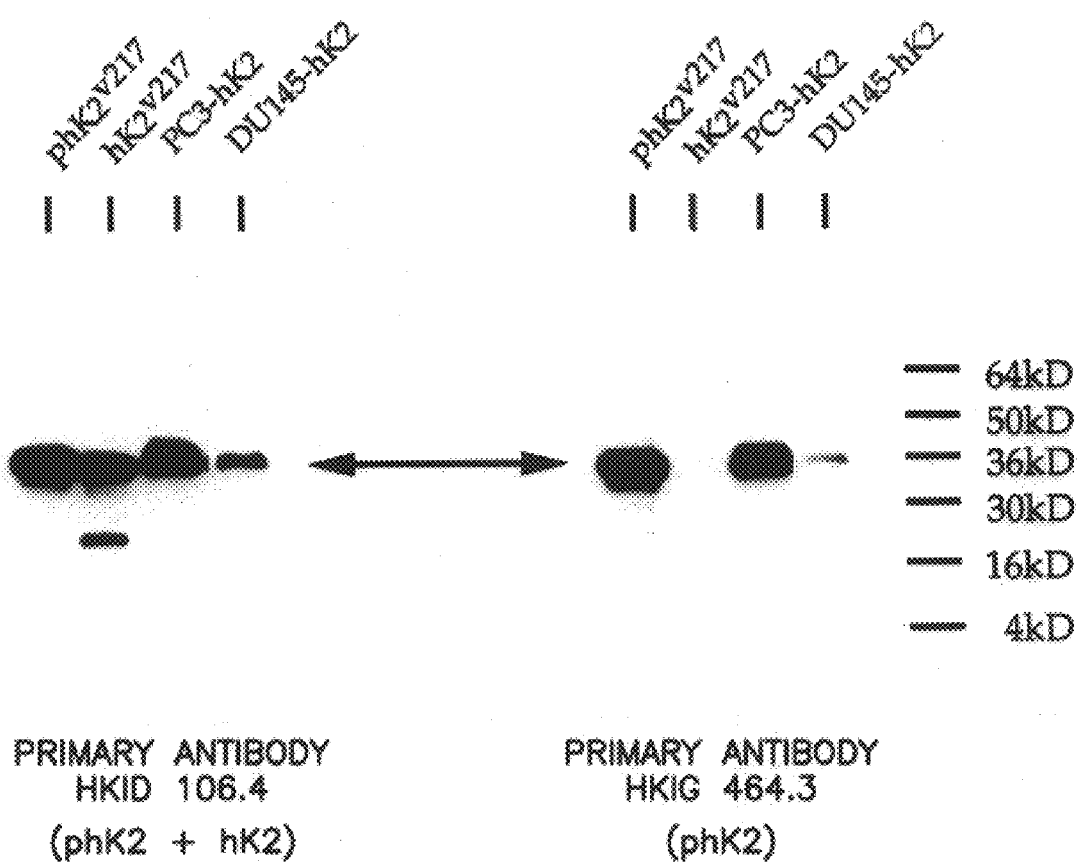

FIG. 12 depicts the expression of hK2 in PC3 and DU145 cells. PC3 and DU145 cells transfected with pGThK2 were grown to ~60–70% confluency, washed and resuspended in serum free HH4 media. The spent medium of pGThK2 transfected DU145 cells was collected 3 days after resuspension and the spent medium of pGThK2 transfected PC3 cells was collected 5 days after resuspension. Spent media were concentrated and subjected to SDS/PAGE on 12% gels. Proteins were electroblotted and probed with HK1D 106.4 or HK1G 464.3 as described above. Purified pK2$^{v217}$ and phK2$^{v217}$ were used as controls. The position of hK2 is indicated by an arrow.

Figure 13:
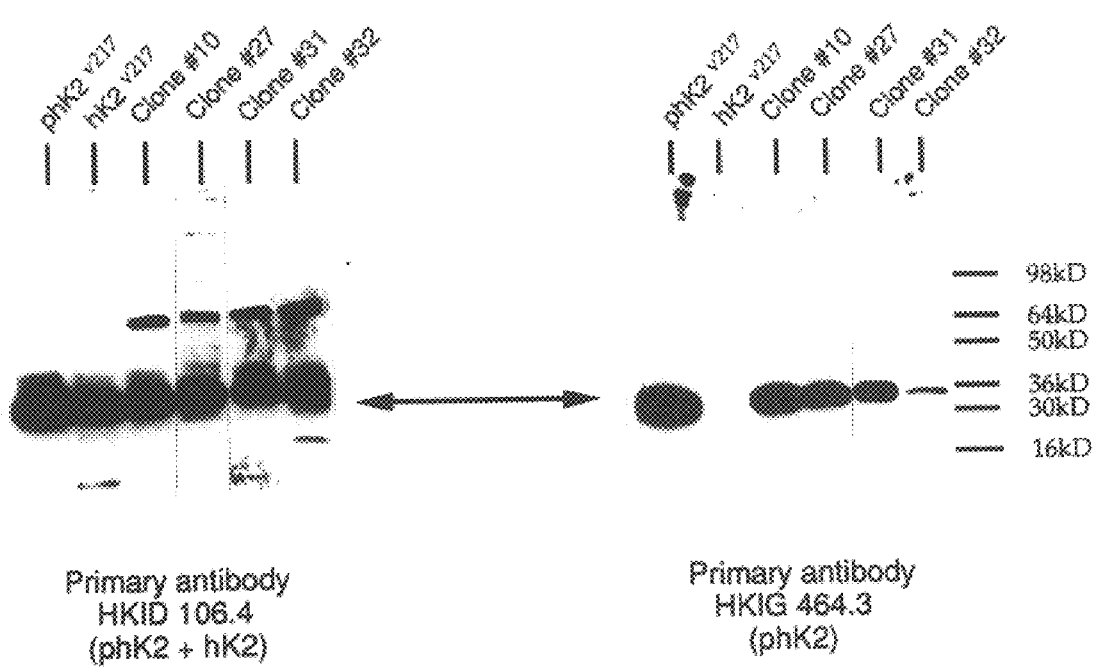

FIG. 13 depicts the expression of hK2 by selected hK2-containing AV12 clones. Cells from hK2 containing AV12 clone numbers 10, 27, 31 and 32 were grown to ~60–70% confluency and washed with HBSS, then serum free HH4 media was added. Spent media was withdrawn 7 days after the addition of serum free media, concentrated and subjected to SDS/PAGE on a 12% gel. Proteins were electroblotted and probed with HK1D 106.4 or HK1G 464.3. Goat anti-mouse IgG-HRP (1:500) was used as a secondary antibody and the blot was developed with ECL (Amersham) according to manufacturer's instructions. Purified phK2$^{v217}$ and hK2$^{v217}$ were used as controls. The position of hK2 is indicated by an arrow.

Figure 14:
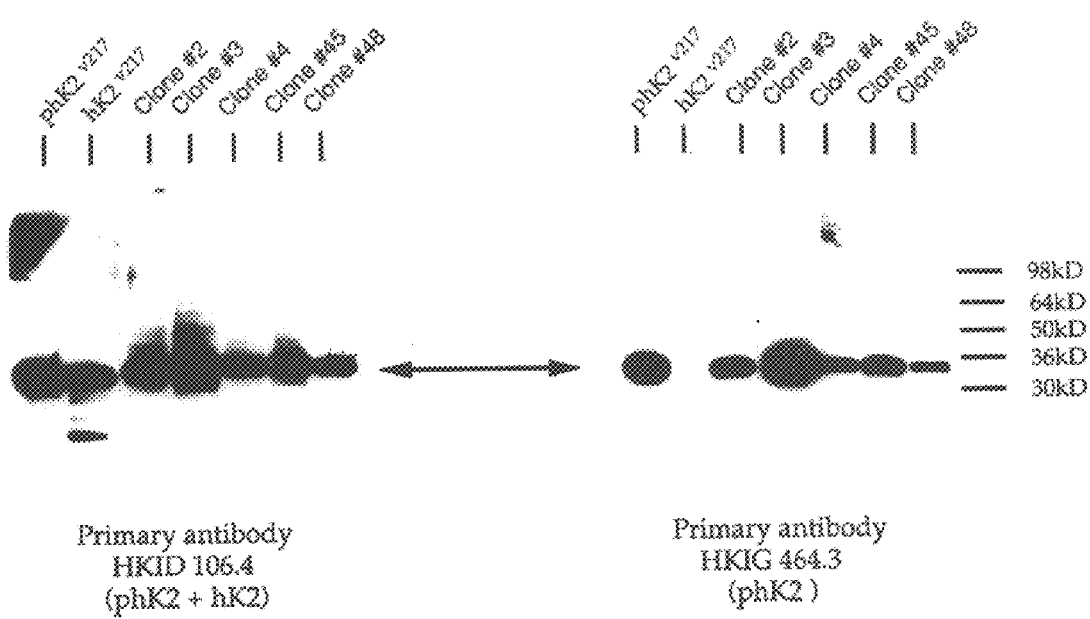

FIG. 14 depicts the expression of phK2$^{v217}$ in selected AV12-hK2$^{v217}$ clones. Cells from AV12 clone numbers 2, 3, 4, 45 and 48 were grown to approximately 60–70% confluency and washed with HBSS, and serum free HH4 media was added. Spent media was withdrawn 7 days after the addition of serum free media, concentrated and subjected to SDS/PAGE on a 12% gel. Proteins were electroblotted and probed with HK1D 106.4 or HK1G 464.3. Goat anti-mouse IgG-HRP (1:500) was used as a secondary antibody and the blot was developed with ECL (Amersham) according to manufacturer's instructions. Purified phK2$^{v217}$ and hK2$^{v217}$ were used as controls. The position of hK2 is indicated by an arrow.

Figure 15:
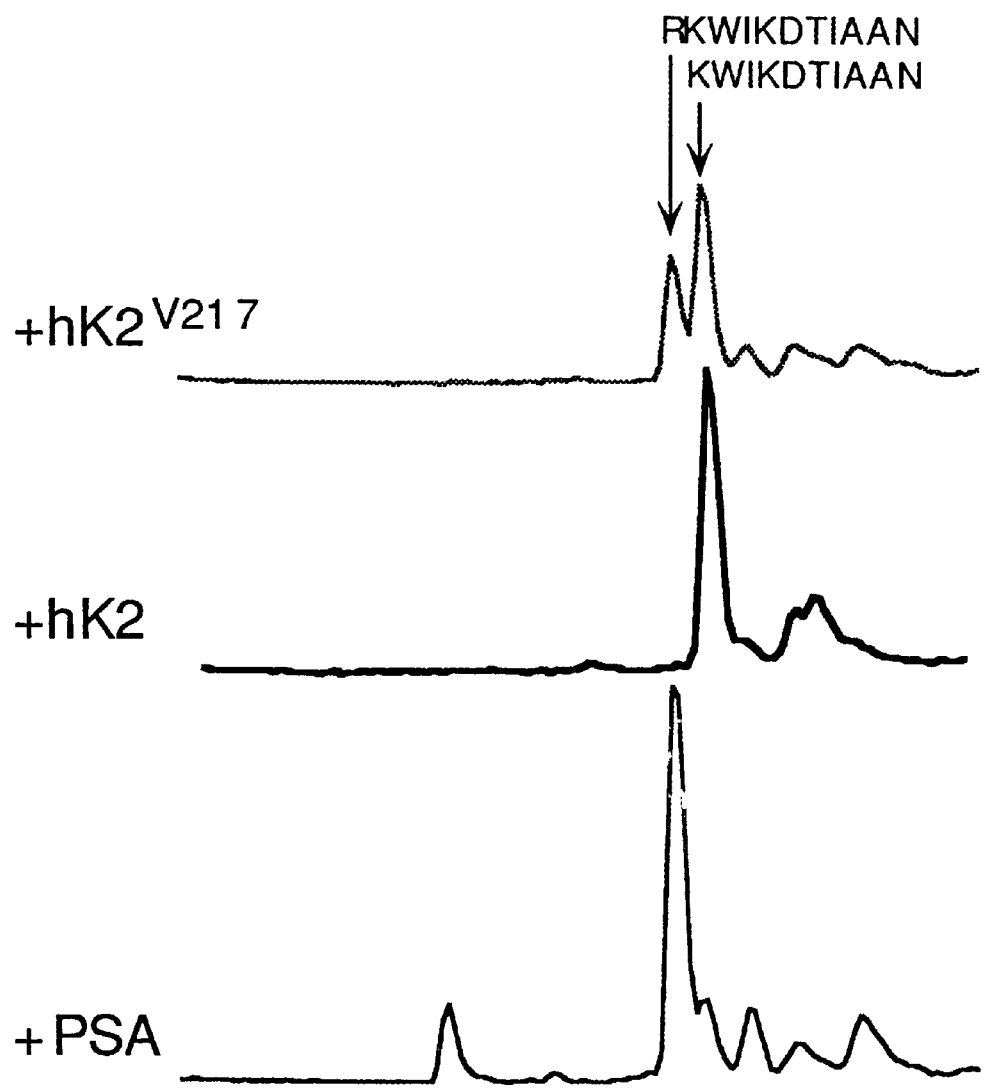

FIG. 15 depicts the amidolytic specificity of hK2$^{v217}$, hK2, and PSA for residues 210–236 of hK2. The synthetic peptide (0.63 mM) (SEQ ID NO:36) was digested overnight at 37° C. with 1 µg/ml hK2, 40 µg/ml hK2$^{v217}$ or 100 µg/ml PSA, and the digestion products separated by RP-HPLC. Peaks were normalized to compare the qualitative aspects of cleavage. RKWIKDTIAAN is SEQ ID NO:48, and KWIKDTIAAN is SEQ ID NO:49.

FIG. 16 depicts the specificity of hK2 and PSA for different peptide substrates. Open arrows denote peptide bonds cleaved by PSA; solid arrows denote bonds cleaved by hK2. Peptide #1 (SEQ ID NO:36) represents amino acid residues 210–236 of hK2. Peptide #2 (SEQ ID NO:44) represents amino acid residues 1–14 of angiotensinogen, i.e., the renin substrate tetradecapeptide. Peptide #3 (SEQ ID NO:45) represents amino acid residues ~7 to +7 of phK2. Peptide #4 (SEQ ID NO:20) represents amino acid residues 41–56 of hK2. Peptide #5 (SEQ ID NO:46) represents the amino acid sequence of the oxidized beta chain of insulin. Peptide #6 (SEQ ID NO:47) represents amino acid residues 196–213 of PMSA.

FIG. 17 depicts the activation of phK2$^{v217}$ by hK2 but not hK2$^{v217}$. phK2$^{v217}$ contains the pro leader peptide sequence VPLIQSR (SEQ ID NO:37), a sequence not present in hK2$^{v217}$ Panel A shows phK2$^{v217}$ incubated with 1% w/w hK2. Panel B is a control with 40% w/w hK2$^{v217}$ incubated with phK2$^{v217}$ for 6 hours.

Figure 18:
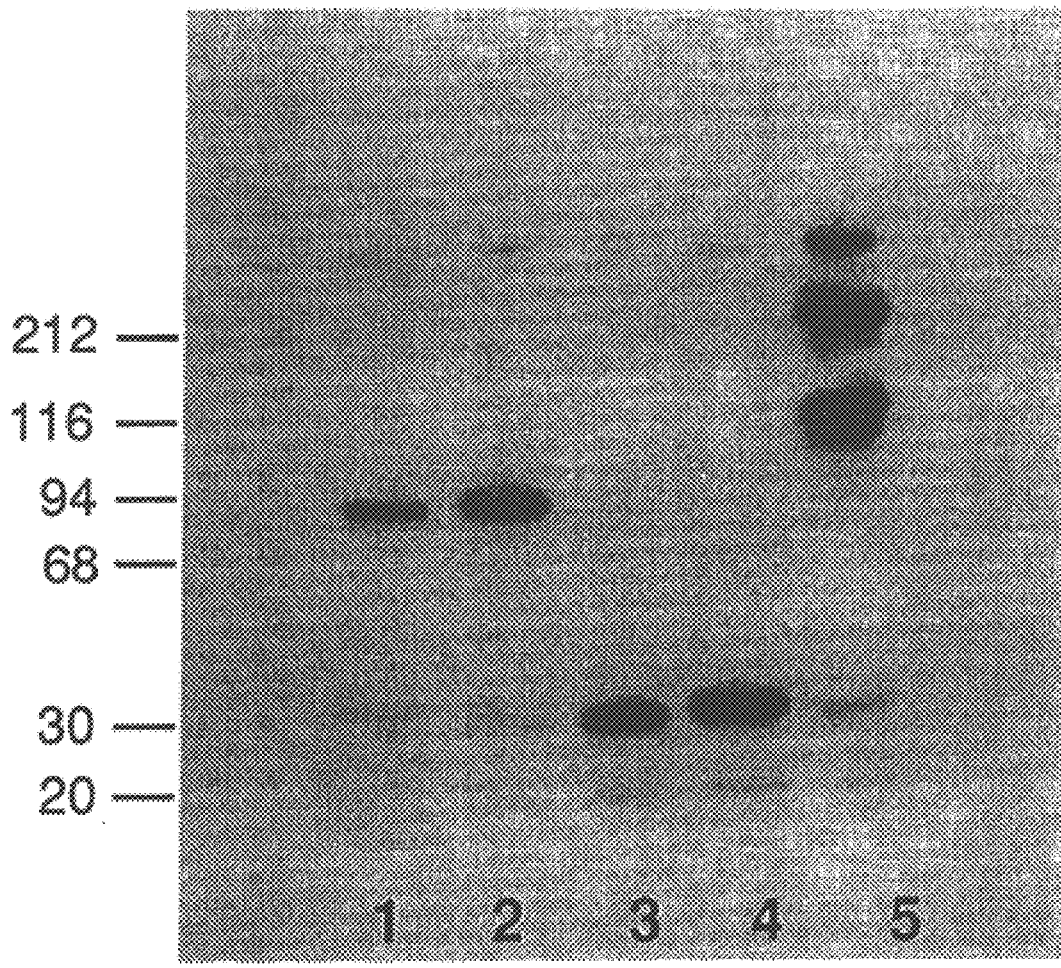

FIG. 18 depicts Western blot analysis of hK2 incubated with protease inhibitors. Each sample was separated on a 8–25% gradient SDS-PAGE, blotted and probed with HK1G586.1. hK2 was incubated for 4 hours at 37° C. with the following inhibitors: Lane 1, antichymotrypsin (ACT); lane 2, alpha 2-antiplasmin; lane 3, antithrombin III; lane 4, alpha 1-protease inhibitor (anti-trypsin); lane 5, alpha 2-macroglobulin; lanes 1 and 2 show a covalent complex of the predicted Mr of 90–100 kD. Serpin inhibitors were employed at 20 µM, macroglobulin at 2.8 µM, and hK2 at 0.175 uM. Lane 5 shows the higher Mr complexes representing covalent complex formation of hK2 with alpha 2-macroglobulin.

Figure 19:
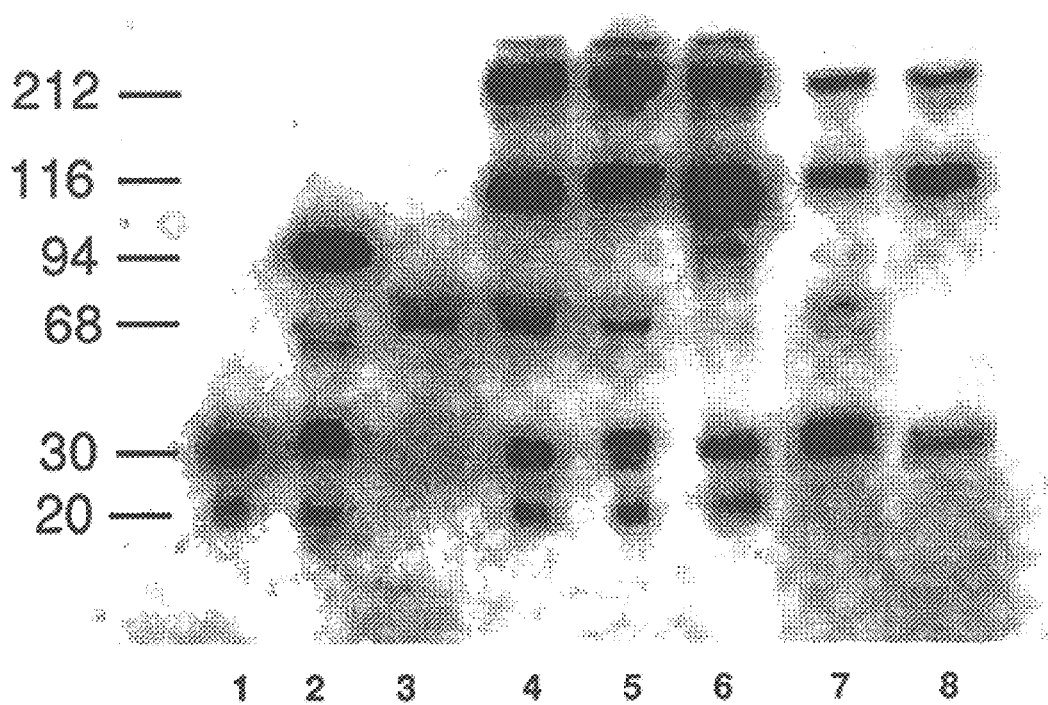

FIG. 19 depicts complex formation of hK2 in human serum. Western blots of hK2 and PSA were incubated with human serum. hK2 samples were probed with HK1G586.1 and PSA samples with PSM773 anti-PSA mAb Lanes 1–6 contain hK2 samples and lanes 7 and 8 are PSA samples. Lane 1 represents an hK2 control. Lane 2 contains hK2 incubated with ACT for 4 hours. Lane 3 represents a serum control with no added protease. Lane 4 contains hK2 incubated for 15 minutes with serum. Lane 5 contains hK2 incubated with serum for 4 hours. Lane 6 contains hK2 incubated with purified alpha-2 macroglobulin for 4 hours. Lane 7 contains PSA incubated with serum for 4 hours. Lane 8 contains PSA incubated with purified alpha-2 macroglobulin for 4 hours.

Figure 20:
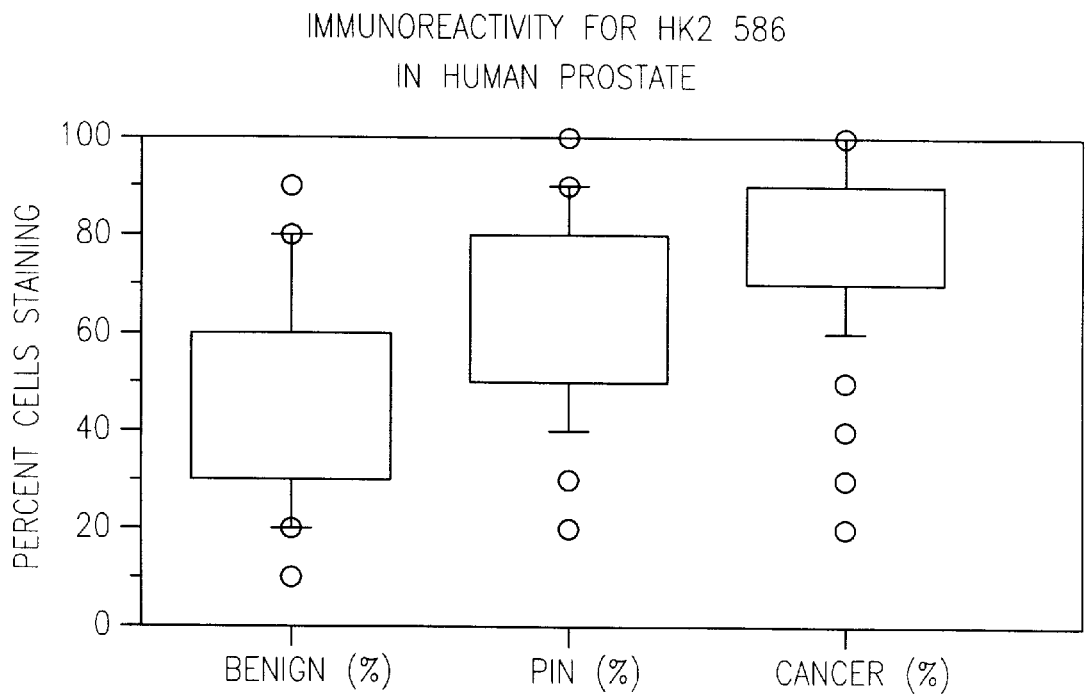

FIG. 20 depicts immunoreactivity of monoclonal antibody HK1G 586 in untreated human prostate (n=257).

Figure 21:
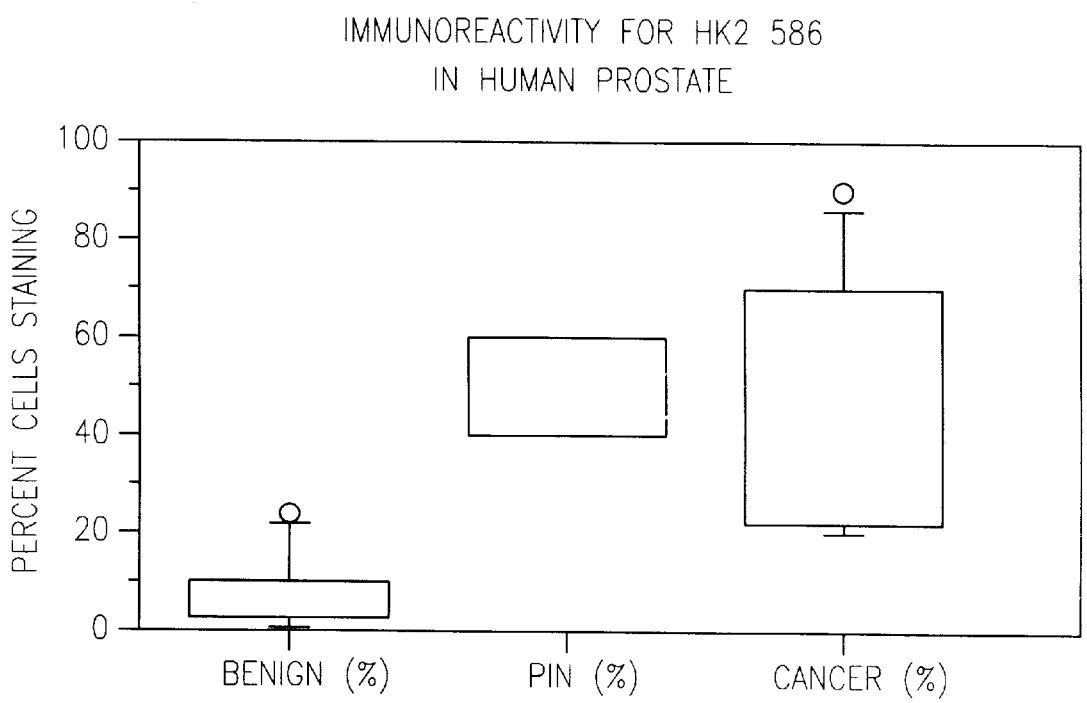

FIG. 21 depicts immunoreactivity of monoclonal antibody HK1G 586 in androgen deprivation therapy-treated human prostate (n=7).

Figure 22A:
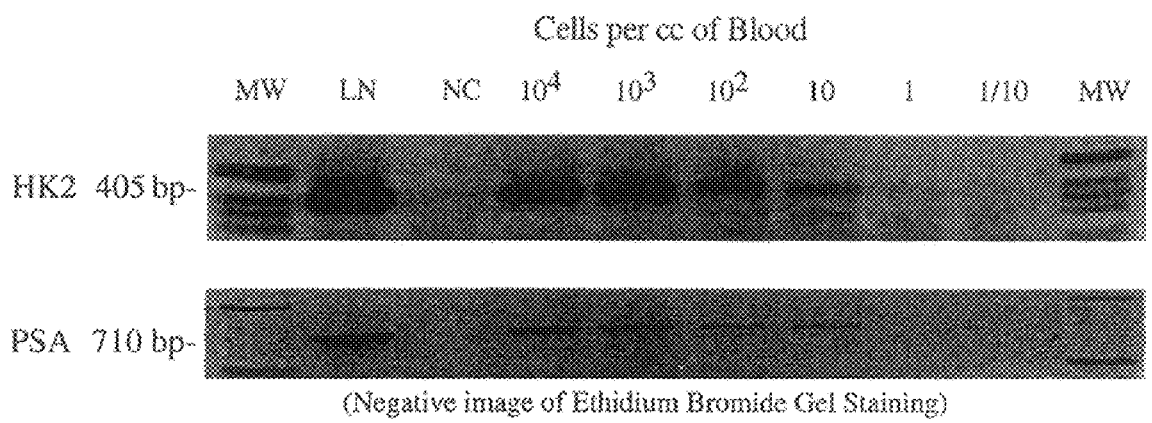
Figure 22B:
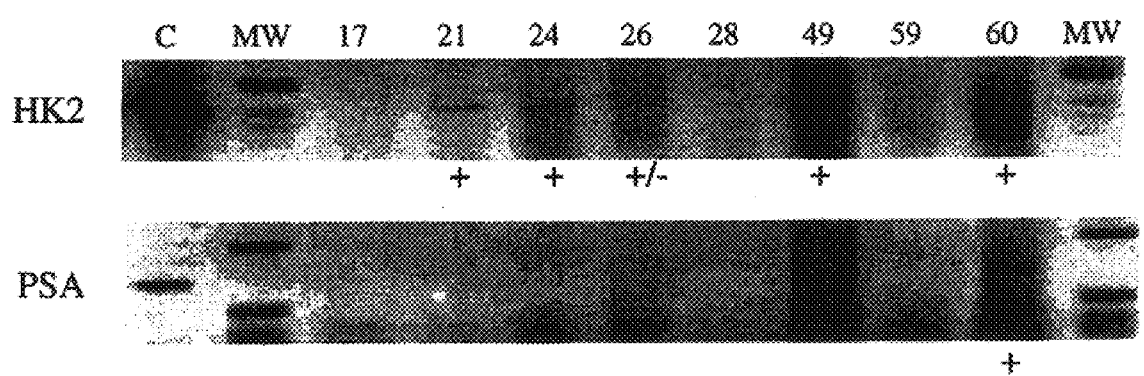

FIG. 22 depicts (A) RT-PCR detection of PSA and hK2 mRNAs in RNA extracted from LNCaP cells diluted in whole human blood, and (B) RT-PCR detection of PSA and hK2 mRNAs in RNA extracted from whole human blood of the following patients: patient 17, age 31, male control; patient 21, age 58, clinical stage B; patient 24, age 83, known metastatic disease (D2); patient 26, age 75, pathological stage C (+margins); patient 28, age 57, pathological stage C (+margins); patient 49, age 64, pathological stage C (+seminal vesicles); patient 59, age 31, male control; patient 60, age 73, known metastatic disease.

Figure 23:
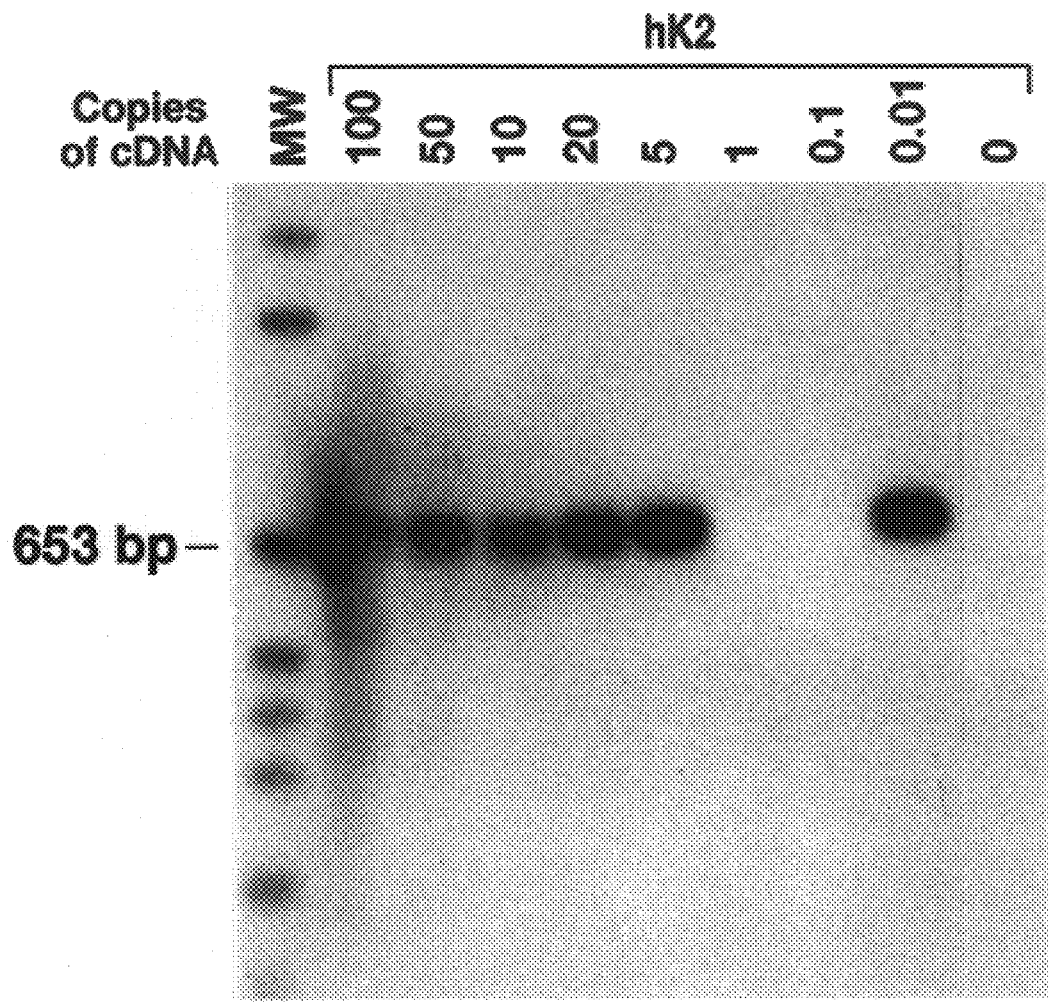

FIG. 23 shows PCR detection of serial dilutions of hK2 cDNA with hK2-3 (SEQ ID NO:27) and hK2-4 (SEQ ID NO:28).

Figure 24:
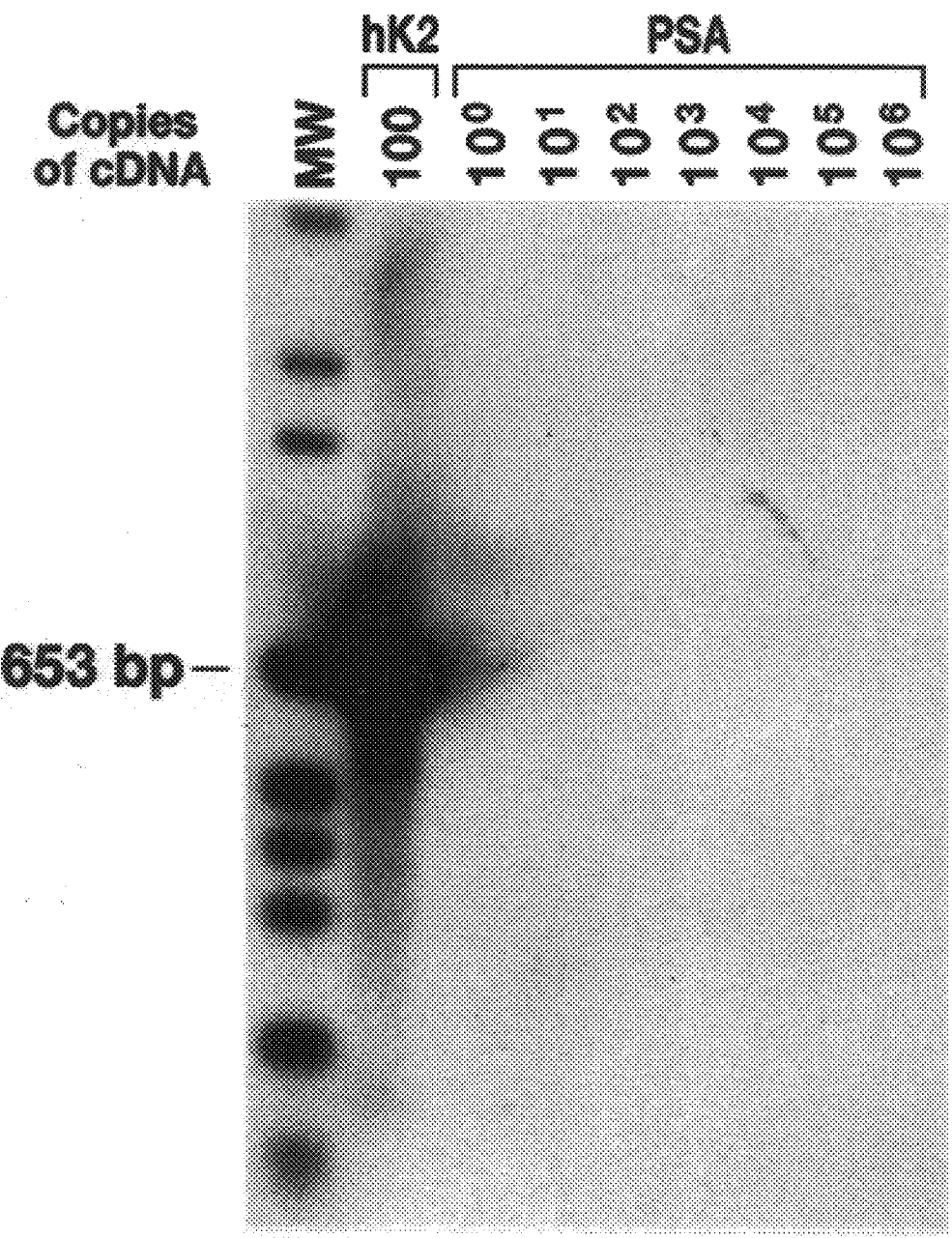

FIGS. 24 shows PCR detection of serial dilutions of PSA cDNA with hK2-3 (SEQ ID NO:27) and hK2-4 (SEQ ID NO:28).

FIG. 25 shows a comparison of (A) the sequence of an hK2-specific sense primer (SEQ ID NO:27) to the corresponding sequence in hK3 (SEQ ID NO:29) and hK1 (SEQ ID NO:31), and a comparison of (B) the sequence of an hK2-specific antisense primer (SEQ ID NO:28) to the corresponding sequence in hK3 (SEQ ID NO:30) and hK1 (SEQ ID NO:32).

Figure 26:
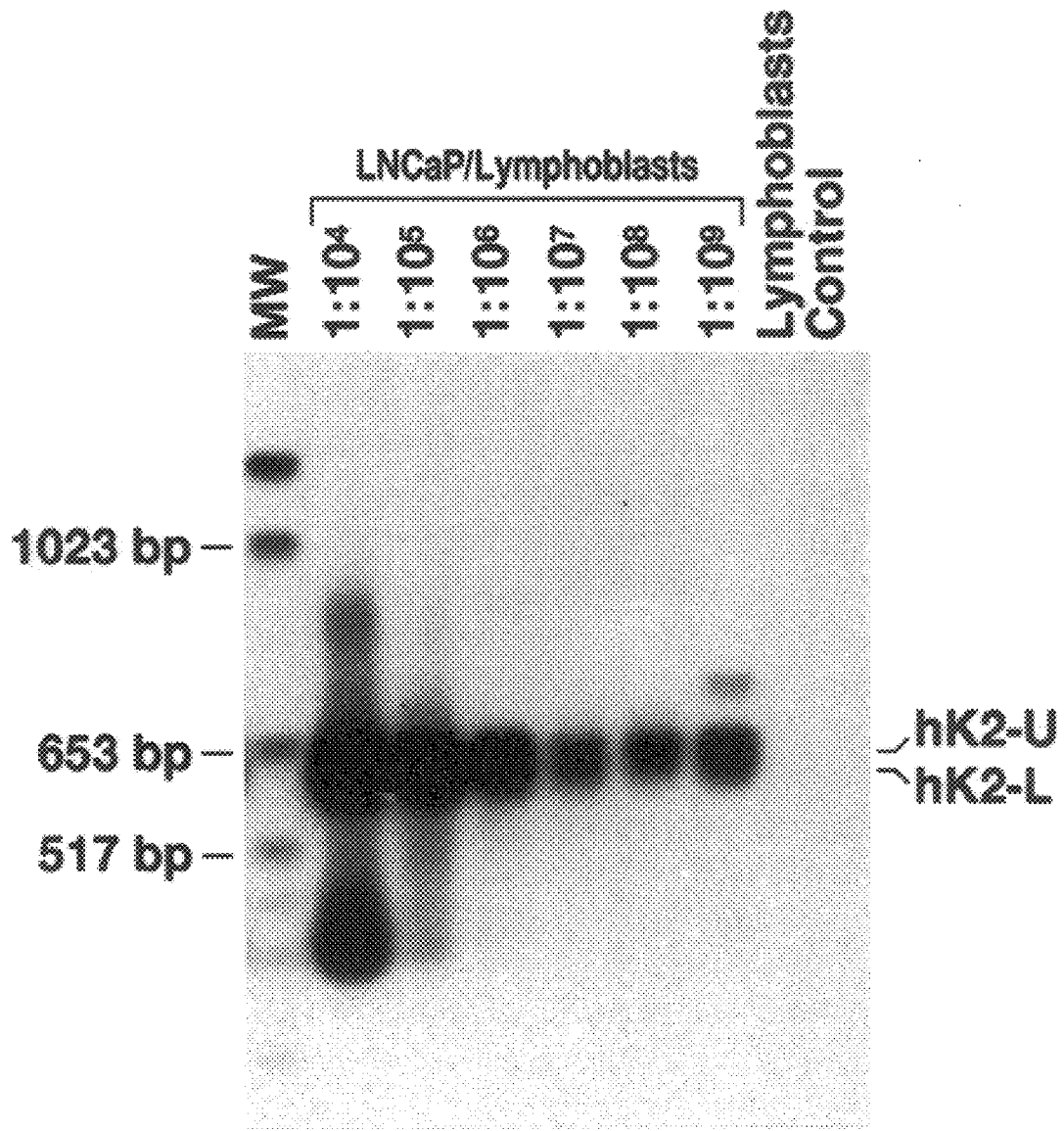

FIG. 26 depicts the RT-PCR detection of hK2 RNA extracted from serial dilutions of LNCaP cells in lymphoblasts.

Figure 27:
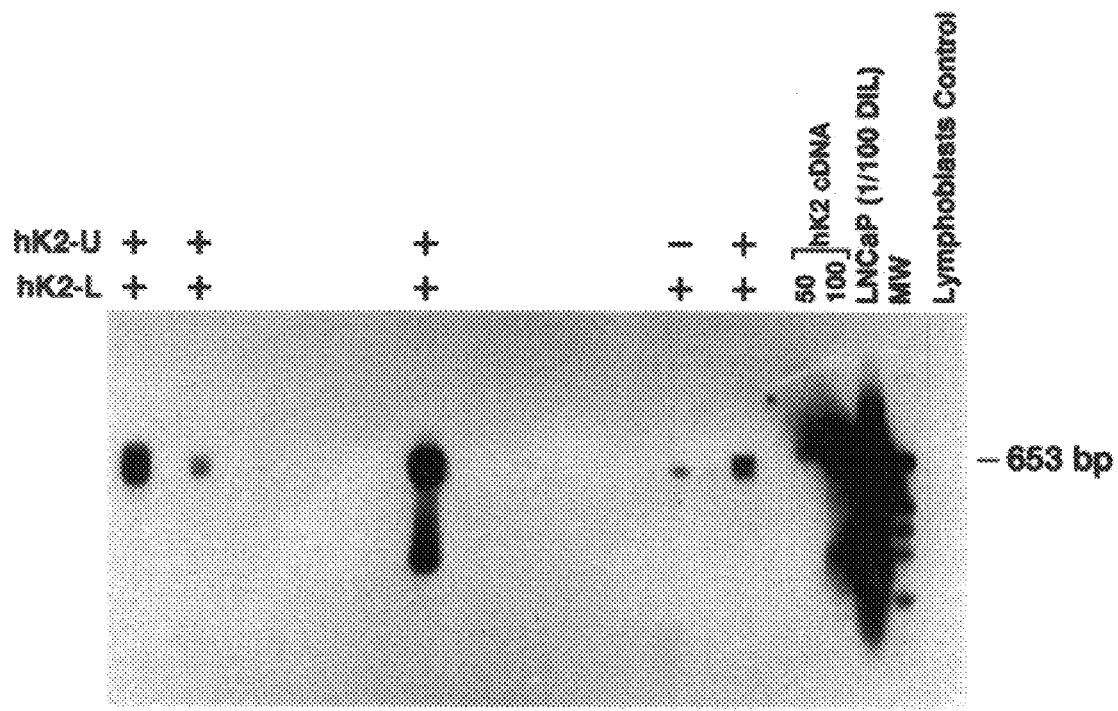

FIG. 27 shows the RT-PCR detection of hK2 RNA in peripheral blood from patients with clinically localized prostate cancer.

Figure 28:
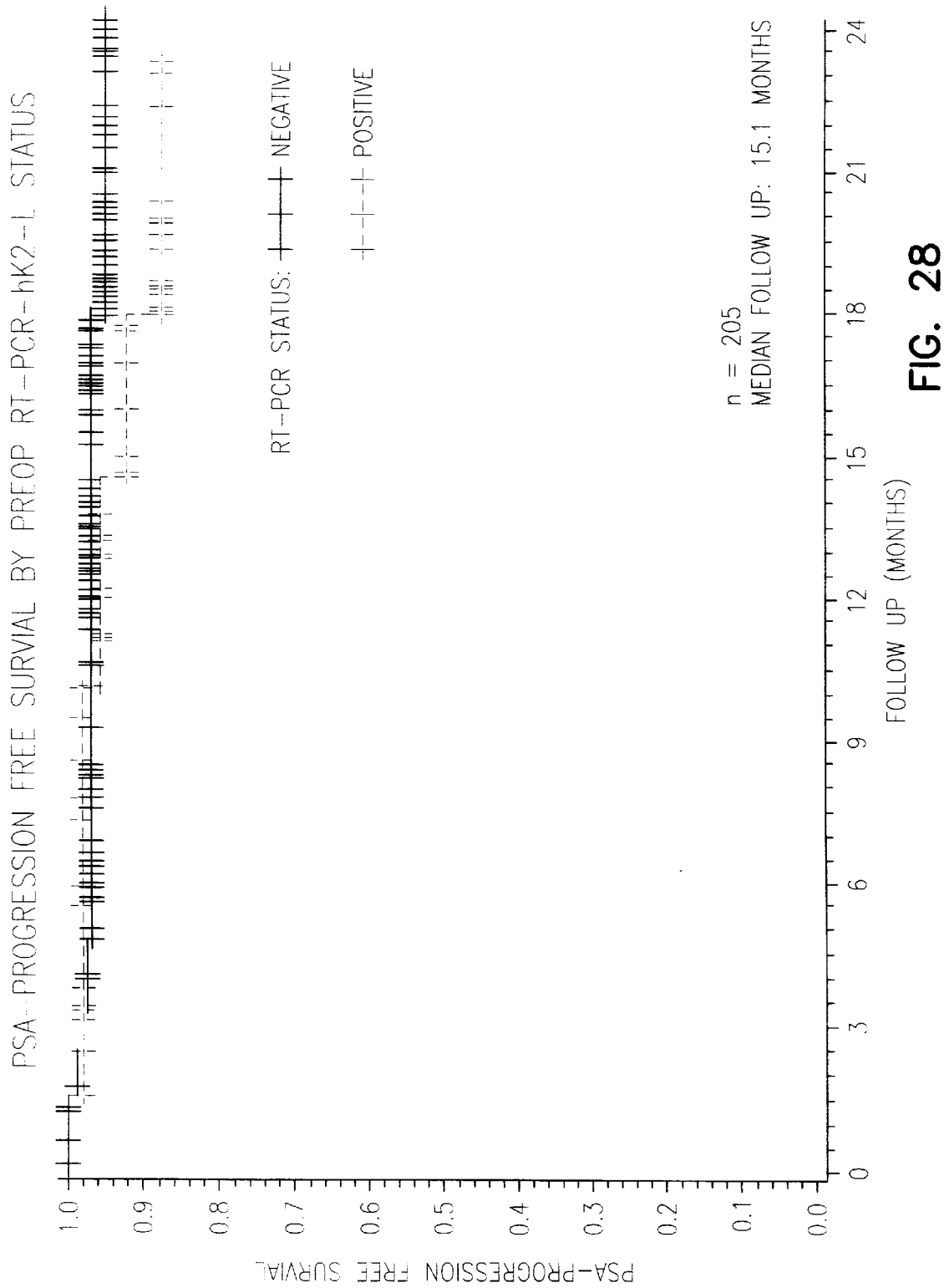

FIG. 28 shows a graph of PSA-progression free patient survival versus time post-radical prostatectomy. Lower curve corresponds to hK2 RT-PCR+ patients. upper curve corresponds to hK2 RT-PCR− patients

DETAILED DESCRIPTION OF THE INVENTION

The high degree of amino acid sequence homology of hK2 to PSA, and the fact that the expression of both hK2 and PSA is essentially limited to prostate cells, suggests that measuring the amount or presence of hK2 and PSA in tissue samples, or measuring the levels of hK2 transcripts in physiological fluids comprising cells, e.g., blood, or in tissue samples, e.g., lymph node, can be useful in the diagnosis and monitoring of prostatic cancer (pCa).

Definitions

As used herein, the term "hK2 polypeptide" includes recombinant pre-pro, pro and mature hK2 polypeptides. A mature hK2 polypeptide having the amino acid sequence shown in FIG. 1 (SEQ ID NO:1), as well as "variant" polypeptides which share at least 90% homology with SEQ ID NO:1 in the regions which are substantially homologous with hK3, i.e., which regions are not identified by bars as shown in FIG. 1. The variant hK2 polypeptides of the invention have at least one amino acid substitution relative to the corresponding wild type hK2 polypeptide. A preferred variant hK2 polypeptide comprises SEQ ID NO:8, i.e., a mature hK2 polypeptide having an alanine to valine substitution at amino acid position 217. hK2 polypeptides possess antigenic function in common with the mature hK2 molecule of FIG. 1, in that said polypeptides are also definable by antibodies which bind specifically thereto, but which do not cross-react with hK3 (or hK1). Preferably, said antibodies react with antigenic sites or epitopes that are also present on the mature hK2 molecule of FIG. 1.

Antibodies useful to define common antigenic function are described in detail in Ser. No. 08/096,946, now U.S. Pat. No. 5,516,639, i.e., polyclonal antisera prepared in vivo against hK2 subunit 41–56.

"Isolated hK2 nucleic acid" is RNA or DNA containing greater than 7, preferably 15, and more preferably 20 or more, sequential nucleotide bases that are complementary to the non-coding or coding strand, e.g., SEQ ID NO:33 corresponds to the coding strand of genomic hK2, of the native hK2 polypeptide RNA or DNA, or hybridizes to said RNA or DNA and remains stably bound under stringent conditions. Preferably, the isolated nucleic acid encodes a biologically active hK2 polypeptide, a variant thereof, or a subunit thereof The biological activity of an hK2 polypeptide can be detected by methods well known to the art including, but not limited to, the ability to react with antibodies specific for hK2 polypeptides, the ability to cleave hK2-specific substrates (see Example 7), or the ability to bind to serum proteins (see Example 9). A variant hK2 polypeptide or subunit thereof, or a subunit of an hK2 polypeptide, has at least about 10%, preferably at least about 50%, and more preferably at least about 90%, the biological activity of an hK2 polypeptide comprising the amino acid sequence of SEQ ID NO:1.

Thus, the RNA or DNA is isolated in that it is free from at least one contaminating nucleic acid with which it is normally associated in the natural source of the nucleic acid and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated hK2 nucleic acid is RNA or DNA that encodes a biologically active hK2 polypeptide sharing at least 90% sequence identity with the hK3-homologous regions of the hK2 peptide of FIG. 1, as described above. The term "isolated, purified" as used with respect to an hK2 polypeptide is defined in terms of the methodologies discussed hereinbelow.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, and later introduced into target host cells, such as cells derived from animal, plant, insect, yeast, fungal or bacterial sources. An example of recombinant DNA "derived" from a source, would be a DNA sequence that is identified as a useful fragment encoding hK2, or a fragment or variant thereof, and which is then chemically synthesized in essentially pure form. An example of such DNA "isolated" from a source would be a useful DNA sequence that is excised or removed from said source by chemical means, e.g, by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed, or not highly expressed.

As used herein, "chimeric" means that a vector comprises DNA from at least two different species, or comprises DNA from the same species, which is linked or associated in a manner which does not occur in the "native" or wild type of the species.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}$P, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS. See Sambrook et al., supra, for other examples of stringent conditions.

Expression Cassettes or Expression Vectors

An expression cassette or vector comprising a recombinant DNA sequence encoding hK2 which is operably linked to a promoter functional in a host cell, may be circular or linear, double-stranded or single-stranded. Generally, the expression cassette or vector is in the form of chimeric DNA, such as plasmid DNA, that can also contain coding regions flanked by control sequences which promote the expression of the recombinant DNA present in the resultant cell line. For example, the expression cassette may itself comprise a promoter that is active in mammalian cells, or may utilize a promoter already present in the genome that is the transformation target. Such promoters include the CMV promoter, as well as the SV40 late promoter and retroviral LTRs (long terminal repeat elements). Aside from recombinant DNA sequences that serve as transcription units for hK2 or portions thereof, a portion of the recombinant DNA may be untranscribed, serving a regulatory or a structural function.

The expression cassettes or expression vectors to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA and the like. See also Table 1 of Lundquist et al. (U.S. Pat. No. 5,554,798).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

Transformation of Host Cells and Recovery of Recombinant hK2 Polypeptides

The expression cassette or vector comprising the recombinant DNA encoding an hK2 polypeptide can be readily introduced into the target cells by transfection for example, by the modified calcium phosphate precipitation procedure of C. Chen et al., *Mol. Cell. Biol.*, 7, 2745 (1987). Transfection can also be accomplished by lipofectin, using commercially available kits, e.g., provided by BRL.

Suitable host cells for the expression of hK2 polypeptide are derived from multicellular organisms. Such host cells are capable of complex processing and glycosylation activities. In principle, any higher eukaryotic cell culture can be employed in the practice of the invention, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6, 47 (1988); Miller et al., in *Genetic Engineering*, J. K. Setlow et al., eds., Vol. 8 (Plenum Publishing, 1986), pp. 277–279; and Maeda et al., *Nature*, 315, 592 (1985). A variety of viral strains for transfection are publicly available, e.g., the L-1 variant of *Autographa californica* NPV and the Bm-5 strain of *Bombyx mori* NPV, and such viruses may be used, preferably for transfection of *Spodoptera frugiperda* cells.

When hK2 polypeptide is expressed in a recombinant cell other than one of human origin, the hK2 polypeptide is completely free of proteins or polypeptides of human origin. However, it is necessary to purify hK2 polypeptide from recombinant cell proteins or polypeptides to obtain preparations that are substantially homogeneous as to hK2 polypeptide. For example, the culture medium or lysate can be centrifuged to remove particulate cell debris. The membrane and soluble protein fractions are then separated. The hK2 polypeptide may then be purified from the soluble protein fraction and, if necessary, from the membrane fraction of the culture lysate. hK2 polypeptide can then be purified from contaminant soluble proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration Lising, for example, SEPHADEX G-75; or ligand affinity chromatography.

Once isolated from the resulting transgenic host cells, derivatives and variants of the hK2 polypeptide can be readily prepared. For example, amides of the hK2 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the hK2 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal hK2 amino acid sequence of FIG. 1 can be modified by substituting one or two conservative amino acid substitutions for the positions specified, including substitutions which utilize the D rather than L form.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

Variant hK2 Polypeptides

It is envisioned that variant hK2 polypeptides have at least one amino acid substitution relative to SEQ ID NO:1, SEQ ID NO:3 or SEQ ID NO:5, e.g., SEQ ID NO:8 has an alanine to valine substitution at position 217 relative to SEQ ID NO:1. In particular, amino acids are substituted in a relatively conservative manner. Such conservative substitutions are shown in Table 1 under the heading of exemplary substitutions. More preferred substitutions are under the heading of preferred substitutions. After the substitutions are introduced, the products are screened for biological activity, e.g., ability to generate hK2-specific antibodies or to specifically react with hK2-specific antibodies, i.e., antibodies that bind to hK2 and not to hK3 (PSA).

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Naturally occurring residues are divided into groups based on common side-chain properties:
 (1) hydrophobic: norleucine, met, ala, val, leu, ile;
 (2) neutral hydrophilic: cys, ser, thr;
 (3) acidic: asp, glu;
 (4) basic: asn, gln, his, lys, arg;
 (5) residues that influence chain orientation: gly, pro; and
 (6) aromatic; trp, tyr, phe.

The invention also envisions hK2 variants with non-conservative substitutions. Non-conservative substitutions entail exchanging a member of one of the classes described above for another. Amino acid substitutions are introduced into the DNA molecules of the invention by methods well known to the art.

Uses of Recombinant hK2 Polypeptides

Once isolated, hK2 polypeptide and its antigenically active variants, derivatives and fragments thereof can be used in assays for hK2 in samples derived from biological materials suspected of containing hK2 or anti-hK2 antibodies, as disclosed in detail in U.S. Pat. No. 5,516,639. For example, the hK2 polypeptide can be labeled with a detectable label, such as via one or more radiolabeled peptidyl residues, and can be used to compete with endogenous hK2 for binding to anti-hK2 antibodies, i.e., as a "capture antigen" to bind to anti-hK2 antibodies in a sample of a physiological fluid, via various competitive immunoassay format for hK2 which uses anti-hK2 antibodies which are capable of immobilization is carried out by:
 (a) providing an amount of anti-hK2 antibodies which are capable of attachment to a solid surface;
 (b) mixing a physiological sample, which comprises hK2, with a known amount of hK2 polypeptide which comprises a detectable label, to produce a mixed sample;
 (c) contacting said antibodies with said mixed sample for a sufficient time to allow immunological reactions to occur between said antibodies and said hK2 to form an antibody-hK2 complex, and between said antibodies and said labeled polypeptide to form an antibody-labeled polypeptide complex;

(d) separating the antibodies which are bound to hK2 and antibodies bound to the labeled polypeptide from the mixed sample;

(e) detecting or determining the presence or amount of labeled polypeptide either bound to the antibodies on the solid surface or remaining in the mixed sample; and (f) determining from the result in step (e) the presence or amount of said hK2 in said sample.

In another format which can detect endogenous hK2 in a sample by a competitive inhibition immunoassay, a known amount of anti-hK2 antibody is added to a sample containing an unknown amount of endogenous hK2. The known amount is selected to be less than the amount required to complex all of the hK2 suspected to be present, e.g., that would be present in a sample of the same amount of sample material obtained from a patient known to be afflicted with prostate cancer. Next, a known amount of the hK2 polypeptide of the invention or a subunit thereof, comprising a detectable label is added. If endogenous hK2 is present in the sample, fewer antibodies will be available to bind the labeled hK2 polypeptide, and it will remain free in solution. If no endogenous hK2 is present, the added labeled polypeptide will complex with the added anti-hK2 antibodies to form binary complexes. Next, the binary antibody-antigen complexes are precipitated by an anti-mammal IgG antibody (sheep, goat, mouse, etc.). The amount of radioactivity or other label in the precipitate (a ternary complex) is inversely proportional to the amount of endogenous hK2 that is present in the sample, e.g., a pellet containing reduced amounts of radioactivity is indicative of the presence of endogenous hK2.

Alternatively to the conventional techniques for preparing polyclonal antibodies or antisera in laboratory and farm animals, monoclonal antibodies against hK2 polypeptide can be prepared using known hybridoma cell culture techniques. In general, this method involves prepared an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the f(ab) fragment, as are partially humanized monoclonal antibodies.

Chimeric and Modified Antibodies

Chimeric antibodies comprise the fusion of the variable domains from one immunoglobulin to the constant domains from another immunoglobulin. Usually, the variable domains are derived from an immunoglobulin gene from a different species, perhaps a human. This technology is well known to the art. See, for example, European Patent Applications, EP-A-0 125,023 (Cabilly/Genetech) and EP-A-0 120,694 and U.S. Pat. No. 4,816,567, the disclosures of which are incorporated by reference herein, which disclose the preparation of variations of immunoglobulin-type molecules using recombinant DNA technology.

Another approach to prepare chimeric or modified antibodies is to attach the variable region of a monoclonal antibody to another non-immunoglobulin molecule, to produce a derivative chimeric molecule (see WO 86/01533, Neuberger and Rabbits/Celltech, herein incorporated by reference). A further approach is to prepare a chimeric immunoglobulin having different specificities in its different variable regions (see EP 68763A). Yet another approach is to introduce a mutation in the DNA encoding the monoclonal antibody, so as to alter certain of its characteristics without changing its essential specificity. This can be accomplished by site-directed mutagenesis or other techniques known in the art.

The Winter patent application EP-A-0 239 400 (herein incorporated by reference) discloses the preparation of an altered, derivative antibody by replacing the complementarity determining regions (CDRs) of a variable region of an immunoglobulin with the CDRs from an immunoglobulin of different specificity, using recombinant DNA techniques ("CDR-grafting"). Thus, CDR-grafting enables "humanization" of antibodies, in combination with the alteration of the framework regions.

Human antibodies can also be prepared by reconstituting the human immune system in mice lacking their native immune system, then immunizing the mice so as to yield human antibodies which are specific for the immunogen.

A "humanized" antibody containing the CDRs of a rodent antibody specific for an antigen of interest may be less likely to be recognized as foreign by the immune system of a human. It follows that a "humanized" antibody with the same binding specificity, as e.g., HK1G464, may be of particular use in human therapy and/or diagnostic methods.

The manipulation and/or alteration of any given antibody, or gene(s) encoding for the same, to generate a derivative antibody is well known to the art.

Detection of hK2-Specific Transcripts by Reverse Transcriptase-Polymerase Chain Reaction (RT-PCR)

To detect hK2 encoding RNA transcripts, RNA is isolated from a cellular sample suspected of containing hK2 RNA, e.g., total RNA isolated from human prostate tissue or peripheral blood. RNA can be isolated by methods known to the art, e.g., using TRIZOL™ reagent (GIBCO-BRL/Life Technologies, Gaithersburg, Md.). Oligo-dT can be employed as a primer in a reverse transcriptase reaction to prepare first-strand cDNAs from the isolated RNA. Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, N.Y., 1989). Thus, amplification of specific nucleic acid sequences by PCR relies upon oligonucleotides or "primers" having conserved nucleotide sequences, wherein the conserved sequences are deduced from alignments of related gene or protein sequences, e.g., a sequence comparison of mammalian hK2 genes. For example, one primer is prepared which is predicted to anneal to the antisense strand, and another primer prepared which is predicted to anneal to the sense strand, of a DNA molecule which encodes an hK2 polypeptide.

In general, the isolated RNA is combined with a primer in a reverse transcriptase (RT) reaction to generate single strand cDNAs. Oligo-dT or random sequence oligonucleotides, as well as sequence specific oligonucleotides, can be employed as a primer in the RT reaction. See Sambrook et al., supra. The single strand cDNAs are then amplified with sequence specific primers to yield an amplified product.

To detect the amplified product, the reaction mixture is typically subjected to agarose gel electrophoresis or other convenient separation technique, and the presence or absence of the hK2-specific amplified DNA detected. Detection of the amplified hK2 DNA may be accomplished by excising or eluting the fragment from the gel (for example, see Lawn et al., *Nucleic Acids Res.*, 9, 6103 (1981), and Goeddel et al., *Nucleic Acids Res.*, 8, 4057 (1980)), cloning the amplified product into a cloning site of a suitable vector, such as the pCRII vector (Invitrogen), sequencing the cloned insert and comparing the DNA sequence to the known sequence of hK2. Alternatively, for example, the hK2 amplified DNA may be detected using Southern hybridization with an hK2-specific oligonucleotide probe, or comparing its electrophoretic mobility with DNA standards of known molecular weight.

The invention will be further described by reference to the following detailed examples.

EXAMPLE 1

Materials and Methods

Construction of mammalian hK2 expression vectors

A cDNA (approximately 820 bp long) encoding the entire prepro-hK2 (pphK2) (from nucleotide #40 to #858 relative to the start site of the pphK2 transcript), as shown in FIG. 2, was synthesized from RNA of human BPH tissue using reverse-transcription polymerase chain reaction (RT-PCR) technology with a pair of hK2 specifico Iigonucleotide primers (5'ACGCGGATCCAGCATGTGGGACCTGGTTCTCT 3'; SEQ ID NO:9 and 5'ACAGCTGCAGTTTACTAGAGG- TAGGGGTGGGAC 3'; SEQ ID NO:10). This cDNA was generated such that 5' and 3' ends (with respect to pphK2 sense sequence) were bracketed with BamH1 and Pst1 sequences, respectively. The cDNA was then purified by agarose gel electrophoresis, and digested with BamH1 and Pst1 restriction enzymes. The restricted cDNA was ligated with BamH1 -Pst1 digested pVL1393 plasmid vector and transformed into the *E. coli* HB101 strain. *E. coli* harboring pphK2 cDNA/pVL1393 plasmid vector were selected. The pphK2 containing insert was sequenced. Plasmid pphK2 cDNA/pVL 1393 was mass-produced in *E. coli* and purified by CsCl gradient ultra-centrifugation.

Plasmid pphK2/pVL1393 in *E. coli* HB101 has been deposited in the American Type Culture Collection, Rockville, Md., USA on May 2, 1994 under the provisions of the Budapest Treaty and has been assigned accession number ATCC 69614.

A 0.8 kb fragment representing the entire pphK2 coding sequence (FIG. 2) was generated by PCR using primers A (5'ATATGGATCCATATGTCAGCATGTGGGACCTGG TTCTCTCCA3') (SEQ ID NO:1 1) and B (5'ATATGGATCCTCAGGGGTTGGCTGCGATGGT3') (SEQ ID NO:12) and plasmid pVL1393 containing pphK2 (gift from Dr. Young, Mayo Clinic) as the template. PCR products were inserted into the TA-cloning vector (Invitrogen Corp., San Diego, Calif.) and the DNA of the entire insert was sequenced.

To obtain the mammalian hK2 expression vectors, the hK2-containing inserts were isolated from the corresponding TA clones and inserted into the Bcl1 site of the plasmid pGT-d (Berg et al., *Nucl. Acids Res.*, 20, 54–85 (1992)) (gift from Dr. Brian Grinnell, Lilly) under the control of the GBMT promoter. The mammalian expression vectors, PLNS-hK2 and PLNC-hK2 were obtained by cloning the 0.8 kb wild type hK2 insert from the corresponding TA vector into the plasmids, pLNSX and pLNCX (Miller et al., *Biotech.*, 9, 980 (1989)), respectively. The orientation of the insert in all the mammalian expression vectors was confirmed by DNA sequencing.

Generation of Recombinant Clones

AV12–664 (ATCC CRL-9595), a cell line derived from adenovirus-induced tumors in Syrian hamster, and DU145 cells were cultured in Dulbecco's modified Eagle's medium (high glucose) supplemented with 10% fetal bovine serum (D10F). PC3 cells were cultured in Minimal Eagle Medium containing 10% fetal bovine serum. AV12 cells were transfected with the hK2 expression vectors using the calcium phosphate method (Maniatis et al., supra (1989)). Three days after transfection cells were resuspended in D10F+200 nM methotrexate (MTX). Drug-resistant clonal cell lines were isolated after 2–3 weeks and their spent medium was analyzed by Western blots. PC3 and DU145 cells were transfected with hK2 mammalian expression vectors using lipofectamine (Gibco-BRL, Gaithersburg, Md.) and clones (PC3-hK2 and DU145-hK2) were selected in media containing 400 µg/ml G418.

Purification and Sequencing of the Protein

AV12-hK2 clones were grown in D10F+200 nM MTX. At about 60% confluency the cells were washed with Hank's balanced salt solution and resuspended in serum-free HH4 medium. The spent medium was collected 7 days after the addition of serum-free spent medium and stored at −20° C. To purify the protein, the serum-free spent medium was concentrated and exchanged into 50 mM sodium bicarbonate pH 8. Samples were filtered with 0.2µ filters and then pumped directly onto a TSK DEAE-5PW HPLC column, 21 mm×150 mm, at a flow rate of 5 ml/minute. Buffer A contained 50 mM Na bicarbonate pH 7.9 and Buffer B contained 50 mM Na bicarbonate plus 0.5 M NaCl pH 7.6. The elution profile was developed with a gradient from 0–50% Buffer B over 35 minutes; 50–100% B from 35–40 minutes and isocratic elution at 100% B for 5 minutes before re-equilibration in Buffer A. The flow rate was 5 mL/minute throughout. In the above procedure, borate buffer could replace bicarbonate buffer with no noticeable difference.

DEAE fractions were assayed for the presence of hK2 by the dried-down ELISA method (see below) using rabbit anti-pphK2 (Saedi et al., *Mol. Cell. Endoc.*, 109, 237 (1995)). Fractions with hK2 activity were pooled and concentrated by ultrafiltration with membranes (10 kD cut off) to approximately 5–8 mL. Solid ammonium sulfate was then added to a final concentration of 1.2 M. This sample was then injected onto a PolyLC, polypropyl aspartamide column, 1000 Å pore size, 4.6 mm×200 mm, to resolve proteins by hydrophobic interaction chromatography (HIC). Buffer A was 20 mM Na phosphate, 1.2 M Na sulfate pH 6.3 and Buffer B was 50 mM Na phosphate, 5% 2-propanol, pH 7.4. The elution gradient was 0–20% B over 5 minutes; 20–55% B from 5–20 minutes, isocratic at 55% B from 20–23 minutes, 55–100% B from 23–25 minutes; isocratic at 100% B for 2 minutes before re-equilibration Buffer A. The flow rate was 1 mL/minute. The HIC peak containing hK2 which eluted at about 50% B was exchanged into 50 mM borate buffer pH 8 by repeated concentration with CENTRICON-10 (Arnicon) 10 K MW cutoff ultrafiltration. Purity was assessed by both SDS-PAGE and Western blot analyses. The extinction coefficient used to estimate hK2$^{v217}$ concentrations was $A_{280}$ of 1.84=1 mg/ml.

In some cases the HIC peak containing hK2 was purified further by size exclusion chromatography (SEC) on a 10/30 Pharmacia S12 column. In this case the HIC peak containing hK2 was concentrated by ultrafiltration as above to less than 1 mL and then applied to the size exclusion column equilibrated in 100 mM ammonium acetate pH 7 or sodium borate pH 8. The flow rate was 0.7 mL/minute. The hK2 peak was then concentrated by ultrafiltration. The peak collected off SEC in ammonium acetate was lyophilized to remove the buffer and then was reconstituted in water. An aliquot of this sample was hydrolyzed in gaseous 6 N HCl under vacuum for 20 hours at 112° C. then reconstituted in 0.1 N HCl and analyzed on a Hewlett Packard Aminoquant amino acid analyzer utilizing pre-column derivatization of amino acids with OPA for primary and FMOC for secondary amines.

A HK1G 586.1 (see below) affinity resin was used to purify hK2 by affinity chromatography. HK1G 586.1 monoclonal antibody (mAb) was coupled with Pharmacia GAM-ABIND plus SEPHAROSE (cat. no. 17-0886) according to Schneider (J. Biol. Chem., 257, 10766 (1982)). Briefly, HK1G 586.1 mAb and resin were incubated overnight at 4° C. with rotation. Resin was centrifuged (500×g for 5 minutes at 4° C.) and washed twice with 0.2 M triethanolamine, pH 8.2. Amine groups were cross-linked in fresh cross linker solution (25 mM dimethyl pimelimidate dihydrochloride in 0.2 M triethanolamine, pH 8.2) for 45 minutes at room temperature (22° C.). The resin was quenched with 20 mM ethanolamine, pH 8.2, for 5 minutes at room temperature and then washed twice with 1 M NaCl, 0.1 M $PO_4$, pH 7.0. The resin was washed two more times with PBS and stored at 4° C. with 0.05% NaN3 until use.

An Applied Biosystems Model 477a pulsed liquid phase sequencer was used to sequence the proteins and the peptides. The Model 477a employs automated Edman degradation chemistry to sequentially release amino acids from the N-tenninus followed by PTH derivatization and chromatography by reversed-phase HPLC. The peptide samples were applied to the sequencer on biobrene-treated glass fiber filter supports and whole proteins were applied either to biobrene-treated filters or to pre-activated Porton filters (Beckman, Fullerton, Calif.). Samples sequenced off blots were first run as mini-gels on the NOVEX system (Novex, San Diego, Calif.) then transferred to Problot PVDF membrane, visualized with Commassie blue, the appropriate band cut out and sequenced directly from the PVDF membrane.

Monoclonal Antibody Production

A/J mice were injected with 50 µl of phK2 in complete Freund's adjuvant (CFA) i.p. on day 1, 25 µg of phK2 in incomplete Freund's adjuvant (IFA) i.p. on day 14 and 25 µg phK2 in PBS i.p. on day 28. Three days prior to fusion, mice were boosted with 10 µg of phK2 in PBS i.v. Mice were sacrificed and a single cell suspension was prepared from the spleens. Immune B cells were used with P3.653 myeloma cells. Cloned hybridomas were screened by ELISA and selected based on the reactivity of surpernatants to $hk2^{v217}$ and $phK2^{v217}$ and minimal reactivity with PSA. Two clones selected by these criteria, clones HK1G464 and HK1G586, were subcloned using FACSTAR plus cell sorter to deposit single cells onto mouse spleen feeder layers. Subclones HK1G464.3 and HK1G586.1 were used for further studies.

Another fusion, which employed the same protocol described above except that the immunogen was $hK2^{v217}$, alum was used instead of CFA and IFA, BALB/c mice were used instead of A/J mice, produced clone HK1H247.

Hybridoma clones HK1G464.3, HK1G586.1, HK1H247, HK1A523 and HKD106.4 have been deposited with the American Type Culture Collection, in accord with the Budapest Treaty, and granted Accession Nos: HB11983, HB12026, HB12162, HB11876 and HB11937, respectively.

Polyclonal and Monoclonal Antibody Production to hK2 Peptide Immunogens

Sheep and goats were immunized subcutaneously with 100 µg of KLH-conjugated peptide in complete Freund's adjuvant (CFA) and boosted at three week intervals with 100 µg of peptide in incomplete Freund's adjuvant (IFA).

For monoclonal antibodies to peptide immunogens, Balb/c mice were immunized subcutaneously with 100 µg of KLH-conjugated peptide in complete Freund's adjuvant (CFA) and boosted at three week intervals with 100 µg of peptide in incomplete Freund's adjuvant (IFA). Alternatively, A/J mice were immunized twice intraperitoneally with 50 µg of KLH-conjugated peptide and mice with positive titers were boosted intravenously with 25 µg of conjugate.

After the first three immunizations, blood from the animals was tested for the presence of antibody 6 to 10 days following the immunization. Peptides were immobilized on 0.25 inch polystyrene beads (Clifton, Clifton Heights, Pa.) by incubating 1 µg of peptide conjugated to BSA (bovine serum albumin) per bead in pH 9.6 carbonate buffer over night at 4° C. The beads were washed three times with 0.01M phosphate buffered saline (PBS), pH 7.4 with 0.1% Tween 20 and blocked with 1% skim milk plus 1% BSA. These beads were incubated for 18 hours with 250 µl of a 1:100, 1:1000 or 1: 10,000 dilution of animal sera. Following three washes, 250 µl of rabbit anti-sheep, anti-mouse or anti-goat antibody conjugated to horseradish peroxidase (Cappel-Organon Teknica Corporation, Durham, N.C.) was incubated with each bead for 3 hours on a horizontal incubator at 150 rpm. The enzyme signal was quantified spectrophotometrically using ortho-phenylene-diamine as a substrate. Nonimmune sera was used as a negative control and immune sera measurements were expressed as multiples of the control reading.

Lymphocytes from the spleens of mice with positive serum titers were fused with myeloma cells to produce hybridoma cells. Antibodies produced by clones of these cells were screened as described above. Positive clones were subcloned by limiting dilution and rescreened. Monoclonal hybridomas were injected into the peritoneal cavities of pristine primed mice to obtain ascitic fluid.

To purify monoclonal and polyclonal antisera, the antisera initially were subjected to an IgG separation by precipitation with saturated ammonium sulfate and size chromatography using an ultragel ACA-34 column. The polyclonal antisera was further affinity purified using columns produced by cyanogen-bromide coupling of the peptides to Sepharose 4B. The purified antibody was eluted from the column with acidic PBS (pH 2.45).

ELISA assays

A dried-down ELISA format was used to measure hK2 in the setum-free spent medium of the clones and in the fractions collected during hK2 purification. Microtiter plates (Becton Dickinson Labware, NJ) were coated with 50 µl of spent media or column fractions overnight at 37° C. The wells were washed with PBS +0.1% TWEEN 20 (PBST) and incubated for one hour with 50 µl of primary antibodies. The wells were washed again with PBS+T and incubated for one hour at 37° C. with 50 µl of goat anti mouse-IgG or goat anti rabbit-IgG Fc antibodies coupled with horseradish peroxidase (1:500, Jackson Immunosearch Laboratories, Inc., West Grove, Pa.). The wells were washed with PBST, incubated with o-phenylenediamine dihydrochloride (OPD, Sigma, Mo.) for 5 minutes, and the colorimetric reaction was measured at $A_{490}$ with an ELISA reader (Biotek Instruments, Inc., model EL310, VT). All samples were assayed in duplicate. The serum-free spent medium from AV12 cells transfected with vector alone was used as negative control.

Antibodies were tested in a solution-based ELISA format using biotinylated phK2$^{v217}$, hK2$^{v217}$, and PSA. PSA was purified by the method of Sensabaugh and Blake (*J. Urology*, 144, 1523 (1990)). Twenty ng of biotinylated hK2$^{v217}$ or phK2$^{v217}$ diluted in 50 µl Buffer A (8.82 mM citric acid, 82.1 mM sodium phosphate (dibasic), 10% BSA, 0.1% mannitol, 0.1% NONIDET P-40, pH 7.0) or 0.25 ng biotinylated PSA diluted in 10% horse serum (HS) in PBS was incubated with 50 µl of hybridoma supernatants, negative control supernatants (i.e., irrelevant hybridoma supernatant for phk2$^{v217}$ and phK2$^{v217}$, or 20 µg/ml irrelevant purified mAb in HS for PSA), or positive control supernatants (i.e., 20 µg/ml purified PSM773 (anti-PSA) mAb in HS for PSA, or HK1D 104 (anti "hK2") hybridoma supernatant for phK2$^{v217}$ and hK2$^{v217}$). HCO514, a mnAb against hCG, was used as a negative control in PSA assays, and ZTG085, a mAb against the tau, was used as a negative control in hK2 assays.

These mixtures of antibodies and antigens were allowed to incubate for 1 hour with shaking in a streptavidin coated microtiter plate (Labsystenis, Helsinki, Finland). The plate was washed 3 times with 300 µl of PBS, 0.1% TWEEN-20 (PBST), and incubated with 100 µl of gamma-specific goat anti mouse IgG-horseradish peroxidase conjugate (Jackson ImmunoResearch Laboratories, Inc., Westgrove, Pa.), diluted 1:10,000 in HS, with shaking for 1 hour. After a second PBST washing, color was developed for 30 minutes, with shaking, following the addition of 100 µl of 1 mg/ml o-phenylenediamine in 50 mM phosphate-citrate buffer, 0.03% sodium perborate, pH 5.0 (Sigma Chemical, St. Louis, Mo.). The reaction was quenched by the addition of 50 µl 4 N $H_2SO_4$. The color intensity was determined by measuring the absorbance at 490 nm and 540 µm using a microtiter plate reader. Absorbances above 2.6 at 490 nm were corrected with 540 mn reading. Sample values are averages: standard deviation of triplicates. Control values are averages of duplicates.

Western Blot Assays

Western blot analyses were performed using standard procedures. Serum-free spent media were concentrated ten fold using CENTRICON 10 (Amicon, Inc., Beverly, Mass.) and subjected to SDS/PAGE using a 12% gel (Bio-Rad, Inc., Melville, N.Y.). For analytical purposes, SDS/PAGE was performed on a Pharmacia PHASTSYSTEM using 8–25% gradient gels. After electrophoresis, proteins were transferred onto nitrocellulose membrane and blocked overnight at 4° C. with 2% nonfat dried milk in PBS. Blots were rinsed then incubated with primary antibody (1:1000 dilution of ascites, or 1 µg/ml of purified mAbs or polyclonal Abs) for 1 hour at 22° C. Blots were then washed and incubated for 45 minutes with secondary antibody (Goat anti-mouse-HRP or goat anti-rabbit-HRP, 1:500, Jackson Immunosearch Laboratories, Inc., West Grove, Pa.). The immunoreactive bands were detected by developing the blot using DAB (Sigma, St. Louis, Mo.) plus $H_2O_2$ or by using the ECL (Amersham, Buckinghamshire, England) system according to manufacturer's instructions.

Covalent Complex Formation

To test for covalent complex formation, 0.175 µM hK2 was incubated with 20 µM of inhibitor at pH 8 in 100 mM borate buffer. inhibitors tested were 1-antichymotrypsin, 1-antitrypsin, 1-antiplasmin, antithrombin and 2-macroglobulin. To 5 µl of hK2 (10 µg/ml) was added the calculated µg of inhibitor prepared in 100 nM borate buffer and, if needed, each sample brought up to a total volume of 10 µl. Samples were incubated for 3 hours at 37° C. whereupon 1.5 µl of 7× PHASTSYSTEM SDS sample buffer containing 35% 2-mercaptoethanol was added and the sample boiled for 3 minutes in a water bath. Samples were diluted ¼ in SDS sample buffer prior to application to SDS/PAGE and Western analyses.

Proteolysis of Peptide Substrates

To determine the ability of hK2 to cleave peptide substrates, peptides were dissolved in DMSO at 10 mg/ml then diluted 1:10 into 100 MM borate buffer pH 8 containing PSA, hK2 or trypsin. Typical experiments were performed as follows: 1 µl of peptide was added to 7 ul of 100 mM borate buffer and then 2 µl of hK2 (10 µg/ml), PSA (500 µg/ml) or trypsin (0.5 µg/ml) were added. In general, samples were incubated for 16 hours at 37° C.

Samples were quenched with 100 µl of 0.2% TFA/water and the quenched sample was applied directly to a VYDAC C-18 reversed-phase column attached to a BioRad Model 800 HPLC equipped with an AS100 autosampler, dual 1350 pumps and Biodimension scanning UV-VIS detector. Solvent A was 0.1% TFA/water and Solvent B was acetonitrile containing 0.1% TFA. The sample was applied in 90% solvent A and the gradient developed to 60% solvent B in 10 minutes. Absorbance was monitored simultaneously at 220 in and 280 nm.

Peaks collected off HPLC were concentrated by vacuum centrifugation or lyophilization and then applied to the amino acid sequencer to identify individual fragments. In some cases 10 µl of the quenched sample mixture was applied directly to the sequencing membrane and, since the sequence was known, the cleavage sites were determined from the distribution of amino acids present in each cycle.

Protease Assays Using Chromogenic Substrates

Assays to measure the hydrolysis of para-nitroanilide derivatized substrates were performed using an HP 8452A UV-VIS spectrophotometer equipped with a programmable, thermostated 7-position cell holder. Assays were performed in 100 mM sodium borate pH 8 incubated at 37° C., the absorbance increase monitored at 405 nm. Methoxysuccinyl-Arg-Pro-Tyr-para-nitroanilide (MeO-Suc-R-P-Y-pNA) and H-D-pro-phe-arg-para-nitroanilide (P-F-R-pNA) were 1 mM in the assay.

An ABI model 431A peptide synthesizer using standard FastMoc chemistry was employed to synthesize all of the peptides listed in FIG. 16 except #2, angiotensinogen and #5, oxidized beta-chain of insulin which were obtained from Sigma. The mass of each synthesized peptide was confirmed by mass spectrometry (University of Michigan, Core Facility) using ES/MS. An ABI Model 477a sequencer described above was employed to confirm peptide sequence.

Conversion of phK2$^{v217}$ to hK2$^{v217}$

Figure 17A:
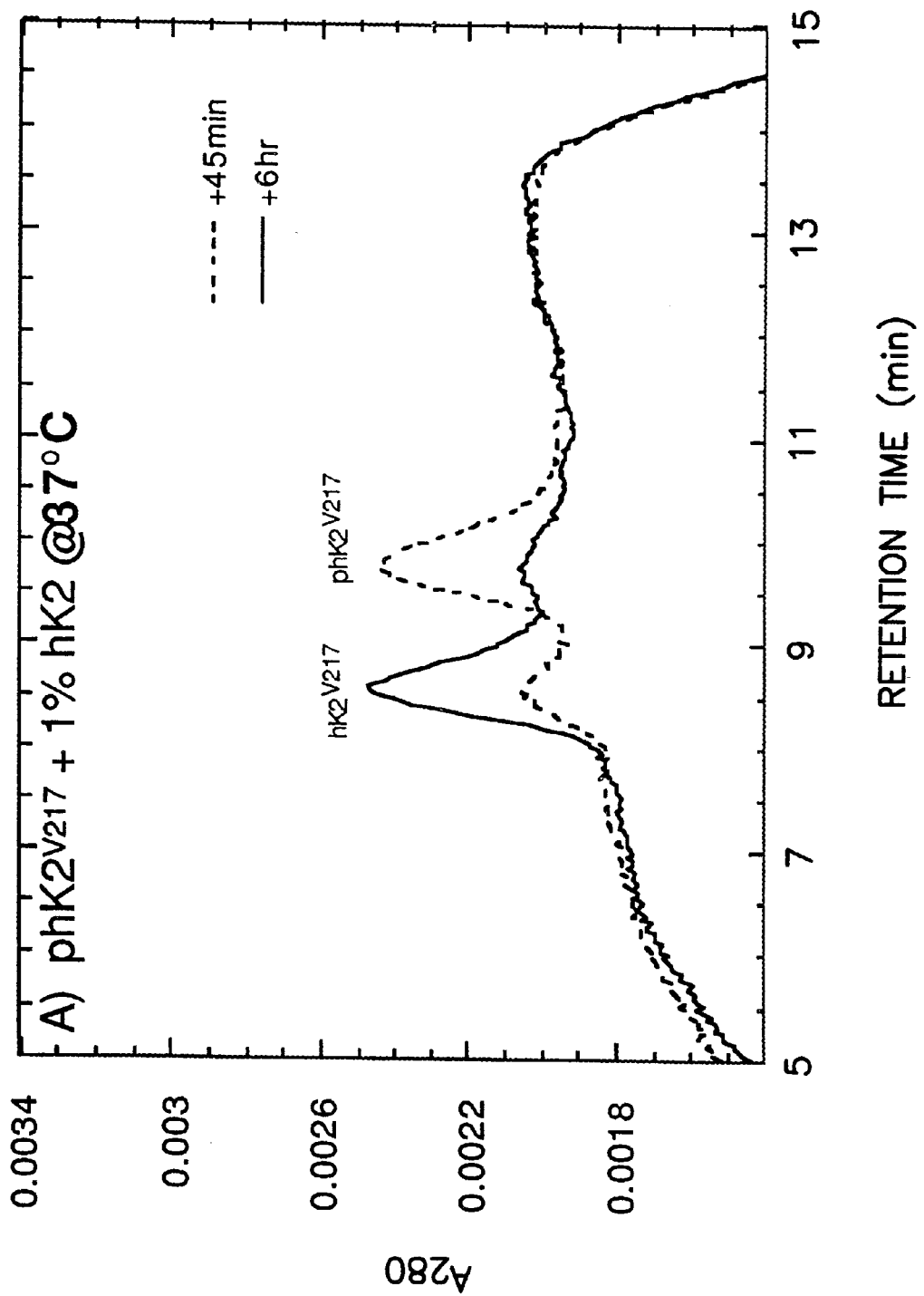
Figure 17B:
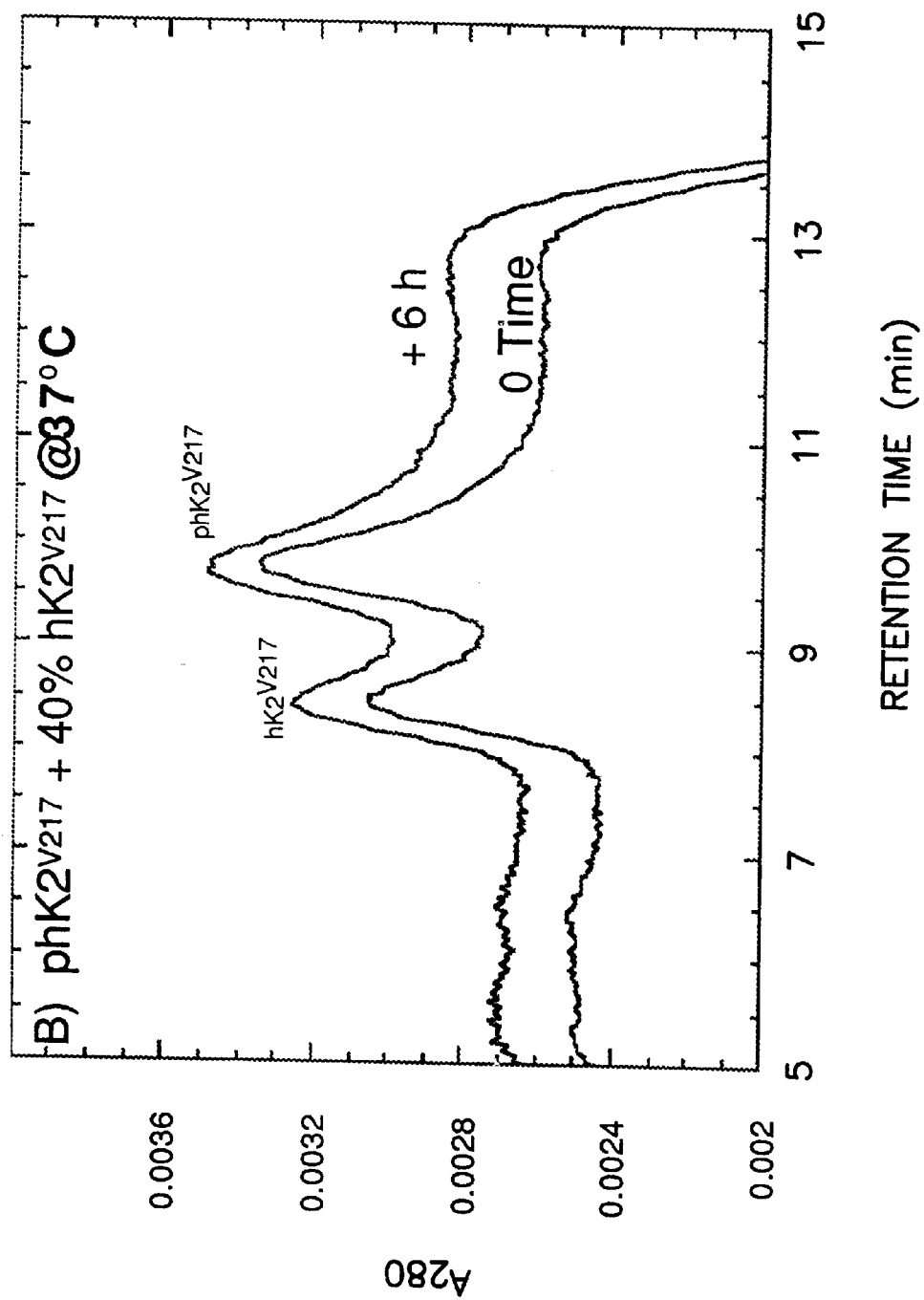

Samples of phK2$^{v217}$ at 100–400 µg/ml in 50 mM sodium borate were incubated with 1% w/w trypsin or hK2 at 37° C. The conversion of pro to mature was monitored by dilution of 1–2 µg of hK2$^{v217}$ starting material into 100 µl HIC Buffer A and resolution of the two forms by HIC-HPLC as described above. The incubation of hK2$^{v217}$ with phK2$^{v217}$ was conducted in the same manner except that comparable amounts of the two forms were incubated together as seen in FIG. 17B.

EXAMPLE 2

Expression and Purification of hK2$^{v217}$ in Mammalian Cells

To express hK2 in mammalian cell lines, a 0.8 kb fragment encoding the entire coding sequence of hK2 (pphK2)

(FIG. 2) was amplified using PCR, subcloned into the vector PCR II (TA) and several clones were isolated. The nucleotide sequence of the entire pphK2 insert in a few of these clones was determined to detect any mutations that may have been caused by PCR amplification.

Figure 3:
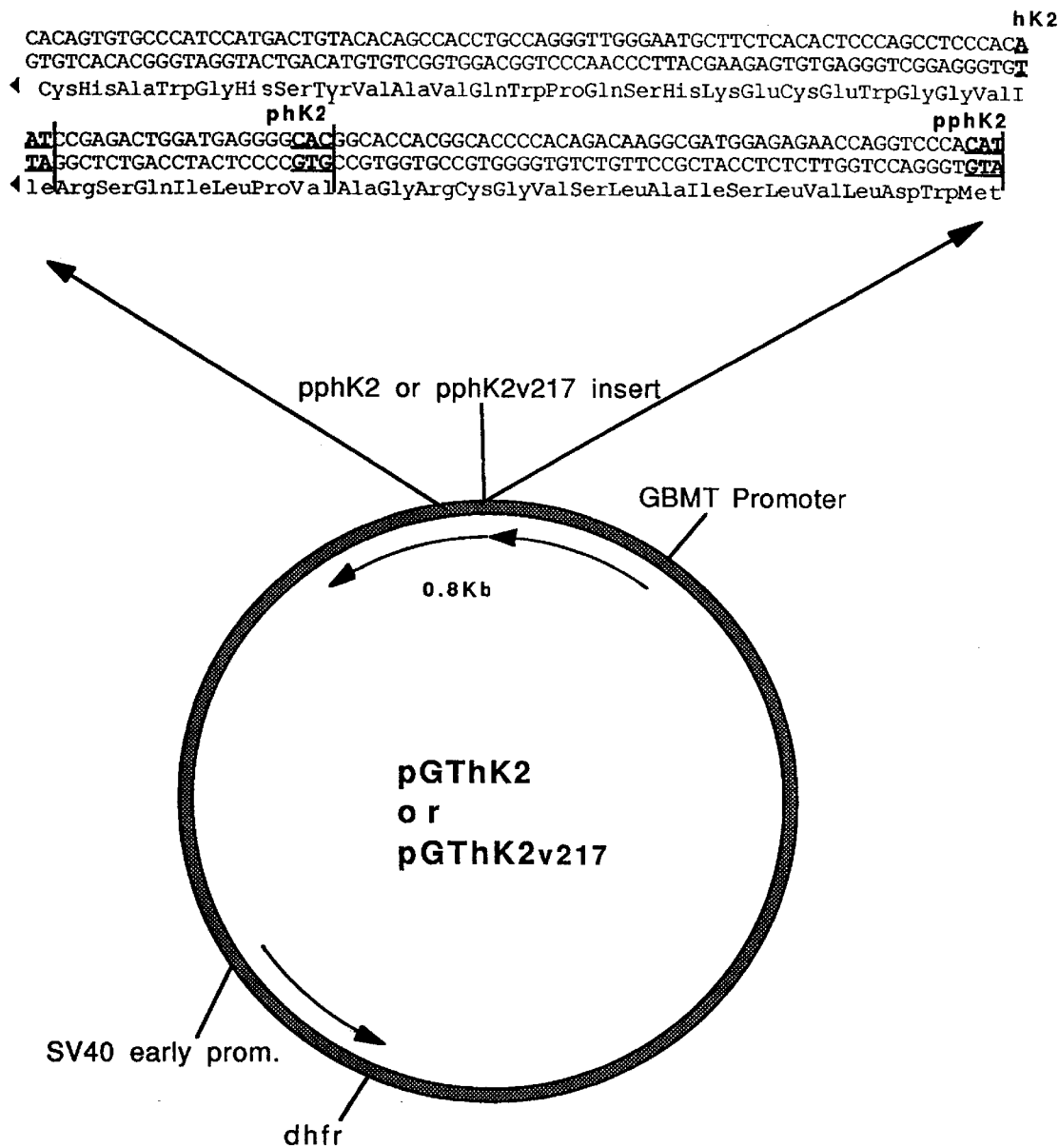
FIG. 3 is a schematic diagram, including SEQ ID NO:42 and SEQ ID NO:43, of the pGT expression vectors pGThK2 and pGThK2$^{v217}$.

Two clones, one having a wild type hK2 insert, TA-hK2, and one having a mutant hK2 insert, TA-hK2v$^{27}$, were selected for further analysis. TA hK2$^{v217}$ contains a substitution of T for C at codon 650 of hK2 resulting in a conservative substitution of valine (GTT) for alanine (GCT) at amino acid residue 217 of hK2 (FIG. 2). To obtain mammalian expression vectors, pphK2 inserts of TA-hK2 and TA-hK2$^{v217}$ were subcloned into plasmid PGT-d under the control of the GBMT promoter resulting in plasmids pGThK2 and pGThK2$^{v217}$ (FIG. 3). The GBMT promoter is composed of several regulatory sequences and is activated by the adenovirus E1a protein(s) (Berg et al., supra (1992)).

To determine whether the product of the pphK2$^{v217}$ gene would be expressed in mammalian cells, the plasmid pGThK2$^{v217}$ was transfected into AV12-664 cells. This cell line is derived from a tumor induced in Syrian hamster by adenovirus type 12 and expresses the adenovirus E1a protein. The E1a protein activates the GBMT promoter which results in the expression of the gene product under the control of this promoter. After 2–3 weeks, MTX-resistant clonal cells were isolated and their spent medium were analyzed by Western blots. Several clones were identified which secreted into the media a polypeptide immunoreactive to anti-pphK2 antiserum. One clone (AV12-pGThK2$^{v217}$ #2) was selected for further characterization and protein purification.

Figure 4A:
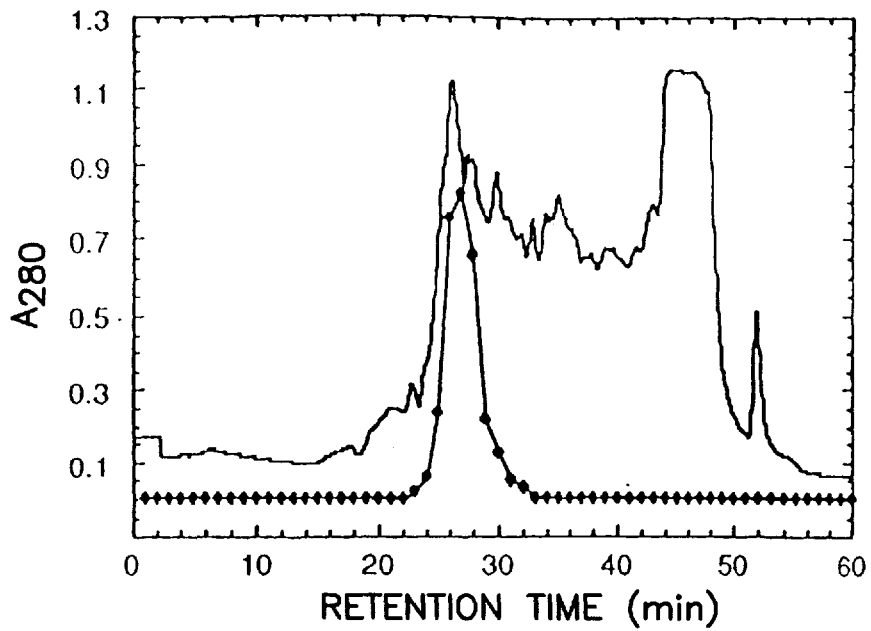
FIG. 4 depicts chromatographic profiles from the purification of phK2$^{v217}$. (A) A DEAE chromatogram of 7 day spent medium from AV12 cells transfected with a vector encoding pphK2$^{v217}$. A sample of the spent medium was applied in bicarbonate buffer, pH 8 and eluted with a salt gradient. The $A_{280}$ elution profile is represented by a solid line. The dotted line represents the results of an ELISA assay of a portion of individual column fractions which was dried onto microtiter plates and developed with a rabbit anti-pphK2 antibody. (B) The hydrophobic interaction profile of pooled DEAE fractions. Fractions 24 to 30 from the DEAE chromatographic eluates of (A) were pooled, concentrated and applied to an HIC (hydrophobic interaction column) column in 1.2 M sodium sulfate, and eluted with a decreasing salt gradient. The elution profile ($A_{280}$) is represented by a solid line. The dotted line represents the results of an ELISA assay of a portion of individual column fractions which was dried onto microtiter plates and developed with a rabbit anti-hK2 antibody. (C) hK2-containing fractions from the 22 minute peak from (B) were concentrated and applied to a Pharmacia S12 size exclusion column. Fractions were collected and analyzed by SDS/PAGE. The 19.4 minute peak appeared homogeneous by SDS-PAGE.

To purify hK2 polypeptides, the serum-free spent medium from AV12-pGThK2$^{v217}$ clone #2 was collected after 7 days, concentrated and subjected to anion exchange chromatography (FIG. 4A). The peak of hK2 activity eluted at approximately 0.2 M NaCl as determined by ELISA assays (dotted line). The ELISA assay correlated well with the appearance of about a 34 kD band of protein seen by SDS/PAGE in the same fractions.

Figure 4B:
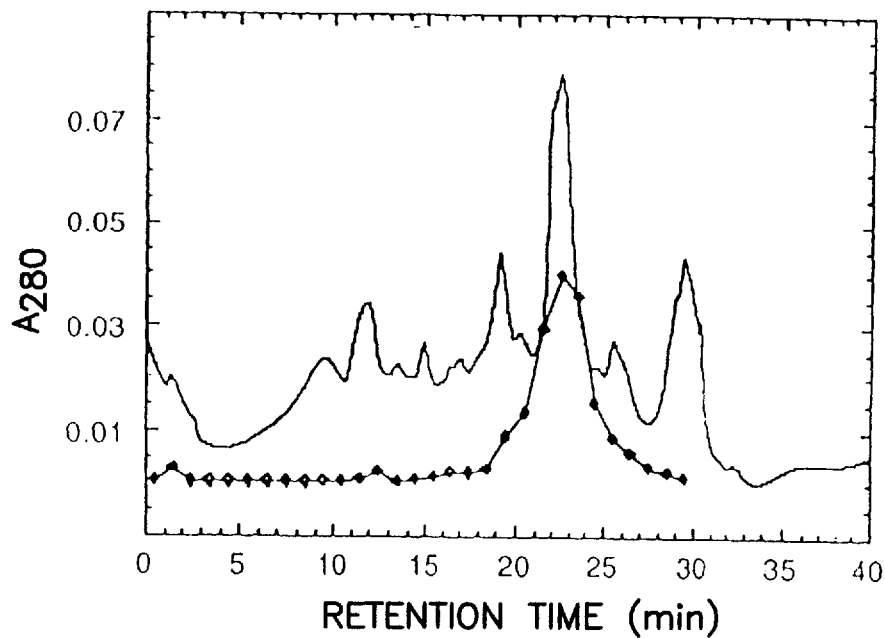
Figure 4C:
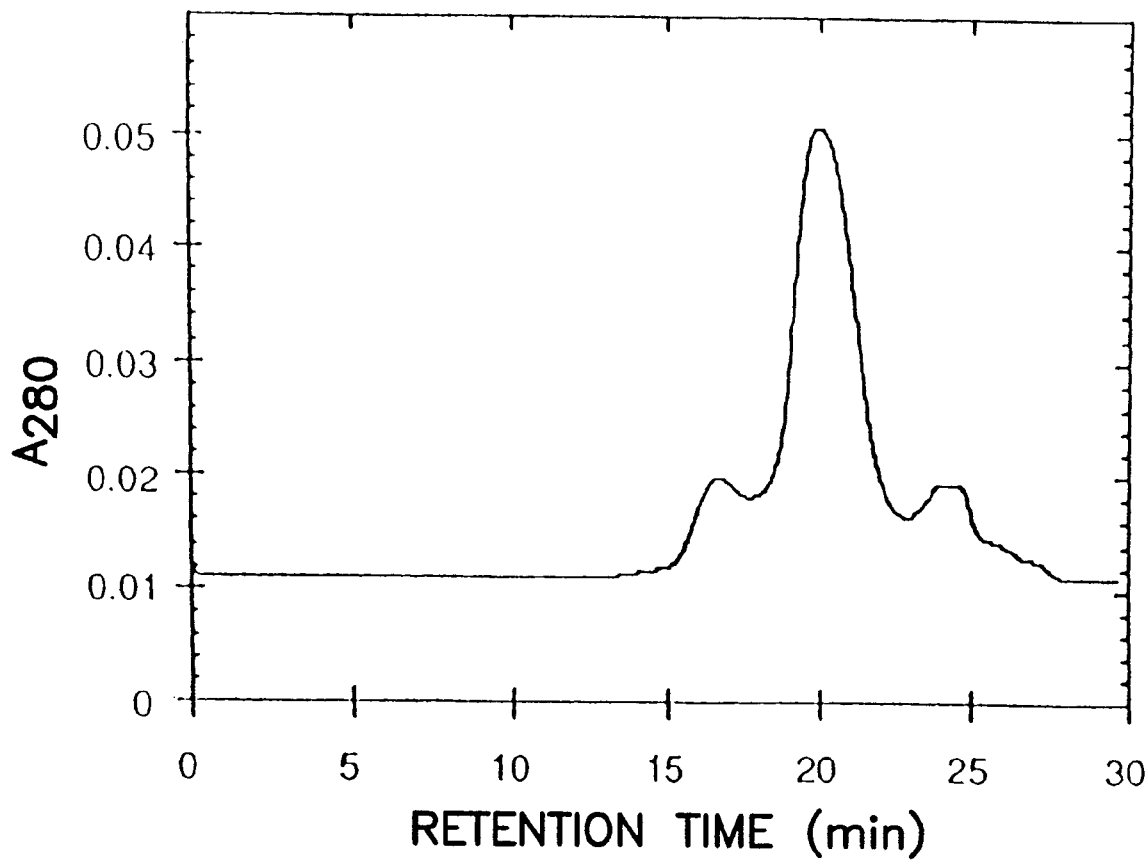

The hK2-positive fractions from the anion exchange column were collected and subjected to hydrophobic interaction chromatography (HIC) (FIG. 4B). A major portion of the A$_{280}$ was not retained on HIC column. The main peak retained on HIC, which eluted at 22 minutes, also showed the highest peak of activity by ELISA assay (dotted line, FIG. 4C). A major protein band at about 34 kD was also observed by SDS-PAGE. When the 22 minute peak from HIC was resolved by SEC, typically about 80–90% of the protein A$_{280}$ eluted at 19.4 minutes, a retention time consistent with a protein of approximately 34 kD (FIG. 4C). The only other protein peak on SEC, eluting at 16.7 minutes, corresponded to about a 70 kD protein observed in previous purification steps.

To further identify the purified protein, approximately 2.5 μg of the protein was subjected to automated N-terminal analysis which yielded the following sequence: Val-Pro-Leu-Ileu-Gln-Ser-Arg-Ileu-Val-Gly-Gly-Trp-Glu-(SEQ ID NO:38). No competing sequence was evident from the profile of amino acids released sequentially by the Edman degradation procedure. By analogy to PSA this protein is phK2$^{v217}$, since the known sequence of mature PSA (isolated from seminal fluid) begins with Ileu-Val-Gly- and pPSA and phK2 have been postulated to have an extra 7 amino acids at the N-terminus (FIG. 2). Amino acid analysis of this protein yielded an amino acid composition consistent with the predicted sequence of phK2$^{v217}$. This phK2 polypeptide was isolated and purified in mg quantities.

EXAMPLE 3

Characterization of phK2$^{v217}$ and Generation of hK2$^{v217}$

Figure 5:
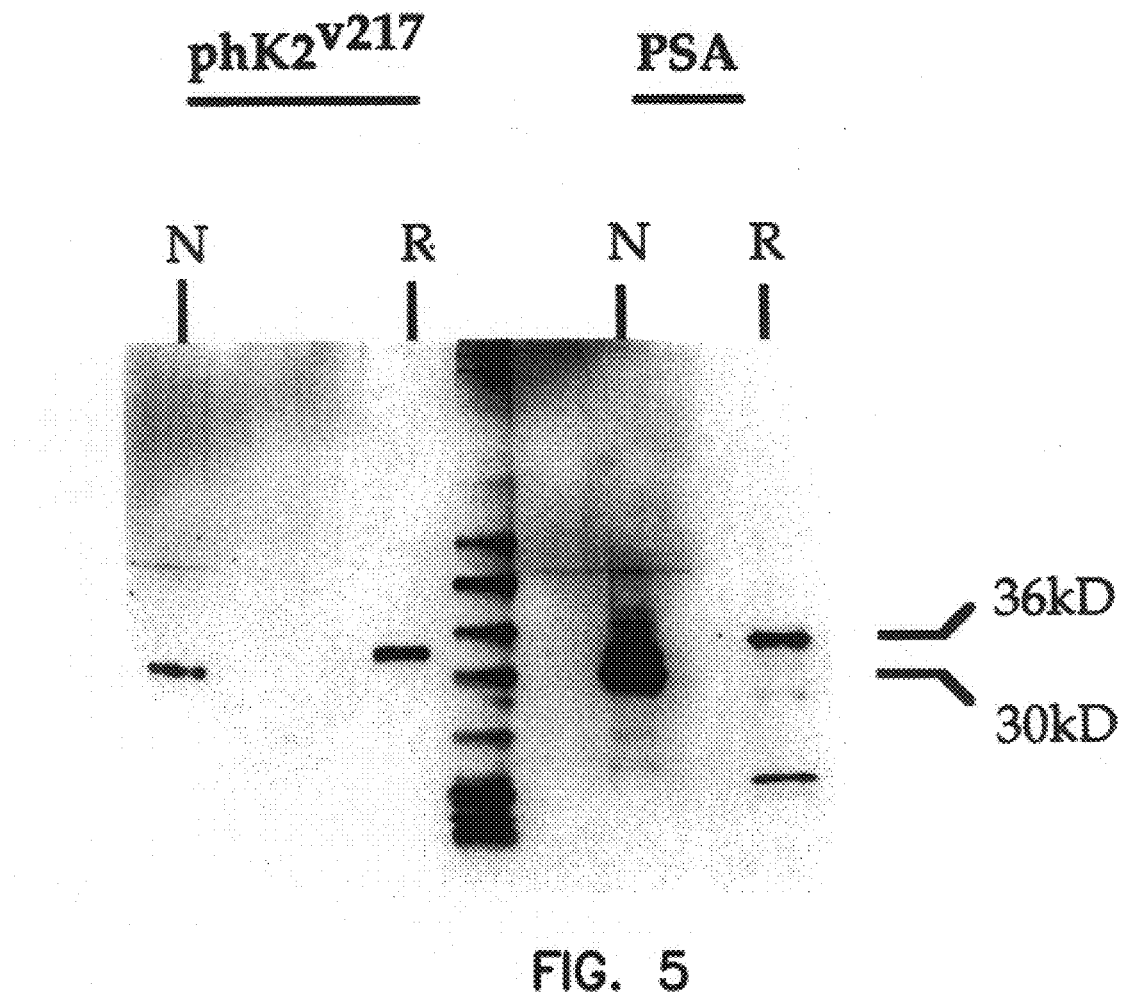
FIG. 5 represents an SDS/PAGE analysis of purified hK2 and PSA. A 1.5 mg sample of purified phK2$^{v217}$ or PSA was boiled in sample buffer with (R) or without (N) 1% beta-mercaptoethanol. Samples were subjected to SDS/PAGE on a 4–20% gel. The protein bands were visualized by staining the gel with silver.

To examine the efficiency of the purification scheme employed in Example 2, 1.5 μg of purified phK2$^{v217}$ was subjected to SDS/PAGE in the presence or absence of beta-mercaptoethanol (BME), and the gel was stained with silver. Results showed that the phK2$^{v217}$ in the sample was about 95% pure (FIG. 5). It also showed that phK2$^{v217}$ migrated at about 30 kD in the absence of BME, and at about 34 kD in the presence of BME. This pattern is similar to that observed for the PSA purified from seminal fluid (FIG. 5).

The amino acid sequence of hK2, deduced from the cDNA sequence, shows the presence of one potential N-linked glycosylation site at residue 78 (N-M-S). To determine if this site is glycosylated, phK2$^{v217}$ was subjected to SDS/PAGE, transferred to nitrocellulose paper, reacted with digoxigenin (DIG)-coupled lectins followed by horseradish peroxidase labeled anti-DIG.

Figure 6:
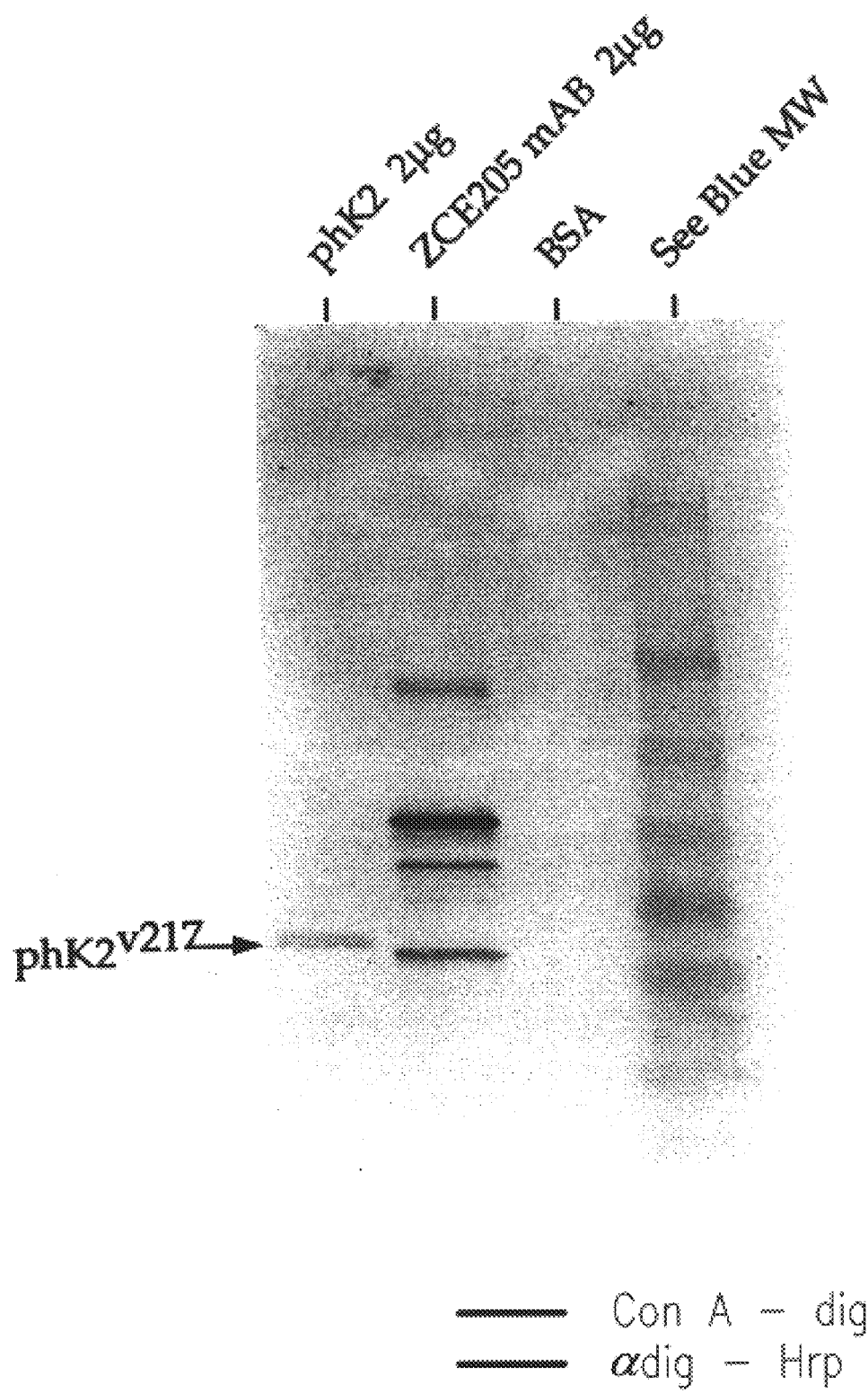
FIG. 6 depicts Conconavalin A staining of phK2$^{v217}$. The predicted position of phK2 is designated by an arrow. ZCE (an anti-CEA mAb) and BSA were included as examples of glycosylated and non-glycosylated proteins, respectively. The presence of a band at the predicted position in the phK2 lane demonstrates that this protein is glycosylated.

In FIG. 6 (lane 1), 2 μg of phK2 was stained with concanavalin A (Con A) suggesting the presence of two nonsubstituted or 2-O-substituted α-mannosyl residues in the protein. Lane 2 shows Con A staining of the positive control glycoprotein, ZCE025 mAB. Both the heavy chains (50 kD) and light chains (25 kD) of this mAb are known to contain N-linked oligosaccharides with mannose cores. Lane 3 shows that a nonglycosylated protein (BSA) fails to react with the Con A lectin. phK2$^{v217}$ also reacted with RCA (Gal b1-4GlcNAc specificity) and AAA, (α(1–6) linked fucose specificity). This pattern of lectin reactivity is consistent with the presence of complex N-linked oligosaccharides. The oligosaccharides on phK2$^{v217}$ also contain sialic acid since both SNA (sialic acid linked α(2–6) to galactose) and MAA (sialic acid linked α(2–6) to galactose were reactive with phK2$^{v217}$.

Figure 7:
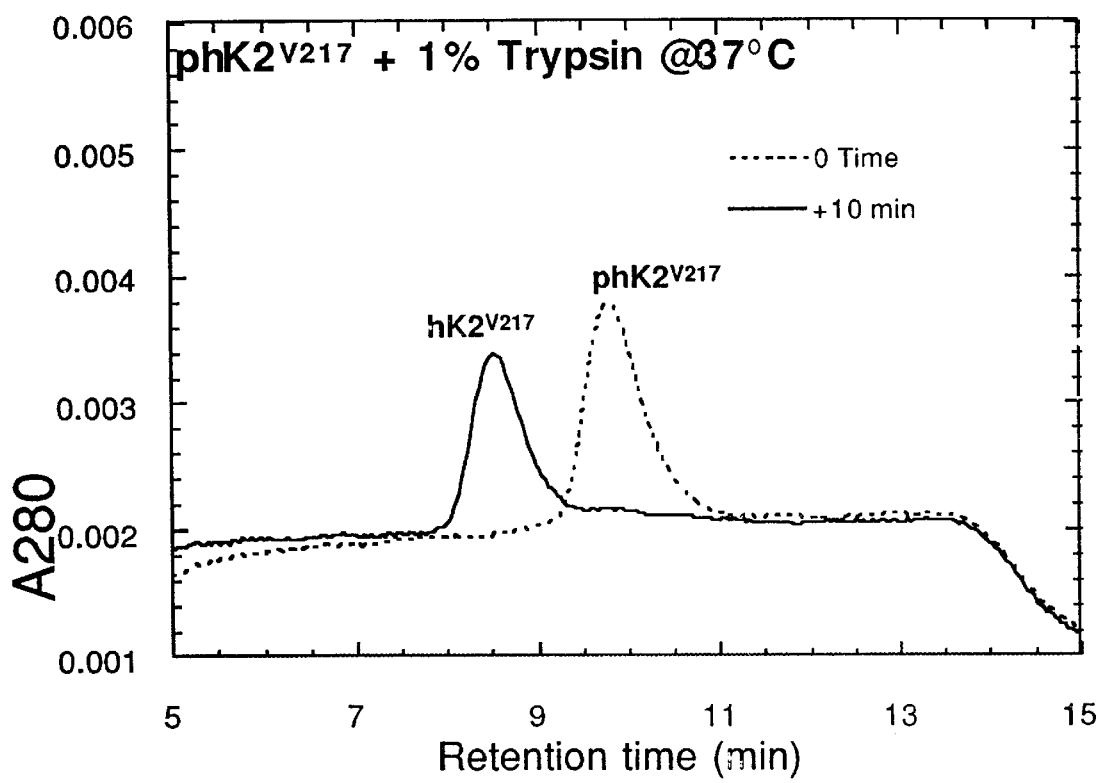
FIG. 7 represents the conversion of pro to mature hK2$^{v217}$ by trypsin cleavage. Trypsin (1% w/w) was incubated with phK2$^{v217}$ for 10 minutes at 37° C. in 100 mM borate buffer pH 8, and then subjected to HIC-HPLC. The dashed line represents the profile of the phK2$^{v217}$ prior to incubation with trypsin. The solid line represents the profile of phK2 after trypsin digestion. The profiles have been superimposed for comparison. The identity of the two forms was confirmed by N-terminal sequencing of the protein.

The sequence of the pro region of hK2 is VPLIQSR (SEQ ID NO:37). An enzymatic cleavage at the carboxy-terminal end of the arginine in this pro sequence would convert phK2 to hK2. A mild trypsin digestion was developed to hydrolyze the peptide bond of purified phK2$^{v217}$ at this position. phK2$^{v217}$ was incubated with 1% trypsin and the conversion was monitored by HIC-HPLC (FIG. 7). This procedure resulted in a complete conversion of phK2$^{v217}$ to hK2$^{v217}$. The peak designated hK$_2$$^{v217}$ was N-terminally sequenced and shown to begin with the sequence, IVGGWE (SEQ ID NO:39), which is the N-terminus for the mature form of hK2. No sequence other than the above was detected, demonstrating that this mild trypsin treatment does not result in any significant level of non-specific cleavage. SDS/PAGE of trypsin-treated samples showed a small but discernible increase in mobility, generally consistent with a minor reduction in mass of 826 daltons, the mass of the pro peptide.

EXAMPLE 4

Generation of hK2-specific Abs phK2$^{v217}$ and hK2$^{v217}$ were used as immunogens to generate mAbs against hK2. Hybridomas were screened based on high reactivity with hK2$^{v217}$ or phK2$^{v217}$ and minimal reactivity with PSA. Representatives of mAbs obtained from the hybridomas are shown in Table 2. Immunization with phK2$^{v217}$ resulted in mAb HK1G586.1 and HK1G 464.3. HK1G586.1 was hK2-specific, since it recognized both phK2$^{v217}$ and hK2$^{v217}$ but not PSA. On the other hand, HK1G464 was phK2-specific, since it only recognized phK2$^{v217}$ and not hK2$^{v217}$ or PSA.

TABLE 2

Specificity of various mAbs raised to hK2$^{v217}$ and phK2$^{v217}$

A. mAbs raised to phK2$^{v217}$

| mAbs | PSA | hk2$^{v217}$ | phK2$^{v217}$ |
|---|---|---|---|
| Irrelevant Ab | 0.245 | 0.162 | 0.125 |
| positive control | 2.242 ± 0.06 | 9.196 | 8.91 ± 0.02 |
| HK1G586.1 (10 μg/ml) | 0.150 ± 0.004 | 11.154 ± 0.18 | 10.146 ± 0.87 |
| HK1G464.3 (Ascites 1:2000) | 0.143 ± 0.03 | 0.245 ± 0.02 | 6.644 ± 0.17 |

B. mAb raised to hK2$^{v217}$

| mAb tested | PSA | hK2$^{v217}$ | phK2$^{v217}$ |
|---|---|---|---|
| Irrelevant Ab | 0.157 ± 0.18 | 0.132 ± 0.01 | 0.153 ± 0.01 |
| Positive control | 2.768 ± 0.08 | 8.342 ± 1.3 | 9.673 ± 0.99 |
| Media only (neg. control) | 0.129 ± 0.02 | 0.240 ± 0.02 | 0.247 ± 0.01 |
| HK1H247 | 0.157 ± 0.01 | 9.34 ± 0.7 | 0.179 ± 0.004 |

Immunization with hK2$^{v217}$ resulted in mAb HK1H247. This mAb was hK2-specific since it recognized only hK2$^{v217}$ but not phK2$^{v217}$ or PSA. These results show that phK2$^{v217}$ and hK2$^{v217}$ are effective as immunogens in generating mAbs specific for different forms of hK2.

Western blot analysis was used to examine if HK1G586 recognizes hK2 in seminal fluid (FIG. 8). hK2-immunoreactive bands at about 22 kD, 33 kD, and 85 kD were recognized by this mAb. A similar hK2-immunoreactive pattern in seminal fluid was also recently reported by Deperthes et al., Biochem. Biophy. Acta, 1245, 311 (1995). This result indicates that a mAb raised to hK2$^{v217}$ recognizes native hK2 in seminal fluid. All the antibodies raised to hK2$^{v217}$ or phK2$^{v217}$ also recognized the corresponding form of hK2 and phK2 indicating that hK2 and phK2 are immunologically similar to hK2$^{v217}$ and phK2$^{v217}$, respectively (see below).

To prepare additional anti-hK2 antibodies (Abs), a direct primary structure comparison between the members of human kallikrein gene family and computer-aided antigenicity and hydrophobicity analyses was conducted. From this comparison, several hK2 oligopeptide sequences were selected. The selected hK2 peptides correspond to mature hK2 amino acid residues 8–26 (SEQ ID NO:19), 15–26 (SEQ ID NO:26), 41–56 (SEQ ID NO:20), 43–66 (SEQ ID NO:24), 153–167 (SEQ ID NO:21), 17–71 (SEQ ID NO:22) and 210–235 (SEQ ID NO:25). The peptide corresponding to amino acids 17–71 was synthesized in order to increase the likelihood of producing antibodies that recognize the native form of hK2. The peptides were synthesized and HPLC purified in the Protein Core Facility at Mayo Clinic/Foundation. Peptides were conjugated with keyhole limpet hemocyanin (KLH) and BSA for immunogens and assay reagents, respectively. Sheep, goat and mice were immunized with KLH-hK2 peptides for polyclonal (sheep and goat, SEQ ID Nos:20 and 21, and SEQ ID Nos:19, 20, 21, 24, 25 and 26, respectively)) and monoclonal antibody (mice; SEQ ID Nos:19, 20, 21, 24, 25 and 26) production. The 17–71 peptide (SEQ ID NO:22) was oxidized to generate an intramolecular disulfide bond between cys 26 and 42 and used to immunize goats and mice for polyclonal and monoclonal antibody production, respectively.

The hK2 41–56 Ab from sheep was first purified by hK2 41–56 peptide-affinity column and then used for Western blot analysis. The antibody recognized recombinant hK2. The detection of hK2 by the hK2 41–56 Ab was abolished by addition of excess hK2 41–56 peptide but not by PSA 41–56 peptide. Moreover, monoclonal anti-hK2 41–56 peptide antibodies were highly specific for hK2 protein in Western analysis.

Anti-hK2 153–167 peptide antiserum (sheep) recognized recombinant hK2. These results suggested that antibodies to peptides 41–56 and 153–167 react with two distinct epitopes in hK2 polypeptides.

Antisera against hK2 amino acid residues 210–235 showed the highest immunoreactivity.

A goat antiserum raised against hK2 peptide 17–71, which has 69% homology with corresponding region of PSA, recognized recombinant hK2 protein but not PSA.

Rabbit antiserum to bacterially expressed recombinant hK2 protein, which recognizes both PSA and hK2, detected a doublet protein band in concentrated LNCaP cell medium from LNCaP cells which were treated with androgen. In contrast, no immunoreactive protein was detected in LNCaP cell medium from LNCaP cells which were not treated with androgen. Thus, the immunoreactive proteins were induced by androgen. Moreover, the upper band in LNCaP media is a PSA-related protein because a PSA-specific antiserum (rabbit anti-PSA antisera, which was raised against bacterially expressed recombinant PSA) detected mainly the upper band. The lower band in LNCaP media is an hK2-related protein because a mouse monoclonal antibody (HK1A523) against hK2 41–56 peptide that has monospecificity for hK2 recognizes the lower protein band. These results were confirmed by sequence analysis of N-terminal amino acids of each protein in the doublet bands.

Immunohistochemistry studies of paraffin-embedded human prostate tissue sections (see Example 10) which employed a monoclonal antibody for hK2 peptide 41–56 (HK1A523) showed that hK2, like PSA, is produced in the epithelia, but not in stroma. Moreover, the immunostaining is specific for hK2 protein in the prostate, as other tissues tested were negative for hK2.

EXAMPLE 5

Expression of hK2 in Mammalian Cells

To express wild type hK2 (hK2) in mammalian cells pGThk2 (FIG. 3) was transfected into AV12 cells. Several clones expressing an hK2 polypeptide were identified by Western analysis using HK1D 106.4 (a hK2-specific mAb raised to a polypeptide corresponding to amino acid residues 17–71 of hK2). Clone AV12-hK2 #27 (AV12-hK2) was selected for further analysis based on its higher hK2 expression level. Cells transfected with vector alone (pGTD) showed no reactivity with HK1D 106.4.

ELISA using HK1D 106.4 mAb indicated the presence of about 0.5–1 μg/ml of an hK2 polypeptide in the serum-free spent medium of AV12-hK2 at day 7. The same method used in purification of phK2$^{v217}$ from AV12-hK2$^{v217}$ was used to purify hK2 polypeptides from the day 7 spent medium of AV12-hK2. This resulted in low yields of purified hK2 polypeptides which were unstable to the purification procedures.

hK2 polypeptides were partially purified using the above method, subjected to SDS/PAGE, electroblotted and subjected to N-terminal amino acid sequencing. This analysis indicated that the hK2 polypeptide in the spent medium of AV12-hK2 at day 7 has the sequence, IVGGWECEK (SEQ ID NO:40) at N-terminus. No competing sequence was evident from the profile of amino acids released sequentially by the Edman degradation procedure. By comparison to PSA, this sequence corresponds to mature hK2 (hK2). Amino acid analysis of this protein was also consistent with that of hK2.

This finding demonstrates that phK2$^{v217}$ was predominantly present in the serum-free spent medium of AV12-hK2$^{v217}$ at day 7, whereas predominantly hK2 was present in the serum-free spent medium of AV12-hK2 at day 7. To examine the form of hK2 present in the serum-free medium of AV12-hK2 at day 1 this material was partially purified by affinity purification using HK1G 586.1 mAbs. The 34 kD protein was transferred onto PVDF and was subjected to N-terminal analysis, yielding a sequence, VPLIQSRIVGG (SEQ ID NO:41). No competing sequence was evident from the profile of amino acids released sequentially by the Edman degradation procedure. Compared with PSA, this sequence corresponds to phK2. This suggests that the hK2 polypeptide is secreted as the pro form by both AV12-hK2 and AV12-hk2$^{v217}$ cells. However, while phK2$^{v217}$ is stable and is not converted to hK2$^{v217}$, phK2 is unstable and is easily converted to hK2 extracellularly.

EXAMPLE 6

Biosynthesis of hK2

Figure 9:
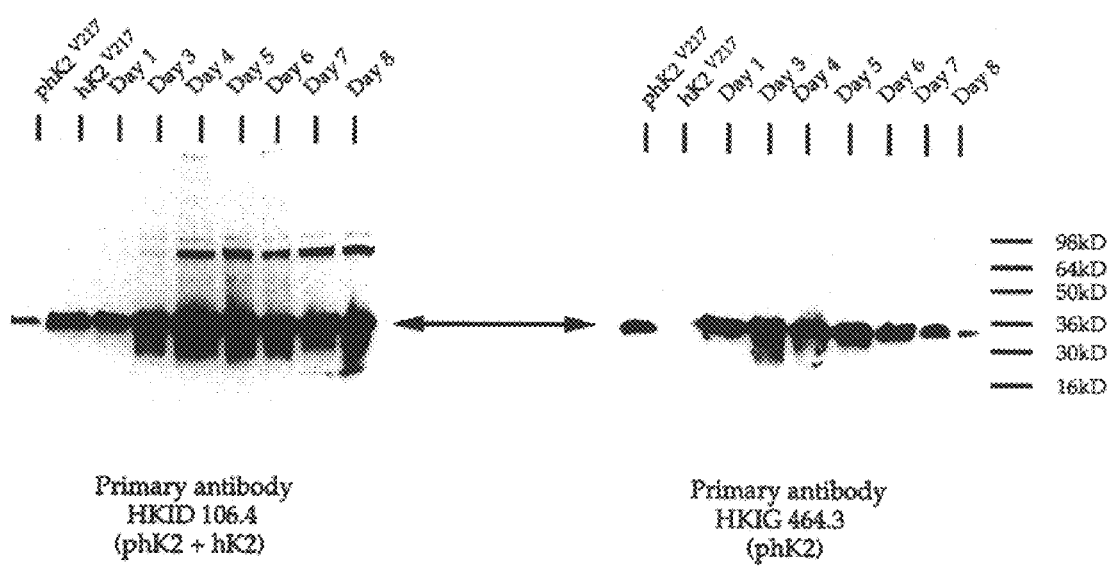
FIG. 9 represents a time course study of hK2 expression in AV12 cells. AV12-hK2 clone #27 was grown to ~60–70% confluency, then cells were washed with HBSS and serum free HH4 media was added. Spent medium was withdrawn each day, concentrated and subjected to SDS/PAGE on a 12% gel. Proteins were electroblotted and probed with monoclonal antibody HK1D 106.4, which detects both phK2 and hK2 (1:1000) or HK1G 464.3, which detects phK2 (1:1000), followed by goat anti-mouse IgG-HRP (1:500). The blot was developed with ECL (Amersham) according to the manufacturer's instructions. Purified phK2$^{v217}$ and hK2$^{v217}$ were used as controls. The position of hK2 is indicated by the arrow.

To further study the biosynthesis of hK2 in mammalian cells, a time course study was conducted where serum-free spent media from AV12-hK2 clone #27 was collected each day for 8 consecutive days, concentrated and subjected to SDS/PAGE. The proteins were transferred to nitrocellulose membrane and probed with either HK1D 106.4 or HK1G 464.3 mAbs (FIG. 9). As also shown in FIG. 9, HK1D 106.4 recognizes both phK2 and hK2 whereas HK1G 464.3 recognizes only phK2 as its epitope lies in −7 to +7 region of hK2. Expression of hK2 polypeptides (about 34 kD) peaked by day 3 and plateaued thereafter as detected by HK1D 106.4 mAbs. Two other immunoreactive bands migrating at about 70 kD and about 90 kD were also detected from day 4 onwards.

On the other hand, when the same samples were blotted and probed with HK1G 464.3, a gradual reduction in the level of hK2 was detected by day 4. By day 8, very low levels of hK2 were found in the spent medium. This result shows that phK2 is being secreted into the media by AV12-hK2 cells and is gradually converted to hK2 extracellularly. Curiously, the 70 kD and 90 kD bands were not observed with HK1G 464.3 mAbs indicating that these bands are either homo-oligomers of hK2 or are hK2 covalently complexed with a yet unknown protein(s). Even though the identity of these bands is not known at this time, they can serve as markers for the presence of hK2 in the spent media. In FIG. 9, purified phK2$^{v217}$ and hK2$^{v217}$ proteins were used as controls.

Figure 10:
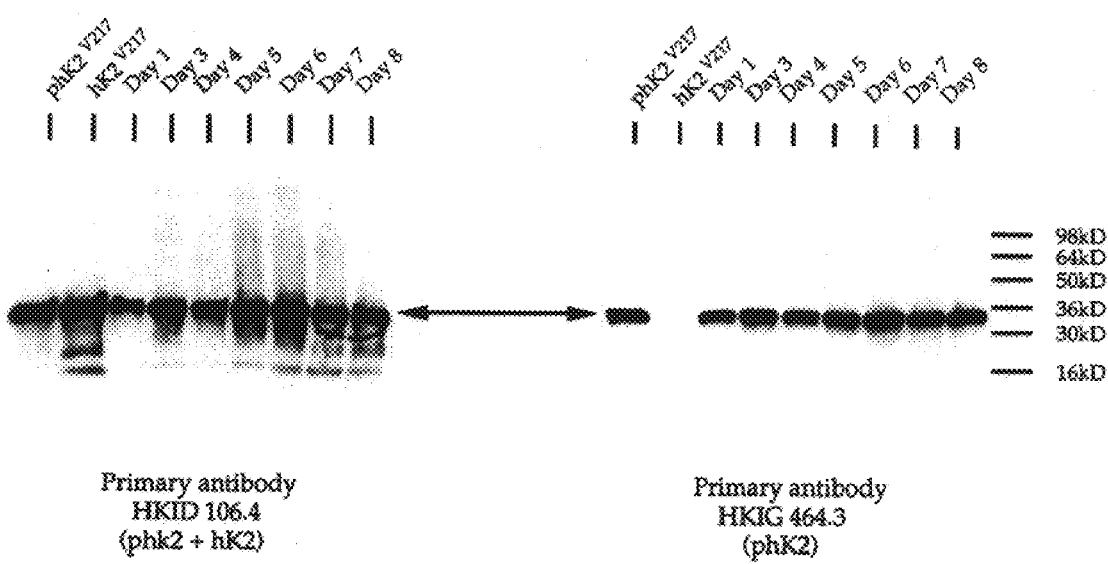
FIG. 10 represents a time course study of expression of the variant form of hK2 in transfected AV12 cells. At ~60–70% confluency, AV12-hK2$^{v217}$ cells were washed with HBSS and serum free HH4 media was added. Spent media was withdrawn each day, concentrated and subjected to SDS/PAGE on a 12% gel. Proteins were electroblotted and probed with monoclonal antibodies HK1D 106.4 and HK1G 464.3. Goat anti-mouse IgG-HRP (1:500) was used as a secondary antibody and the blot was developed with ECL (Amersham) according to the manufacturer's instructions. Purified phK2$^{v217}$ and hK2$^{v217}$ were used as controls. The position of hK2 is indicated by the arrow.

To study the biosynthesis of hK2$^{v217}$ in AV12 cells a similar time course study was conducted on AV12-hK2$^{v217}$ clone #2. As shown in FIG. 10, expression of hK2$^{v217}$ polypeptides peaked by day 3 and did not vary much from day 4 onwards, as detected by HK1D 106.4 mAbs. Similar results were obtained when the blot was probed with HK1G 464.3 mAbs (FIG. 10). This indicated that AV12-pGThK2$^{v217}$ clone #2 cells are expressing phK2$^{v217}$ from day 1 onwards and that for at least 8 days thereafter, this protein is not converted to the mature form. These results are in contrast with those of phK2, which is converted to hK2 if left in the media for 8 days, indicating that phK2$^{v217}$ is stable in media at 37° C. for 8 days.

Figure 11:
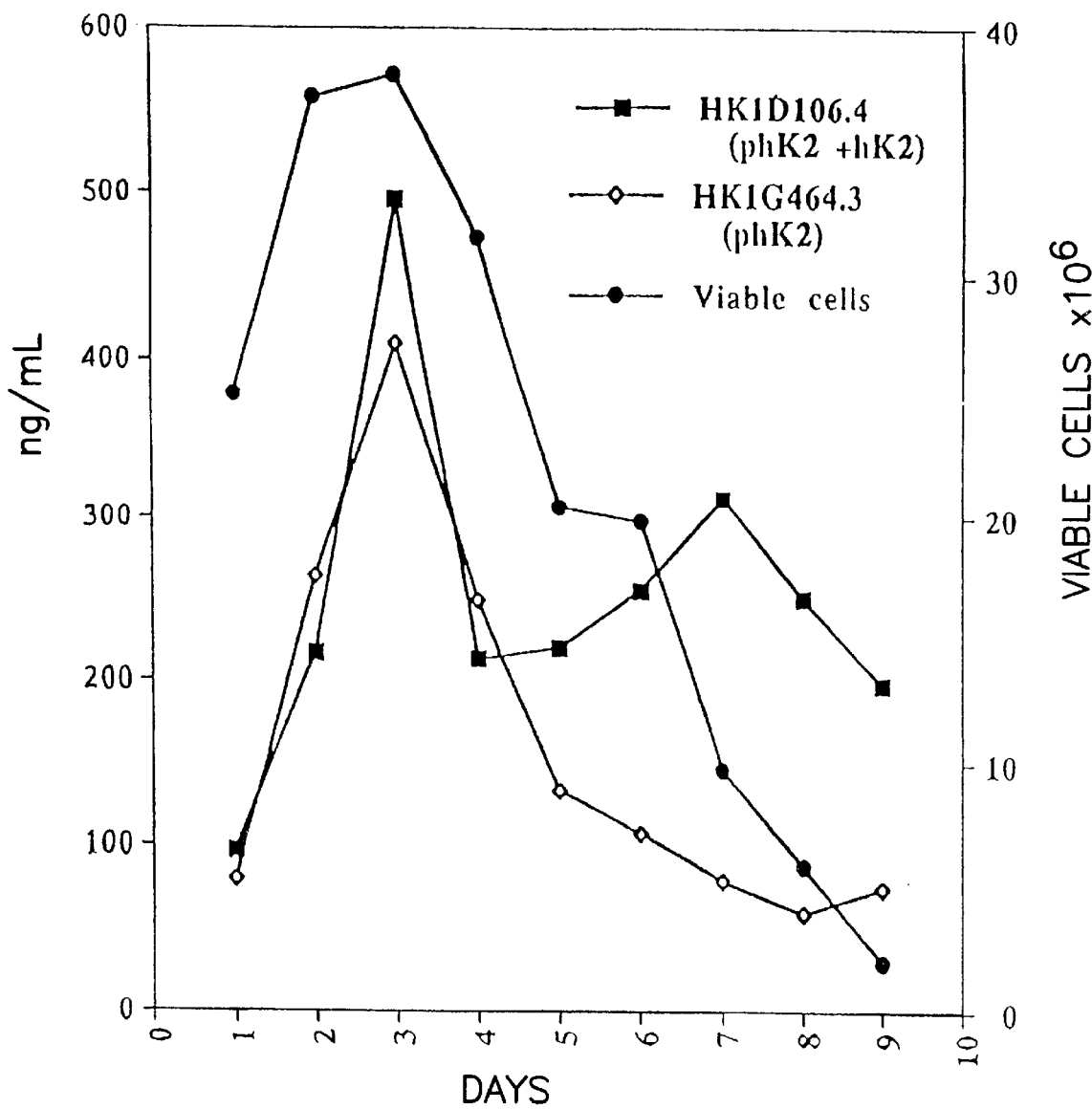

To study whether extracellular conversion of phK2 to hK2 correlates with the viability of AV12-hK2 clone #27 cells in culture, clone #27 cells were counted using trypan blue exclusion. Expression of hK2 in the spent medium was measured by ELISA using both HK1D 106.4 and HK1G464.3 mAbs. As shown in FIG. 11, the number of viable cells peaked at 38 million in culture by day 3 and gradually decreased thereafter. By day 8, the number of viable cells were reduced to less than 10 million. The expression of phK2 (measured by HK1G 464.3) also peaked by day 3 and gradually declined thereafter.

On the other hand, expression of hK2 (measured by HK1D 106.4) peaked by day 3 but plateaued thereafter. This result indicates that phK2 is secreted by AV12-hK2 cells and a fraction of it is gradually converted extracellularly to hK2 by day 4. Moreover, it shows that conversion of phK2 to hK2 clearly correlates with a decrease in cell viability, indicating that the extracellular proteases released by the dying cells may be one of the factor(s) responsible for this conversion. Expression of hK2 was highest at the point in which cells were most viable. A decrease in hK2 paralleled a decrease in cell viability, suggesting the hK2 is secreted by these cells, as opposed to being released following cell death and lysis. Also, a rise in hK2 corresponded to a drop in phK2, indicating that the pro form of hK2 was automatically converted to the mature form over time.

To examine the biosynthesis of hK2 in prostate carcinoma cells hK2 was expressed in DU145 and PC3 cell lines. DNA encoding pphK2 was cloned into plasmids pLNCX and pLNSX (Miller and Rosman, *Bio Techniques*, 7, 980 (1989)), under the control of the CMV and SV40 promoters, respectively. The resulting plasmids, pLNC-hK2 and pLNS-hK2, respectively, were transfected into PC3 and DU145 cells, respectively, and clones were selected in media containing G418. Clones expressing high levels of hK2 were selected (PC3-hK2 and DU145-hK2) by ELISA and Western blots.

To assess the level of hK2 and phK2 in the media, serum-free medium of PC3-hK2 and DU145-hK2 cells were subjected to Western blot analysis using HK1D 106.4 (hK2-specific) and HK1G 464.3 (phK2-specific) mAbs (FIG. 12). Results showed that phK2 is present in the spent medium of both DU145-hK2 and PC3-hK2. This indicates that in prostate carcinoma cells hK2 is secreted as phK2 and is converted to the mature form extracellularly. This finding confirms the results previously obtained with AV12 cells. Predominantly phK2 was detected in the spent medium of PC3-hK2 cells even after 7 days, however, predominately hK2 was present in the serum-free medium of DU145-hK2 starting from day 1. This is probably due to abundance of extracellular proteases in DU145 spent medium.

To examine whether the above results were limited to just one clone, 3 other independently isolated clones of AV12-hK2 and 4 other independently isolated clones of AV12-hK2$^{v217}$. were tested for the expression of hK2 polypeptides. Serum-free spent medium of the clones were collected at day 7 and tested for the expression of hK2 by Western blots using HK1D 106.4 (hK2-specific) and HK1G 464 (phK2-specific) mAbs (FIGS. 13 and 14). In all of the AV12-hK2 clones, HK1D 106.4 mAb detected not only the major 34 KD band ("hK2") but also the 70 kD and the 90 kD bands that are indicative of the presence of hK2 (FIG. 13). HK1G 464.3 detected very low levels of phK2 in all of the AV12-hK2 clones (FIG. 14). This result indicates that predominantly hK2 is present in the spent medium of all the AV12-hK2 clones verifying the biosynthetic mechanism established for AV12-hK2 #27 clone. The same analyses were used on AV12-hK2$^{v217}$ clones (FIG. 14). Results indicated that only phK2$^{v217}$ was present in the spent medium of these clones at day 7 verifying our findings with the AV12-hk2$^{v217}$ clone.

The above results collectively suggest that hK2 is expressed as the pro form in mammalian cells and is converted to mature form extracellularly by as yet unknown proteases. These results also suggest that phK2 may be present in the biological fluids and therefore can be a useful diagnostic marker for pCa and BPH.

EXAMPLE 7

Enzymatic Activity and Specificity of hK2 and hK2$^{v217}$

A small amount of hK2 was purified to sufficient purity to determine its enzymatic activity and substrate specificity. The general activity of hK2 was measured by determining its amidolytic activity chromogenically on p-nitroanilide derivatives of peptides (Table 3). The p-nitroanilide released by proteolytic digestion of these substrates is measured at absorbance $A_{405}$. The substrate methoxysuccinyl-Arg-Pro-Tyr-para-nitroanilide (MeO-Suc-R-P-Y-pNA) is used to measure chymotrypsin-like proteases which cleave at the phenylalanine. This substrate has been used previously to measure the activity of PSA (Christensson et al., *Eur. J. Biochem.*, 194, 755 (1990)). The substrate H-D-Pro-Phe-Arg-para-nitroanalide (P-F-R-pNA) is specific for trypsin-like proteases which cleave at arginine (R).

hK2 was found to have overall activity more than 10 times higher than hK2$^{v217}$ on P-F-R-pNA and neither protein showed an ability to hydrolyze MeO-Suc-R-P-Y-pNA, the chymotrypsin substrate. Other comparable substrates containing trypsin-like sites for cleavage (lysine, arginine) were also tested and hK2 was found to hydrolyze the substrate P-F-R-pNA with the highest rate. These findings indicate that hK2 has trypsin-like activity.

TABLE 3

Amidolytic Activity of hK2, hK2$^{v217}$, PSA and trypsin on Chromogenic Substrates

| Protease | MeO-Suc-R-P-Y-pNA xmol/min/µg/ml | P-F-R-pNA xmol/min/µg/ml |
| --- | --- | --- |
| hK2$^{v217}$ | 0 | 8.7 pmol |
| hK2 | 0 | 4.1 nmol |
| PSA | 13.3 pmol | 2.2 pmol |
| Trypsin | 3.8 pmol | 25.5 nmol |

The specificity of hK2 and hK2$^{217}$ was examined in more detail by the use of peptide substrates together with N-terminal amino acid sequence analysis to determine which peptide bonds had been hydrolyzed. FIG. 15 shows amidolytic activity on the polypeptide CALPEKPAVYTKV-VHYRKWIKDTIAAN SEQ. ID. NO:36, which has both potential trypsin and chymotrypsin cleavage sites. hK2$^{v217}$ cleaved at both a trypsin (R-K) and chymotrypsin (Y-R) site with the trypsin-like cleavage at a 2:1 ratio over the chymotrypsin-like cleavage. As a control in these experiments phK2$^{v217}$ was also incubated with this peptide and showed no amidolytic activity. hK2 showed specificity different than hK2$^{v217}$ towards this peptide substrate. No chymotrypsin-like specificity was seen for hK2 on this substrate and its activity was exclusive for the trypsin-like site (R-K). None of the other lysine (K) residues in this polypeptide were hydrolyzed indicating that the specificity of hK2 was exclusive for the arginine (R) residue.

As a control trypsin was also studied on this substrate and cleaved all lysine (K) and arginine (R) sites except the K-P bond which is known not to be a site suitable for trypsin cleavage. Trypsin cleaved the R-K site of the 210–236 substrate (peptide #1, FIG. 16) at rates approximately 4× faster than hK2 and about 4000× faster than hK2$^{v217}$. No chymotrypsin-like bonds were cleaved by trypsin. PSA cleaved the Y-R bond primarily. A minor trypsin-like activity on the R-K bond was also seen for PSA (FIG. 15). This was consistent with the minor trypsin-like activity previously seen for PSA on the chromogenic substrate (Table 2).

Several other peptide substrates were also incubated with hK2 and PSA (FIG. 16). In all of the peptides tested, hK2 had specificity only for selected arginines, and PSA primarily for selected tyrosine (Y), phenylalanine (F) and leucine (L) residues. Only peptide #1 in FIG. 16 was cleaved by hK2$^{v217}$ as detailed by the chromatograms in FIG. 15.

EXAMPLE 8

Activation of phK2$^{217}$ by hK2

The sequence of peptide #3 in FIG. 16 corresponds to amino acid residue -7 to +7 of phK2. This region contains the pro peptide, VPLIQSR, which is found as an N-terminal leader peptide in phK2$^{v217}$. As mentioned above, hK2 was able to cleave this peptide releasing the propeptide region, but hK2$^{v217}$ was not. To delineate if hK2 can cleave this pro sequence on a native substrate, its ability to convert phK2$^{v217}$ to hK2$^{v217}$ was monitored. phK2$^{v217}$ was incubated with 1% hK2 and the conversion was monitored by the HIC-HPLC method (FIG. 17A). Results showed that hK2 was able to convert phK2$^{v217}$ to hK2$^{v217}$, albeit at a rate about 30× slower than trypsin. When phK2$^{v217}$ was incubated with 40% hK2$^{v217}$, no difference in the ratios of the two hK2 forms was detected even after 6 hours (FIG. 17B). This corroborated previous observations with the peptide substrate and showed that, even on a native substrate, only hK2 and not hK2$^{v217}$ cleaved the pro region of hK2.

These results collectively demonstrate the stability of phK2$^{v217}$ and hK2$^{v217}$ upon extended incubation. When compared with hK2$^{v217}$, hK2 was shown to have a higher proteolytic activity, higher degree of specificity and, in particular, to have a specificity for the pro form of hK2 as demonstrated by activity on the pro peptide in FIG. 15 and its activity toward phK2$^{v217}$ in FIG. 17.

These results demonstrate a significant difference in enzymatic activity between hK2 and hK2$^{v217}$ and may help explain the low yields associated with attempts to purify hK2 from the medium compared to phK2$^{v217}$. Highly purified preparation of hK2 may not be stable due to autolysis as seen for other active proteases. These results further suggest that, in addition to immunological tests, enzymatic activity on hK2-specific substrates could be used to monitor the level of this protein in bodily fluids.

EXAMPLE 9

Formation of Inhibitor Complexes with hK2

PSA has been shown to form complexes with α2 macroglobulin (MG) and the serine protease inhibitor, antichymotrypsin (ACT). To explore its complex formation, hK2 was incubated with a series of common proteases present in human plasma (ACT, α2-antiplasmin, antithrombin III, and α1-antitrypsin (Travis and Salvesen, *Ann. Rev. Biochem.*, 52, 655 (1983)) and the mixtures were analyzed by Western blot (FIG. 18). Any covalent complex of hK2 with these serpins should result in about a 80–100 kD band on SDS/PAGE under reducing conditions.

ACT and α2-antiplasmin formed significant complexes with hK2 (FIG. 18, lane 1 and 2). Antithrombin III (lane 3) and α1-antitrypsin (α1 protease inhibitor, lane 4) formed no detectable complex with hK2. MG, a major component of blood plasma, also rapidly complexed with hK2 (lane 5). This complex corresponds to Mr of about 200 kD and 120 kD, which were also formed when PSA was incubated with purified MG (FIG. 18, lane 8, see below). It was particularly interesting that hK2 did not form complexes with α1-antitrypsin, even though this protein inhibits a wide range of trypsin-like proteases (Loebermann et al., *J. Mol. Biol.*, 177, 531 (1984); Carrell and Travis, *TIBS*, 10, 20 (1985)).

It was not surprising that hK2 formed a complex with α2-antiplasmin since this protein has arginine residues in its inhibitor active site (Hunt and Dayhoff, *Biochem. Biophy. Res. Comm.*, 95, 864 (1980); Chandra et al., *Biochemistry* 22, 5055 (1983); Potempa, et al., *Science*, 241, 699 (1985); Shieh et al., *J. Biol. Chem.*, 264, 13420 (1989); Mast et al., *Biochemistry*, 30, 1723 (1991)). However, it was also not expected that hK2 would form a complex with ACT, since ACT has a leucine in its inhibitor active site. Clearly the structural similarities between PSA and hK2 influence their complex formation with a common inhibitor even though their proteolytic specificity is entirely different as demonstrated in FIG. 16 and Table 2.

When spiked into human female serum hK2 formed a rapid complex with MG as detected by Western blot (FIG. 18). Lane 1 and lane 3 are hK2 and serum only controls, respectively. Lane 2 is hK2 incubated with ACT showing the 90 kD hK2-ACT complex and residual hK2. Lanes 4 and 5 are hK2 spiked into serum for minutes and 1 hour, respectively. Lane 6 is hK2 incubated with purified MG for 4 hours. Lane 7 is PSA spiked into serum for 15 minutes and Lane 8 is PSA incubated with purified MG for 4 hours.

These results show that MG is the major hK2 or PSA complex formed when hK2 or PSA are spiked into human serum in in vitro experiments. Since PSA complex with ACT is known to occur in the blood serum of patients with prostate disease, it is believed that hK2 present in serum would also form some level of ACT complex.

Discussion

The in vivo protein processing and secretion mechanisms for PSA or hK2 are not known. The results presented herein show that phK2 is secreted by AV12-hK2, DU145-hK2, and PC3-hK2 cells, indicating that hK2 is normally secreted as phK2 and the propeptide is cleaved extracellularly. This suggests that phK2 exists in biological fluids and thus could be a useful diagnostic marker for pCa or BPH.

Both the mutant form of hK2 (hK2$^{v217}$) and the wild type form of hK2 were purified from AV12 cells. hK2 was very unstable to the purification procedures employed which, as found with other proteases, may be due to its autocatalytic property, and makes it very difficult to purify hK2 or phK2 in quantities sufficient for use as immunogens and calibrators. In contrast, phK2$^{v217}$ is highly stable and is converted to hK2$^{v217}$, which was also stable, by trypsin digestion. Purified pHK2$^{v217}$ and hK2$^{v217}$ provided immunogens to generate mAbs specific for hK2 and phK2.

EXAMPLE 10

Immunoreactivity of Monoclonal Antibody 586 with Prostate Tissue

Immunohistochemistry of normal prostate tissue with HK1523 showed staining in epithelia but not stroma. Moreover, hK2 expression is prostate-specific as other tissues, e.g., kidney and pancreas, showed no staining. To determine if hK2 is expressed in prostate tissue and, if so, is correlated with prostate cancer, 264 radical prostatectomy specimens, of which 257 were from untreated patients (FIG. 20) and 7 were from androgen deprivation therapy treated patients (FIG. 21), were analyzed in a comparative study. Each specimen was analyzed for the cytoplasmic expression of hK2 in areas with benign epithelium, high grade prostatic intraepithelial neoplasia (PIN) and adenocarcinoma.

Prostate tissue was weighed, measured in three dimensions and inked. The apex and base were amputated at a thickness of 4–5 mm and serially sectioned at 3 mm. The remaining prostate was serially sectioned at 4–5 mm intervals by knife perpendicular to the long axis of the gland from the apex of the prostate to the tip of the seminal vesicles. Transverse sections were prepared and stained with hematoxylin and eosin. A single slice of the radical prostatectomy of each patient which encompassed cancer and benign tissue was fixed in 10% neutral buffered formalin and embedded in paraffin by methods well known to the art.

Tissue sections on slides were deparaffinized by immersion in xylene and then in 95% ethanol. Endogenous peroxidase activity was blocked by incubating sections for 10 minutes in methanol/$H_2O_2$ and then rinsing sections in tap water. Sections were then placed in 10 mM citrate buffer, pH 6.0, and steamed for 30 minutes. Sections were cooled for 5 minutes prior to rinsing in cold running tap water. Nonspecific protein binding was blocked by incubating sections for 10 minutes with 5% goat serum. Slides were then gently drained.

Primary antibody, hK1G586 or PSM773 at 0.5 μg/ml, was added to the sections for 30 minutes at room temperature and then the sections were rinsed with tap ater. Tissue sections were then incubated with biotinylated rabbit anti-mouse antibody for one hour and rinsed with water. Sections were incubated with peroxidase conjugated streptavidin (1:500) for 30 minutes, then rinsed in tap water. Subsequently, sections were incubated with 3-amino-9-ethylcarbamoyl (ABC) chromagen solution for 15 minutes prior to rinsing in tap water. Sections were then counterstained with mercury-free hematoxylin for one minute and rinsed for 5 minutes in running water. Slides were mounted with aqueous mounting media (glycerol gelatin). The percentage of cells staining was recorded at 10% increments from 0–100% for benign epithelium, high grade PIN and adenocarcinoma.

Benign atrophic glands showed the least amount of staining, particularly in areas of inflammation, in which there was virtually no immunoreactivity. In hyperplastic acini and benign acini with no evidence of atrophy, there was moderate to intense immunoreactivity, usually appearing in a granular pattern in the secretory luminal cell layer just above the nuclei, often extending to the luminal surface. There was no staining of the uroepithelium of the urethra or the viva montanum, although the underlying glands often showed immunoreactivity. Basal cells were usually negative.

Specimens with high grade PIN showed intense immunoreactivity throughout the cytoplasm and in the cytoplasmic apical blebs in a majority of cases. There was no apparent difference in the immunoreactivity among the different patterns of PIN except for the cribiform pattern which was usually decreased in intensity centrally when compared to the periphery.

Carcinoma specimens showed intense cytoplasmic reactivity in virtually all cases. Cells with abundant cytoplasmic vacuoles showed less staining, including signet ring cells and areas of mucin; otherwise the cytoplasm was intensely stained. The greatest intensity was observed in the highest grade adenocarcinoma (Gleason pattern 4) which showed immunoreactivity in virtually every case. Foci with cribiform carcinoma were similar to cribiform PIN in that there was a greater intensity in the periphery than centrally. The peripheral edge and the advancing edge of the carcinomas were always intensely immunoreactive.

In seven specimens from patients who had undergone androgen deprivation therapy, there was little or no immunoreactivity in the majority of benign atrophic acini, although PIN and adenocarcinoma occasionally showed intense cytoplasmic staining.

A summary of the number of cells staining with monoclonal antibody HK1G586 in the benign epithelium, high grade PIN and adenocarcinoma is shown in Table 4. Pair wise analysis, i.e., benign versus PIN, benign versus carcinoma, and PIN versus carcinoma, revealed significant differences for each category (P<0.001, Spearman Rank Correlation).

TABLE 4

| | Immunoreactivity with hK1G586 | |
|---|---|---|
| | mean | standard deviation % |
| Benign epithelium | 44.3% | 10–90 |
| High grade PIN | 69.1% | 20–100 |
| Adenocarcinoma (untreated) | 80.0% | 20–100 |

Thus, an increase in cytoplasmic hK2 expression in prostate tissue is correlated with prostatic neoplasia and prostate cancer. Although the data from prostate obtained from androgen deprivation therapy treated patients is not statistically significant due to the small sample size, there is a decrease in hK2 expression in benign epithelium, high grade PIN and adenocarcinoma in these patients relative to untreated patients. Thus, an increase in hK2 expression in prostate is a novel marker for high grade PIN and prostate cancer.

EXAMPLE 11

RT-PCR Detection of hK2 RNA in Prostate Cancer Cells and Peripheral Blood of Prostate Cancer Patients Because a large percentage of prostate cancers are understaged, it is of interest to detect hK2 expressing cells present in tissue biopsies, e.g., prostate capsule, bone marrow or lymph node, or in physiological fluid, e.g., blood, serum or seminal fluid. Such a detection method preferably can detect a single hK2 expressing cell in a large number of non-hK2 expressing cells. Preferably, the method can detect a single hK2 expressing cell in a sample comprising at least about $10^4$, more preferably at least about $10^6$, or even more preferably $10^7$, cells. To provide such a sensitive detection method, a reverse transcriptase-polymerase chain reaction (RT-PCR) specific for hK2 transcripts is employed.

A. LNCaP Cell Line

To determine the sensitivity of detection of an hK2-specific transcript by RT-PCR, cells of the human PSA- and hK2-expressing LNCaP cell line were serially diluted in samples of buffy coat cells. The buffy coat cells were isolated from whole blood from normal females and males. Venous blood (5–7 ml) was collected in citrate-dextrose tubes. Samples were centrifuged at 1000×g for 15 minutes at 4° C. Buffy coat cells were recovered from the top of the cell pellet.

The mixture of buffy coat cells and LNCaP cells was centrifuged at 1,500 rpm for five minutes, and RNA extracted from the pelleted cells. RNA was isolated by an acidic phenol-chloroform-guanidium thiocyanate method (Chomczynski et al., Anal. Biochem., 162, 156 (1987)). RNA samples were further extracted with chloroform-butanol (4:1; v/v) to remove residual heme, which can inhibit both reverse transcription and polymerase chain reactions. The isolated RNA was then treated with RNase-free DNase.

To prepare first strand cDNAs, an aliquot containing 1 µg of total RNA was added to a reverse transcription reaction containing 100 pmol of a PSA-specific oligonucleotide primer (5'TCATCTCTGTATCC 3'; SEQ ID NO:13) or 100 pmol of an hK2-specific oligonucleotide primer (5'GAGTAAGCTCTA 3'; SEQ ID NO:14), and Moloney murine leukemia virus reverse transcriptase (GIBCO BRL), and brought to a final volume of 25 µL (50 mM Tris-HCl, pH 8.3, 75 mM KCl, 3 mM MgCl$_2$, 10 mM dithiothreitol, 0.5 mM each dNTP, and 800 U Moloney murine leukemia virus reverse tranasscriptase). The reaction was incubated at 42° C. for fifteen minutes and the enzyme was heat inactivated at 95° C. for fifteen seconds.

To amplify PSA first strand cDNAs, 10 µl of the PSA-specific oligonucleotide primed first strand cDNAs was amplified in a PCR (0.2 mM each dNTP, 0.5 U AMPLITAQ polymerase, 50 mM KCl, 10 mM Tris-HCl, pH 8.3, 1.5 mM MgCl$_2$, 0.1% (w/v) gelatin) with a PSA-specific primer pair. The PSA PCR employed 50 pmol of PSA-1 (5'GATGACTCCAGCCACGACCT 3'; SEQ ID NO:15) and 50 pmol of PSA-2 (5'CACAGACACCCCATCCTATC 3'; SEQ ID NO:16). To amplify hK2 first strand cDNAs, 10 µl of the hK2 PSA-specific oligonucleotide primed first strand cDNAs was amplified in a PCR (0.2 mM each dNTP, 0.5 U AMPLITAQ polymerase, 50 mM KCl, 10 mM TriS-HCl, pH 8.3, 1.5 mM MgCl$_2$, 0.1% (w/v) gelatin) with an hK2-specific primer pair. The hK2 PCR employed 50 pmol of hK2-1 (5'GAGGGTTGTGTACAGTCATGGAT 3'; SEQ ID NO:17) and 50 pmol of hK2-2 (5'ACACACTGAAGACTCCTGGGGCG 3'; SEQ ID NO:18)).

The cycling parameters employed were: thirty-five to forty cycles of 94° C. for 1 minute; 58° C. (PSA) or 60° C. (hK2) for 90 seconds, and 72° C. for seconds. The final cycle was at 72° C. for ten minutes. Aliquots of the reaction were electrophoresed on 1.0% agarose gels The gels were stained with ethidium bromide and were viewed under ultraviolet light. Some of the amplified products were excised from the gel and subcloned into a pCRII vector (Invitrogen, San Diego, Calif.) for sequencing.

The PSA-specific PCR yielded a 710 bp product while the hK2-specific PCR yielded a 405 bp product. The results of the dilution analysis showed that PSA and hK2 RNA was detectable at approximately 1 LNCaP cell in $10^6$ and $10^7$ white blood cells, respectively (FIG. 22A). This result was unexpected because the RT-PCR detected LNCaP-derived hK2 transcripts at a ten fold high dilution than LNCaP-derived PSA transcripts.

B. Prostate Cancer Patients

The blood from six patients with prostate cancer and from two normal males was analyzed by RT-PCR. Buffy coat cells and isolated RNA were obtained from all eight males, and RT-PCR was performed, as described above. The six prostate cancer patients included one with clinical stage B prostate cancer, two with known metastatic disease (clinical stage D2) and three with pathological stage C. Prostate cancer pathological stages A–C are localized forms of prostate cancer. Pathological stage D1 is prostate cancer which has spread to the nodes (nodal metastases). Pathological stage D2 is systemic (systemic metastases) prostate cancer. For a further description of the pathological stages of prostate cancer, see Moreno et al. (*Cancer Res.*, 52, 6110 (1992)), Deguchi et al. (*Cancer Res.*, 53, 5350 (1993)) and Katz et al. (*Urology*, 43, 765 (1994)).

The results showed that 67% of the prostate cancer patients expressed hK2, 17% expressed PSA, and 17% expressed both hK2 and PSA. No detectable levels of PSA or hK2 RNA were found in normal controls.

Thus, the detection of hK2 RNA may serve as a useful marker for early detection of micrometastasis of prostate cancer.

EXAMPLE 12

RT-PCR Detection of hK2 RNA in the Peripheral Blood of Patients with Localized Prostate Cancer To further test the clinical utility of RT-PCR detection of hK2 RNA as a staging tool for men with clinically localized prostate cancer, two sets of primer pairs were prepared. The 3'end of each primer had maximum non-homology to hK1 and hK3 (see, for example, FIG. 25). An example of a primer set useful in this regard is a set which spans intron 4 of the hK2 gene and in which the 3' primer includes sequences which are complementary to at least a portion of sequence in the 3' untranslated region of hK2 mRNA.

For reverse transcriptase reactions, 1 μg RNA or serial dilutions of cDNA were used for the synthesis of the first strand of cDNA with SUPERSCRIPT II reverse tranascriptase (RT) and random primers p(dN)6 (Boehringer Maniheim). The annealing mixture was incubated at room temperature for 15 minutes and after adding RT, incubated at 37° C. for 75 minutes. RT was heat inactivated at 95° C. for 15 seconds.

For PCR, reaction conditions were essentially the same as those previously reported (*Urology*, 43, 765 (1994)) but included 2 μM dig-11-dUTP and 0.4 μM hK2-2 primers. The PCR mixture was preheated to 80° C. before 10 μl RT products were added and cycling begun. 35 cycles were performed with the following cycling parameters: denaturation at 94° C. for 1 minute, annealing at 66° C. for 1 minute and extension at 72° C. for 2 minutes. 12 μl of each PCR product was loaded on the 2% NuSieve agarose gel. After electrophoresis, PCR products were transferred onto a positively charged nylon membrane (Boehringer Mannheim) with pressure blotter (Bio-Rad, 8 Hg, 2 hours). The membrane then was probed using the Genius System (Boehringer Mannheim). To assess RNA integrity, a second RT-PCR reaction using GAPDH primers was employed.

To determine the specificity of the primer sets, hK2 and hK3 (PSA) cDNA templates were employed in RT-PCR. The results showed that each primer set was highly specific for hK2 and that there was no detectable cross-reactivity (FIGS. 23 and 24). Moreover, RT-PCR analyses of serial dilutions of hK2 cDNA in normal lymphoblast RNA demonstrated that 5 copies of hK2 cDNA could be detected with the primer set. One primer pair was selected for further study (FIG. 25; hK2–3 (SEQ ID NO:27) and hK2–4 (SEQ ID NO:28)). The other primer pair corresponds to hK2–5 (SEQ ID NO:34; 5'AAAGCCTTAGACCAGATGAA 3') and hK2–6 (SEQ ID NO:35; 5'CCATTTCAGAAACATTGGCA 3')).

To determine the sensitivity of primers hK2–3 and hK2–4, these primers were employed in RT-PCR of RNA extracted from serial dilutions of LNCaP cells in lymphoblasts. The data showed that this primer pair could detect 1 LNCaP cell in $10^9$ lymphoblasts (FIG. 26). Surprisingly, two hK2 specific PCR products were observed in the PCR products from LNCaP cells. The larger product is approximately 680 bp in length, while the smaller product is approximately 640 bp in length. The larger product corresponds to an hK2 splice variant RNA which is generated by the use a splice donor site in intron 4 (*Mol. Cell. Endocrinol.*, 79, 181 (1991)). Sequence analysis of the smaller PCR product confirmed that it corresponded to the wild-type hK2 mRNA.

To ascertain whether primers hK2–3 and hK2–4 could detect hK2 RNA in patient samples, RT-PCR analyses were conducted which employed these primers and RNA extracted from peripheral blood samples from 71 patients with a normal DRE and a PSA of $\leq 3$ (mean 1.09±0.60, median 1.0). Mononuclear cells were separated from peripheral blood samples which had been collected in VACU-TAINER CPT tubes from patients. The cells were lysed with an acid pH guanidine lysis buffer and stored at −80° C. until processing. RNA was extracted using the acid phenol-chloroform method. Alternatively, RNA was extracted using a modified protocol which replaces the initial ethanol precipitation by application to Qiagen-RNeasy spin columns (QIAGEN). For the determination of assay sensitivity, either hK2 cDNA or LNCAP cells were serially diluted into immortalized human lymphoblasts (ATCC RPMI 7666) and the RNA extracted as described above. The quantity and quality of each RNA specimen was checked by spectrophotometry and gel electrophoresis. RNA was ethanol precipitated and stored at −80° C. in 70% ethanol and 85 mM NaOAc (pH 4.2).

Nineteen (26.8%) of these samples tested positive for the larger hK2 PCR product and 18 (25.4%) of the samples tested positive for the smaller hK2 PCR product (FIG. 27). In addition, 6 (85.7%) of 7 samples from men with metastatic prostate cancer were positive for hK2 RNA by RT-PCR. One of these positive samples had previously tested negative for PSA RNA by RT-PCR. Moreover, 5 of the samples from metastatic prostate cancer patients had both the large and the small hK2 PCR product, while the other sample had only the larger PCR product. The results showed that the presence of hK2 RNA in peripheral blood correlates with metastatic prostate cancer.

To determine whether the preoperative presence of hK2 RNA in peripheral blood correlates with post-operative pathological stage or recurrence of disease, preoperative peripheral blood samples were obtained from 228 patients undergoing radical retropubic prostatectomy for cT1–T2c prostate cancer. Over 150 clinical, staging, and pathological variables were abstracted for each patient. Follow-up information including postoperative complications, continence and potency status, as well as patient status, clinical disease status, most recent PSA, and additional postoperative therapy, including hormonal or radiation therapy are recorded and updated for each patient every 3 months in the first year after surgery, every 6 months in postoperative years 2–5, and yearly thereafter.

Control patients (see FIG. 27) were part of a free year-round prostate cancer screening program. Each of these patients filled out a consent form and comprehensive questionnaire, was phlebotomized for a PSA blood test, and then underwent a digital rectal examination. Patient follow-up was obtained 8 weeks after screening either by telephone or by standard follow-up questionnaires mailed to each participant. Patients presenting for screening with a normal DRE and a PSA of ≦2.0 (mean 0.96, median 1.1) were divided into 4 cohorts of 25 patients. Based on these parameters, these patients, though not biopsied, have a low risk of harboring clinically detectable prostate cancer. An 8 mL CPT tube of venous blood for buffy coat isolation and RT-PCR PSA and hK2 analysis, in addition to the standard 5 ml tube for serum PSA, was collected from each participant.

A univariate analysis and a multivariate analysis of the results obtained showed that, in addition to the typical preoperative predictive variables, i.e., UICC stage, preoperative PSA and biopsy Gleason's score, RT-PCR status of the smaller hK2 PCR product, which corresponds to the wild-type (native) hK2 amplifed product, was a statistically significant prognostic indicator for predicting lymph node positive (LN+) disease (p=0.0269) (Tables 5–7). The use of the Partin nomogram to predict LN+ status was previously shown to yield a c value (area under the ROC curve) of 0.768. The use of information which includes the presence of the smaller hK2 PCR product to predict LN+ status yielded a c value of 0.855.

A follow up study to monitor the risk of PSA progression during a time period including and beyond the median follow up time for radical prostatectomy (median follow up is 15.1 months) can determine the extent of the correlation between the preoperative presence of the either or both hK2 PCR products and the risk of PSA progression (FIG. 28).

TABLE 5

Clinically localized prostate cancer (n = 228)

| Preop RT-PCR- hK2 Status | Final Pathologic Stage | | | |
|---|---|---|---|---|
| | OC | ECE | SVI+ | LN+ |
| hk2-L + | 35/154(23%) | 14/47(30%) | 2/16(13%) | 6/11(55%) |
| hK2-U + | 38/154(25%) | 12/47(26%) | 3/16(19%) | 5/11(45%) |
| hK2-L + and hK2-U + | 27/154(18%) | 11/47(23%) | 2/16(13%) | 4/11(36%) |

TABLE 5-continued

Clinically localized prostate cancer (n = 228)

| Preop RT-PCR- hK2 Status | Final Pathologic Stage | | | |
|---|---|---|---|---|
| | OC | ECE | SVI+ | LN+ |
| hK2-L + or hK2-U + | 46/154(30%) | 15/47(32%) | 3/16(19%) | 7/11(64%) |

OC = organ confined (pT$_2$), ECE = extracapsular expansion, SVI+ = seminal vesicle involvement

TABLE 6

Multivariate Analysis: Preoperative clinical parameters and prediction of LN status (n = 211)

| Preop Clinical Parameter | p value |
|---|---|
| UICC stage | 0.1883 |
| Preop PSA | 0.4609 |
| Biopsy Gleason Score | 0.0112 |
| RT-PCR-bK2-L status | 0.0269 |

TABLE 7

Univariate Analysis: hK2 status and prediction at final pathologic stage

| Variable | ECE | SVI | LN+ |
|---|---|---|---|
| hK2-U + | Not significant | Not significant | Not significant |
| hK2-L + | Not significant | Not significant | 0.019 |
| hK2U + or hK2L + | Not significant | Not significant | 0.016 |

Thus, preoperative RT-PCR for hK2 may be useful as a staging tool for men with clinically localized prostate cancer. In particular, the preoperative presence hK2 RNA in peripheral blood may be useful to predict final pathologic stage or PSA-progression free survival.

The invention is not limited to the exact details shown and described, for it should be understood that many variations and modifications may be made while remaining within the spirit and scope of the invention defined by the claims.

What is claimed is:

1. An oligonucleotide which consists of SEQ ID NO:27 or the complete complement of SEQ ID NO:27.

2. An oligonucleotide which consists of SEQ ID NO:28 or the complete complement of SEQ ID NO:28.

3. A diagnostic kit for detecting hK2 RNA in a physiological sample suspected of containing hK2 RNA, which comprises packaging containing (a) a first oligonucleotide, wherein the oligonucleotide consists of SEQ ID NO:17 or SEQ ID NO:27, and (b) a second oligonucleotide, wherein the oligonucleotide consists of SEQ ID NO:14, SEQ ID NO:18, or SEQ ID NO:28.

4. The diagnostic kit of claim 3 wherein the second oligonucleotide consists of SEQ ID NO:14.

5. The diagnostic kit of claim 3 wherein the first oligonucleotide consists of SEQ ID NO:17.

6. The diagnostic kit of claim 3 wherein the second oligonucleotide consists of SEQ ID NO:18.

7. An oligonucleotide selected from the group consisting of an oligonucleotide which is the complete complement of SEQ ID NO:14, SEQ ID NO:17, the complete complement of SEQ ID NO:17, SEQ ID NO:18 and the complete complement of SEQ ID NO:18.

8. The oligonucleotide of claim 7 which consists of SEQ ID NO:14.

9. The oligonucleotide of claim 7 which consists of SEQ ID NO:17.

10. The oligonucleotide of claim 7 which consists of SEQ ID NO:18.

* * * * *

SEQUENCE LISTING

<160> NUMBER OF SEQ ID NOS: 49

<210> SEQ ID NO 1
<211> LENGTH: 237
<212> TYPE: PRT
<213> ORGANISM: Homo sapiens

<400> SEQUENCE: 1

Ile Val Gly Gly Trp Glu Cys Glu Lys His Ser Gln Pro Trp Gln Val
 1               5                  10                  15

Ala Val Tyr Ser His Gly Trp Ala His Cys Gly Gly Val Leu Val His
            20                  25                  30

Pro Gln Trp Val Leu Thr Ala Ala His Cys Leu Lys Lys Asn Ser Gln
        35                  40                  45

Val Trp Leu Gly Arg His Asn Leu Phe Glu Pro Glu Asp Thr Gly Gln

```
                50              55              60
Arg Val Pro Val Ser His Ser Phe Pro His Pro Leu Tyr Asn Met Ser
 65                      70                      75                      80

Leu Leu Lys His Gln Ser Leu Arg Pro Asp Glu Asp Ser Ser His Asp
                     85                      90                      95

Leu Met Leu Leu Arg Leu Ser Glu Pro Ala Lys Ile Thr Asp Val Val
                100                     105                     110

Lys Val Leu Gly Leu Pro Thr Gln Glu Pro Ala Leu Gly Thr Thr Cys
                115                     120                     125

Tyr Ala Ser Gly Trp Gly Ser Ile Glu Pro Glu Glu Phe Leu Arg Pro
                130                     135                     140

Arg Ser Leu Gln Cys Val Ser Leu His Leu Leu Ser Asn Asp Met Cys
145                     150                     155                     160

Ala Arg Ala Tyr Ser Glu Lys Val Thr Glu Phe Met Leu Cys Ala Gly
                165                     170                     175

Leu Trp Thr Gly Gly Lys Asp Thr Cys Gly Gly Asp Ser Gly Gly Pro
                180                     185                     190

Leu Val Cys Asn Gly Val Leu Gln Gly Ile Thr Ser Trp Gly Pro Glu
                195                     200                     205

Pro Cys Ala Leu Pro Glu Lys Pro Ala Val Tyr Thr Lys Val Val His
                210                     215                     220

Tyr Arg Lys Trp Ile Lys Asp Thr Ile Ala Ala Asn Pro
225                     230                     235

<210> SEQ ID NO 2
<211> LENGTH: 711
<212> TYPE: DNA
<213> ORGANISM: Homo sapiens

<400> SEQUENCE: 2
attgtgggag gctgggagtg tgagaagcat tcccaaccct ggcaggtggc tgtgtacagt      60
catggatggg cacactgtgg gggtgtcctg gtgcacccc  agtgggtgct cacagctgcc     120
cattgcctaa agaagaatag ccaggtctgg ctgggtcggc acaacctgtt tgagcctgaa     180
gacacaggcc agagggtccc tgtcagccac agcttccac  acccgctcta caatatgagc     240
cttctgaagc atcaaagcct tagaccagat gaagactcca gccatgacct catgctgctc     300
cgcctgtcag agcctgccaa gatcacagat gttgtgaagg tcctgggcct gcccacccag     360
gagccagcac tggggaccac ctgctacgcc tcaggctggg gcagcatcga accagaggag     420
ttcttgcgcc caggagtct  tcagtgtgtg agcctccatc tcctgtccaa tgacatgtgt     480
gctagagctt actctgagaa ggtgacagag ttcatgttgt gtgctgggct ctggacaggt     540
ggtaaagaca cttgtggggg tgattctggg ggtccacttg tctgtaatgg tgtgcttcaa     600
ggtatcacat catggggccc tgagccatgt gccctgcctg aaaagcctgc tgtgtacacc     660
aaggtggtgc attaccggaa gtggatcaag gacaccatcg cagccaaccc c              711

<210> SEQ ID NO 3
<211> LENGTH: 261
<212> TYPE: PRT
<213> ORGANISM: Homo sapiens

<400> SEQUENCE: 3

Met Trp Asp Leu Val Leu Ser Ile Ala Leu Ser Val Gly Cys Thr Gly
 1               5                       10                      15

Ala Val Pro Leu Ile Gln Ser Arg Ile Val Gly Gly Trp Glu Cys Glu
```

```
                    20                  25                  30
Lys His Ser Gln Pro Trp Gln Val Ala Val Tyr Ser His Gly Trp Ala
            35                  40                  45
His Cys Gly Gly Val Leu Val His Pro Gln Trp Val Leu Thr Ala Ala
        50                  55                  60
His Cys Leu Lys Lys Asn Ser Gln Val Trp Leu Gly Arg His Asn Leu
65                  70                  75                  80
Phe Glu Pro Glu Asp Thr Gly Gln Arg Val Pro Val Ser His Ser Phe
                85                  90                  95
Pro His Pro Leu Tyr Asn Met Ser Leu Leu Lys His Gln Ser Leu Arg
            100                 105                 110
Pro Asp Glu Asp Ser Ser His Asp Leu Met Leu Leu Arg Leu Ser Glu
        115                 120                 125
Pro Ala Lys Ile Thr Asp Val Val Lys Val Leu Gly Leu Pro Thr Gln
        130                 135                 140
Glu Pro Ala Leu Gly Thr Thr Cys Tyr Ala Ser Gly Trp Gly Ser Ile
145                 150                 155                 160
Glu Pro Glu Glu Phe Leu Arg Pro Arg Ser Leu Gln Cys Val Ser Leu
                165                 170                 175
His Leu Leu Ser Asn Asp Met Cys Ala Arg Ala Tyr Ser Glu Lys Val
            180                 185                 190
Thr Glu Phe Met Leu Cys Ala Gly Leu Trp Thr Gly Gly Lys Asp Thr
        195                 200                 205
Cys Gly Gly Asp Ser Gly Gly Pro Leu Val Cys Asn Gly Val Leu Gln
    210                 215                 220
Gly Ile Thr Ser Trp Gly Pro Glu Pro Cys Ala Leu Pro Glu Lys Pro
225                 230                 235                 240
Ala Val Tyr Thr Lys Val Val His Tyr Arg Lys Trp Ile Lys Asp Thr
                245                 250                 255
Ile Ala Ala Asn Pro
            260

<210> SEQ ID NO 4
<211> LENGTH: 832
<212> TYPE: DNA
<213> ORGANISM: Homo sapiens

<400> SEQUENCE: 4
ggatccagca tgtgggacct ggttctctcc atcgccttgt ctgtggggtg cactggtgcc      60
gtgcccctca tccagtctcg gattgtggga ggctgggagt gtgagaagca ttcccaaccc    120
tggcaggtgg ctgtgtacag tcatggatgg cacactgtg ggggtgtcct ggtgcacccc     180
cagtgggtgc tcacagctgc ccattgccta agaagaata gccaggtctg ctgggtcgg      240
cacaacctgt ttgagcctga agacacaggc cagagggtcc ctgtcagcca cagcttccca    300
cacccgctct acaatatgag ccttctgaag catcaaagcc ttagaccaga tgaagactcc    360
agccatgacc tcatgctgct ccgcctgtca gagcctgcca agatcacaga tgttgtgaag    420
gtcctgggcc tgcccaccca ggagccagca ctggggacca cctgctacgc ctcaggctgg    480
ggcagcatcg aaccagagga gttcttgcgc cccaggagtc ttcagtgtgt gagcctccat    540
ctcctgtcca atgacatgtg tgctagagct tactctgaga aggtgacaga gttcatgttg    600
tgtgctgggc tctggacagg tggtaaagac acttgtgggg gtgattctgg gggtccactt    660
gtctgtaatg gtgtgcttca aggtatcaca tcatggggcc ctgagccatg tgccctgcct    720
```

```
gaaaagcctg ctgtgtacac caaggtggtg cattaccgga agtggatcaa ggacaccatc    780
gcagccaacc cctgagtgcc cctgtcccac ccctacctct agtaaactgc ag            832
```

<210> SEQ ID NO 5
<211> LENGTH: 244
<212> TYPE: PRT
<213> ORGANISM: Homo sapiens

<400> SEQUENCE: 5

```
Val Pro Leu Ile Gln Ser Arg Ile Val Gly Gly Trp Glu Cys Glu Lys
  1               5                  10                  15

His Ser Gln Pro Trp Gln Val Ala Val Tyr Ser His Gly Trp Ala His
             20                  25                  30

Cys Gly Gly Val Leu Val His Pro Gln Trp Val Leu Thr Ala Ala His
         35                  40                  45

Cys Leu Lys Lys Asn Ser Gln Val Trp Leu Gly Arg His Asn Leu Phe
     50                  55                  60

Glu Pro Glu Asp Thr Gly Gln Arg Val Pro Val Ser His Ser Phe Pro
 65                  70                  75                  80

His Pro Leu Tyr Asn Met Ser Leu Leu Lys His Gln Ser Leu Arg Pro
                 85                  90                  95

Asp Glu Asp Ser Ser His Asp Leu Met Leu Leu Arg Leu Ser Glu Pro
            100                 105                 110

Ala Lys Ile Thr Asp Val Val Lys Val Leu Gly Leu Pro Thr Gln Glu
        115                 120                 125

Pro Ala Leu Gly Thr Thr Cys Tyr Ala Ser Gly Trp Gly Ser Ile Glu
    130                 135                 140

Pro Glu Glu Phe Leu Arg Pro Arg Ser Leu Gln Cys Val Ser Leu His
145                 150                 155                 160

Leu Leu Ser Asn Asp Met Cys Ala Arg Ala Tyr Ser Glu Lys Val Thr
                165                 170                 175

Glu Phe Met Leu Cys Ala Gly Leu Trp Thr Gly Gly Lys Asp Thr Cys
            180                 185                 190

Gly Gly Asp Ser Gly Gly Pro Leu Val Cys Asn Gly Val Leu Gln Gly
        195                 200                 205

Ile Thr Ser Trp Gly Pro Glu Pro Cys Ala Leu Pro Glu Lys Pro Ala
    210                 215                 220

Val Tyr Thr Lys Val Val His Tyr Arg Lys Trp Ile Lys Asp Thr Ile
225                 230                 235                 240

Ala Ala Asn Pro
```

<210> SEQ ID NO 6
<211> LENGTH: 766
<212> TYPE: DNA
<213> ORGANISM: Homo sapiens

<400> SEQUENCE: 6

```
gtgcccctca tccagtctcg gattgtggga ggctgggagt gtgagaagca ttcccaaccc    60
tggcaggtgg ctgtgtacag tcatggatgg gcacactgtg ggggtgtcct ggtgcacccc   120
cagtgggtgc tcacagctgc ccattgccta aagaagaata gccaggtctg ctgggtcgg   180 cacaacctgt ttgagcctga agacacaggc cagagggtcc ctgtcagcca cagcttccca   240
cacccgctct acaatatgag ccttctgaag catcaaagcc ttagaccaga tgaagactcc   300
agccatgacc tcatgctgct ccgcctgtca gagcctgcca agatcacaga tgttgtgaag   360
```

-continued

```
gtcctgggcc tgcccaccca ggagccagca ctggggacca cctgctacgc ctcaggctgg      420
ggcagcatcg aaccagagga gttcttgcgc cccaggagtc ttcagtgtgt gagcctccat      480
ctcctgtcca atgacatgtg tgctagagct tactctgaga aggtgacaga gttcatgttg      540
tgtgctgggc tctggacagg tggtaaagac acttgtgggg gtgattctgg gggtccactt      600
gtctgtaatg gtgtgcttca aggtatcaca tcatggggcc ctgagccatg tgccctgcct      660
gaaaagcctg ctgtgtacac caaggtggtg cattaccgga agtggatcaa ggacaccatc      720
gcagccaacc cctgagtgcc cctgtcccac ccctacctct agtaaa                    766
```

<210> SEQ ID NO 7
<211> LENGTH: 237
<212> TYPE: PRT
<213> ORGANISM: Homo sapiens

<400> SEQUENCE: 7

```
Ile Val Gly Gly Trp Glu Cys Glu Lys His Ser Gln Pro Trp Gln Val
 1               5                  10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

<210> SEQ ID NO 8
<211> LENGTH: 237
<212> TYPE: PRT
<213> ORGANISM: Artificial Sequence
<220> FEATURE:
<223> OTHER INFORMATION: This is a variant of hK2 (Homo sapiens) with an
      alanine-to-valine substitution at amino acid 217.

<400> SEQUENCE: 8

```
Ile Val Gly Gly Trp Glu Cys Glu Lys His Ser Gln Pro Trp Gln Val
```

```
                1               5                    10                   15
Ala Val Tyr Ser His Gly Trp Ala His Cys Gly Gly Val Leu Val His
                    20                  25                  30

Pro Gln Trp Val Leu Thr Ala Ala His Cys Leu Lys Lys Asn Ser Gln
            35                  40                  45

Val Trp Leu Gly Arg His Asn Leu Phe Glu Pro Glu Asp Thr Gly Gln
    50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Ser Ser His Asp
                85                  90                  95

Leu Met Leu Leu Arg Leu Ser Glu Pro Ala Lys Ile Thr Asp Val Val
                100                 105                 110

Lys Val Leu Gly Leu Pro Thr Gln Glu Pro Ala Leu Gly Thr Thr Cys
                115                 120                 125

Tyr Ala Ser Gly Trp Gly Ser Ile Glu Pro Glu Glu Phe Leu Arg Pro
    130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
                180                 185                 190

Leu Val Cys Asn Gly Val Leu Gln Gly Ile Thr Ser Trp Gly Pro Glu
                195                 200                 205

Pro Cys Ala Leu Pro Glu Lys Pro Val Val Tyr Thr Lys Val Val His
    210                 215                 220

Tyr Arg Lys Trp Ile Lys Asp Thr Ile Ala Ala Asn Pro
225                 230                 235

<210> SEQ ID NO 9
<211> LENGTH: 32
<212> TYPE: DNA
<213> ORGANISM: Homo sapiens

<400> SEQUENCE: 9
acgcggatcc agcatgtggg acctggttct ct                              32

<210> SEQ ID NO 10
<211> LENGTH: 33
<212> TYPE: DNA
<213> ORGANISM: Homo sapiens

<400> SEQUENCE: 10
acagctgcag tttactagag gtaggggtgg gac                             33

<210> SEQ ID NO 11
<211> LENGTH: 42
<212> TYPE: DNA
<213> ORGANISM: Homo sapiens

<400> SEQUENCE: 11
atatggatcc atatgtcagc atgtgggacc tggttctctc ca                   42

<210> SEQ ID NO 12
<211> LENGTH: 31
<212> TYPE: DNA
<213> ORGANISM: Homo sapiens
```

<400> SEQUENCE: 12
atatggatcc tcaggggttg gctgcgatgg t                              31

<210> SEQ ID NO 13
<211> LENGTH: 14
<212> TYPE: DNA
<213> ORGANISM: Homo sapiens

<400> SEQUENCE: 13
tcatctctgt atcc                                                 14

<210> SEQ ID NO 14
<211> LENGTH: 12
<212> TYPE: DNA
<213> ORGANISM: Homo sapiens

<400> SEQUENCE: 14
gagtaagctc ta                                                   12

<210> SEQ ID NO 15
<211> LENGTH: 20
<212> TYPE: DNA
<213> ORGANISM: Homo sapiens

<400> SEQUENCE: 15
gatgactcca gccacgacct                                           20

<210> SEQ ID NO 16
<211> LENGTH: 20
<212> TYPE: DNA
<213> ORGANISM: Homo sapiens

<400> SEQUENCE: 16
cacagacacc ccatcctatc                                           20

<210> SEQ ID NO 17
<211> LENGTH: 23
<212> TYPE: DNA
<213> ORGANISM: Homo sapiens

<400> SEQUENCE: 17
gagggttgtg tacagtcatg gat                                       23

<210> SEQ ID NO 18
<211> LENGTH: 23
<212> TYPE: DNA
<213> ORGANISM: Homo sapiens

<400> SEQUENCE: 18
acacactgaa gactcctggg gcg                                       23

<210> SEQ ID NO 19
<211> LENGTH: 19
<212> TYPE: PRT
<213> ORGANISM: Homo sapiens

<400> SEQUENCE: 19

Glu Lys His Ser Gln Pro Trp Gln Val Ala Val Tyr Ser His Gly Trp
 1               5                  10                  15

Ala His Cys

<210> SEQ ID NO 20
<211> LENGTH: 16
<212> TYPE: PRT
<213> ORGANISM: Homo sapiens

<400> SEQUENCE: 20

His Cys Leu Lys Lys Asn Ser Gln Val Trp Leu Gly Arg His Asn Leu
 1               5                  10                  15

<210> SEQ ID NO 21
<211> LENGTH: 15
<212> TYPE: PRT
<213> ORGANISM: Homo sapiens

<400> SEQUENCE: 21

His Leu Leu Ser Asn Asp Met Cys Ala Arg Ala Tyr Ser Glu Lys
 1               5                  10                  15

<210> SEQ ID NO 22
<211> LENGTH: 55
<212> TYPE: PRT
<213> ORGANISM: Homo sapiens

<400> SEQUENCE: 22

Ala Val Tyr Ser His Gly Trp Ala His Cys Gly Gly Val Leu His
 1               5                  10                  15

Pro Gln Trp Val Leu Thr Ala Ala His Cys Leu Lys Lys Asn Ser Gln
                 20                  25                  30

Val Trp Leu Gly Arg His Asn Leu Phe Glu Pro Glu Asp Thr Gly Gln
             35                  40                  45

Arg Val Pro Val Ser His Ser
         50                  55

<210> SEQ ID NO 23
<211> LENGTH: 711
<212> TYPE: DNA
<213> ORGANISM: Homo sapiens

<400> SEQUENCE: 23
attgtgggag gctgggagtg cgagaagcat tcccaaccct ggcaggtgct tgtggcctct     60
cgtggcaggg cagtctgcgg cggtgttctg gtgcaccccc agtgggtcct cacagctgcc    120
cactgcatca ggaacaaaag cgtgatcttg ctgggtcggc acagcctgtt tcatcctgaa    180
gacacaggcc aggtatttca ggtcagccac agcttcccac acccgctcta cgatatgagc    240
ctcctgaaga atcgattcct caggccaggt gatgactcca gccacgacct catgctgctc    300
cgcctgtcag agcctgccga gctcacggat gctgtgaagg tcatggacct gcccacccag    360
gagccagcac tggggaccac ctgctacgcc tcaggctggg gcagcattga accagaggag    420
ttcttgaccc caaagaaact tcagtgtgtg gacctccatg ttatttccaa tgacgtgtgt    480
gcgcaagttc accctcagaa ggtgaccaag ttcatgctgt gtgctggacg ctggacaggg    540
ggcaaaagca cctgctcggg tgattctggg ggcccacttg tctgtaatgg tgtgcttcaa    600
ggtatcacgt catggggcag tgaaccatgt gccctgcccg aaaggccttc cctgtacacc    660
aaggtggtgc attaccggaa gtggatcaag gacaccatcg tggccaaccc c             711

<210> SEQ ID NO 24
<211> LENGTH: 24
<212> TYPE: PRT
<213> ORGANISM: Homo sapiens -continued

<400> SEQUENCE: 24

Leu Lys Lys Asn Ser Gln Val Trp Leu Gly Arg His Asn Leu Phe Glu
1               5                   10                  15

Pro Glu Asp Thr Gly Gln Arg Val
            20

<210> SEQ ID NO 25
<211> LENGTH: 26
<212> TYPE: PRT
<213> ORGANISM: Homo sapiens

<400> SEQUENCE: 25

Cys Ala Leu Pro Glu Lys Pro Ala Val Tyr Thr Lys Val Val His Tyr
1               5                   10                  15

Arg Lys Trp Ile Lys Asp Thr Ile Ala Ala
            20                  25

<210> SEQ ID NO 26
<211> LENGTH: 12
<212> TYPE: PRT
<213> ORGANISM: Homo sapiens

<400> SEQUENCE: 26

Gln Val Ala Val Tyr Ser His Gly Trp Ala His Cys
1               5                   10

<210> SEQ ID NO 27
<211> LENGTH: 20
<212> TYPE: DNA
<213> ORGANISM: Homo sapiens

<400> SEQUENCE: 27
agttcttgcg ccccaggagt                                              20

<210> SEQ ID NO 28
<211> LENGTH: 20
<212> TYPE: DNA
<213> ORGANISM: Homo sapiens

<400> SEQUENCE: 28
cacaaagacg tgggtgacca                                              20

<210> SEQ ID NO 29
<211> LENGTH: 20
<212> TYPE: DNA
<213> ORGANISM: Homo sapiens

<400> SEQUENCE: 29
agttcttgac cccaaagaaa                                              20

<210> SEQ ID NO 30
<211> LENGTH: 20
<212> TYPE: DNA
<213> ORGANISM: Homo sapiens

<400> SEQUENCE: 30
tccaatgacg tgtgtgcgca                                              20

<210> SEQ ID NO 31
<211> LENGTH: 20
<212> TYPE: DNA
<213> ORGANISM: Homo sapiens

```
<400> SEQUENCE: 31
attgtatgtg ggggcagact                                                  20

<210> SEQ ID NO 32
<211> LENGTH: 20
<212> TYPE: DNA
<213> ORGANISM: Homo sapiens

<400> SEQUENCE: 32
ggccaacatc tgggtggcca                                                  20

<210> SEQ ID NO 33
<211> LENGTH: 6139
<212> TYPE: DNA
<213> ORGANISM: Homo sapiens

<400> SEQUENCE: 33
gctggatgtg gtggtgcatg cttgtggtct cagctatcct ggaggctgag acaggagaat      60
cggttgagtc tgggagttca aggctacagg gagctgcgat cacgccgctg cactccagcc     120
tgggaaacag agtgagactg tctcagaatt tttttaaaaa agaatcagtg atcatcccaa     180
cccctgttgc tgttcatcct gagcctgcct tctctggctt tgttccctag atcacatctc     240
catgatccat aggccctgcc caatctgacc tcacaccgtg ggaatgcctc cagactgatc     300
tagtatgtgt ggaacagcaa gtgctggctc tccctcccct tccacagctc tgggtgtggg     360 aggggggttgt ccagcctcca gcagcatggg gagggccttg gtcagcatct aggtgccaac     420
agggcaaggg cggggtcctg gagaatgaag gctttatagg gctcctcagg gaggcccccc     480
agccccaaac tgcaccacct ggccgtgtac acctgtgtca gcatgtggga cctggttctc     540
tccatcgcct tgtctgtggg gtgcactggt gagattgggg ggataaagga aggggggcgg     600
gttctgactc ttatgctgaa gccctttttcc tcccacccag tgcccagcc tcgtcccttc     660 agcccacagt tcagcccaga caatgtgccc ctgactcttc cacattgcaa tagtcctcat     720
gcccacacta ggtccccgct ccctcccact tacctcagac cttttctctcc attgcccagc     780 caaatccctg ctcccagctg ctttactaaa gagcaagttc ctaggcatct ctgtgtttct     840
ctttatgggg ttcaaaacct ttcaaggacc tctctccatg ccactggttc cttgacccct     900
atcactgggc tgcctcctga gcccctcagt cctaccacag tctactgact tttcccattc     960
agctgtgagc attcaaccct gtccctggaa ccttgacacc tggctcccca accctgtccc    1020
aggaaaccca gattccacca gacacttcct tcttccccccc cgaggctatc tggcctgaga    1080
caacaaatgc tgcctcccac cctgagtctg gcactgggac tttcagaact cctccttccc    1140
tgactctttg ccccagaccc gtcattcaat ggctagcttt ttccatggga agaagaacaa    1200
cgagcacccc caaccacaac ggccagttct ctgattccct aaatccgcac ccttttcaaa    1260
acctcaaaaa caaaacaaaa caaaacaaag caagaaacaa ctcaggcaaa acttgttgct    1320
taaccttgga catggtaaac catccaaaac cttcctctcc cagcaactaa acctctccac    1380
tgggcactta acctttggtt tcttggaacc tcttaatctc ttagaaccca cagctgccac    1440
cacatgccct tctcccaatg taagacccca aatcactcca aatgacccaa ccccaaccc    1500 atgcctcctt cagatatttc ccatgtcccc tactctgatc tctgggtca gctccgttct    1560 cgagagcatg aagcctcccg acctggtcca gccaccaacc cgctaacgca gggaatagct    1620
acagaattgc cagccctccc aggaccccctt gcttgtgtcc tggactccca gtcctggtcc    1680
tctgccccca tgtctcttca aacccacagc tcagctccct cccctatcca attcttttgg    1740
```

-continued

```
gtctgatccc cctgacccag cacccctcc gcaggtgccg tgcccctcat ccagtctcgg    1800
attgtgggag gctgggagtg tgagaagcat tcccaaccct ggcaggtggc tgtgtacagt    1860
catggatggg cacactgtgg gggtgtcctg gtgcacccc agtgggtgct cacagctgcc    1920
cattgcctaa agaagtaagt aggaccctgg gatctgggga gggaatggct gtgtcccaca    1980
ggaataacag cgggatgctt cccccagggt cacttctcag gtgaggcttc agactaaagg    2040
agagagggaa ggtcctggcc caggtcgcac ccggaggcag agctggggct ggaccactct    2100
ccccatggct gcctgggttt ctctctgtgt ctgatctcgc tgtgtctctt ggtatctggc    2160
tctggttgtg tctgtatgac tgtgttttgg tctctatgtc cctctctctt ttctgtctcc    2220
ctgtgtctgt gtctcccccg tctctgtctc tgggtctctc tgtggccatc tctgtcaccg    2280
tgtgtctcac cctgcatctc tttgcctgtc tttctctctg gtctctgcc tcagcccttc    2340 ctcatcacta ctgaacacac cccgtgaggt gggtggggag cacccagaaa aaggaaggac    2400
tttaagctca atgtgtgtgc atgtgagggg gtgcctgtca ttgcacagca ctctctgcag    2460
gacatccctc cacctgggg agacacaggg agggctggtt tcagctgtag ctgggtgcac    2520
agttgaggag ggaggaagga gaagggaaa caagaaagga ggggaaggtg gccgggcacg    2580
gtggcccacg cctgtaatcc cagcactttg ggaggccgag gtgggtggat catctgaggt    2640
caggagtttg aaaccagcct ggccaacatg gcaaaacccc gtctctacta aaatacaaa    2700 aagtagccag gcgtggtgct gcgcgcctgt aatccaatta ctagggaggc tgaggcagga    2760
gaatcgcttg aacccgggag gcagaggttg cagtgagccg agatcgtgcc actgcactcc    2820
agcctgggtg acagagcaag actccatctc agaaaaaaca aacaaacaaa caaacaacaa    2880
aaaaaatcga aggaggggga agggagctgg agagagaaag ggggacatgg ccctgagctg    2940
tgggccgggc cacccgccac tacagagccc tcactccagc cccagctgca ggtgagccac    3000
cctcatgcct ctcctcctcc ccctgctact ccacactcct cagatgcccc cgtggcctcc    3060 ctccttttc tctcccacac tgtatcaccc ctggcttcct ctctgctgtt tctccttctc    3120
tctctgactt cccgcatcct tttctcattt gtctatttct cactcccttc ctggttctgt    3180
tcttctcccc ttcctcttcc ccatgtctat ttcttgctgt ctctgtctct tctttgctca    3240
tcctaattct cactgttctc ccttctgttt ttgtcattcc tctgccattt tatgctctct    3300
cttttccact tcgtttcttt cagtttctgt ctctgcctct cacatgatca cactcctgtt    3360
ttctaactca ctgtctgtat ttcaccacga ctatatctcc ccgaccctg tgcttttctc    3420 actgtttctt tttcttccct ttggagtctc cctatcctc cctgccca tctacctttc    3480 cccattttct ctctcctcat gcatccaccc ccttcctccc caggaatagc caggtctggc    3540
tgggtcggca caacctgttt gagcctgaag acacaggcca gagggtccct gtcagccaca    3600
gcttcccaca cccgctctac aatatgagcc ttctgaagca tcaaagcctt agaccagatg    3660
aagactccag ccatgacctc atgctgctcc gcctgtcaga gcctgccaag atcacagatg    3720
ttgtgaaggt cctgggcctg cccacccagg agccagcact ggggaccacc tgctacgcct    3780
caggctgggg cagcatcgaa ccagaggagt gtacgcctgg gccagatggt gtagctggga    3840
gcccagatgc ctgggtctga gggaagtggg gccaaagaac caggtggggt ccggccacag    3900
cccagttttt ctctgaccca tagtcttgcg ccccaggagt cttcagtgtg tgagcctcca    3960
tctcctgtcc aatgacatgt gtgctagagc ttactctgag aaggtgacag agttcatgtt    4020
gtgtgctggg ctctggacag gtggtaaaga cacttgtggg gtgagtcatc cctactccca    4080
```

```
acatctggag gggaaaggtg agtgaagacc ctaattctgg gctgcaatct gaaagctaac     4140
cagacatctg cctcccctgc tccccagcta tagccacgcc ccctccccat gcctcatctg     4200
ccgccctcct tccccttcc ctgactccct caacacaaga ggtgattctc acagcataat      4260
tcacccattc ctgtgttgag cacatgctta ctgggcactg ctacgtgacc agcattgccg     4320
tagaccctgg gaagcagcag tgaacaggta gagagcagcc tctccctcct gcagccccca    4380
tgctggtgag gggcactggc aggaacagtg gacccaacat ggaaatgctg gagggtgtca    4440
ggaagtgatc gggctctggg gcagggagga ggggtgggga gtgtcactgg gaggggacat    4500
cctgcagaag gtaggagtga gcaaacaccc gctgcagggg aggggagagc cctgcggcac    4560
ctggggagc agagggagca gcacctgccc aggcctggga ggaggggccg ggagggcgtg      4620
aggaggagcg aggggctgc atggctggag tgagggatca ggggcagggc gcgagatggc     4680
ctcacacagg gaagagaggg cccctcctgc agggcctcac ctgggccaca ggaggacact    4740
gcttttcctc tgaggagtca ggagctgtgg atggtgctgg acagaagaag gacagggcct    4800
ggctcaggtg tccagaggct gtcgctggct ccctttggg atcagactgc agggagggag     4860
ggcggcaggg ttgtgggggg agtgacgatg aggatgacct gggggtggct ccaggccttg    4920
cccctgcctg ggccctcacc cagcctccct cacagtctcc tggccctcca gtctctcccc   4980
tccactccat cctccatctg gcctcagtgg gtcattctga tcactgaact gaccataccc     5040
agccctgccc acggccctcc atggctcccc aatgccctgg agaggggaca tctagtcaga    5100
gagtagtcct gaagaggtgg cctctgcgat gtgcctgtgg gggcagcaac ctgcagatgg    5160
tcccggccct catcctgctg acctgtctgc agggatgtcc tcctggacct tgcccctgtg    5220
caggagctgg accctgaagt cccctcccca taggccaaga ctggagcctt gttccctctg    5280
ttggactccc tgcccatatt cttgtgggag tgggttctgg agacatttct gtctgttcct    5340
gagagctggg aattgctctc agtcatctgc ctgcgcggtt ctgagagatg gagttgccta    5400
ggcagttatt ggggccaatc tttctcactg tgtctctcct cctttaccct tagggtgatt   5460
ctggggtcc acttgtctgt aatggggtgc ttcaaggtat cacatcatgg ggccctgagc    5520
catgtgccct gcctgaaaag cctgctgtgt acaccaaggt ggtgcattac cggaagtgga    5580
tcaaggacac catcgcagcc aaccctgag tgccctgtc ccaccctac ctctagtaaa       5640
tttaagtcca cctcacgttc tggcatcact tggcctttct ggatgctgga cacctgaagc    5700
ttggaactca cctggccgaa gctcgagcct cctgagtcct actgacctgt gctttctggt    5760
gtggagtcca gggctgctag gaaaaggaat gggcagacac aggtgtatgc caatgttct     5820
gaaatgggta taatttcgtc ctctccttcg gaacactggc tgtctctgaa gacttctcgc    5880
tcagtttcag tgaggacaca cacaaagacg tgggtgacca tgttgtttgt ggggtgcaga   5940
gatgggaggg gtgggcca cctggaagag tggacagtga cacaaggtgg acactctcta     6000
cagatcactg aggataagct ggagccacaa tgcatgaggc acacacacag caaggatgac    6060
gctgtaaaca tagcccacgc tgtcctgggg gcactgggaa gcctagataa ggccgtgagc    6120
agaaagaagg ggaggatcc                                                 6139
```

<210> SEQ ID NO 34
<211> LENGTH: 20
<212> TYPE: DNA
<213> ORGANISM: Homo sapiens

<400> SEQUENCE: 34
aaagccttag accagatgaa                                                20

<210> SEQ ID NO 35
<211> LENGTH: 20
<212> TYPE: DNA
<213> ORGANISM: Homo sapiens

<400> SEQUENCE: 35
ccatttcaga aacattggca								20

<210> SEQ ID NO 36
<211> LENGTH: 27
<212> TYPE: PRT
<213> ORGANISM: Homo sapiens

<400> SEQUENCE: 36

Cys Ala Leu Pro Glu Lys Pro Ala Val Tyr Thr Lys Val Val His Tyr
1               5                   10                  15

Arg Lys Trp Ile Lys Asp Thr Ile Ala Ala Asn
            20                  25

<210> SEQ ID NO 37
<211> LENGTH: 7
<212> TYPE: PRT
<213> ORGANISM: Homo sapiens

<400> SEQUENCE: 37

Val Pro Leu Ile Gln Ser Arg
1               5

<210> SEQ ID NO 38
<211> LENGTH: 13
<212> TYPE: PRT
<213> ORGANISM: Homo sapiens

<400> SEQUENCE: 38

Val Pro Leu Ile Gln Ser Arg Ile Val Gly Gly Trp Glu
1               5                   10

<210> SEQ ID NO 39
<211> LENGTH: 6
<212> TYPE: PRT
<213> ORGANISM: Homo sapiens

<400> SEQUENCE: 39

Ile Val Gly Gly Trp Glu
1               5

<210> SEQ ID NO 40
<211> LENGTH: 9
<212> TYPE: PRT
<213> ORGANISM: Homo sapiens

<400> SEQUENCE: 40

Ile Val Gly Gly Trp Glu Cys Glu Lys
1               5

<210> SEQ ID NO 41
<211> LENGTH: 11
<212> TYPE: PRT
<213> ORGANISM: Homo sapiens

<400> SEQUENCE: 41

Val Pro Leu Ile Gln Ser Arg Ile Val Gly Gly
1               5                   10

<210> SEQ ID NO 42
<211> LENGTH: 50
<212> TYPE: PRT
<213> ORGANISM: Homo sapiens

<400> SEQUENCE: 42

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys
    50

<210> SEQ ID NO 43
<211> LENGTH: 151
<212> TYPE: DNA
<213> ORGANISM: Homo sapiens

<400> SEQUENCE: 43
atgtgggacc tggttctctc catcgccttg tctgtggggt gcactggtgc cgtgcccctc      60
atccagtctc ggattgtggg aggctgggag tgtgagaagc attcccaacc ctggcaggtg     120
gctgtgtaca gtcatggatg ggcacactgt g                                    151

<210> SEQ ID NO 44
<211> LENGTH: 14
<212> TYPE: PRT
<213> ORGANISM: Homo sapiens

<400> SEQUENCE: 44

Asp Arg Val Tyr Ile His Pro Phe His Leu Leu Val Tyr Ser
1               5                   10

<210> SEQ ID NO 45
<211> LENGTH: 14
<212> TYPE: PRT
<213> ORGANISM: Homo sapiens

<400> SEQUENCE: 45

Val Pro Leu Ile Gln Ser Arg Ile Val Gly Gly Trp Glu Cys
1               5                   10

<210> SEQ ID NO 46
<211> LENGTH: 30
<212> TYPE: PRT
<213> ORGANISM: Homo sapiens

<400> SEQUENCE: 46

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 47
<211> LENGTH: 18
<212> TYPE: PRT
<213> ORGANISM: Homo sapiens

<400> SEQUENCE: 47

```
-continued

Cys Ser Gly Lys Ile Val Ile Ala Arg Tyr Gly Lys Val Phe Arg Gly
1               5                   10                  15

Asn Lys

<210> SEQ ID NO 48
<211> LENGTH: 11
<212> TYPE: PRT
<213> ORGANISM: Homo sapiens

<400> SEQUENCE: 48

Arg Lys Trp Ile Lys Asp Thr Ile Ala Ala Asn
1               5                   10

<210> SEQ ID NO 49
<211> LENGTH: 10
<212> TYPE: PRT
<213> ORGANISM: Homo sapiens

<400> SEQUENCE: 49

Lys Trp Ile Lys Asp Thr Ile Ala Ala Asn
1               5                   10
```